(12) United States Patent
Luo et al.

(10) Patent No.: US 10,604,785 B2
(45) Date of Patent: Mar. 31, 2020

(54) UBIQUITINATION SYSTEM AND THE USES THEREOF

(71) Applicant: Purdue Research Foundation, West Lafayette, IN (US)

(72) Inventors: Zhao-Qing Luo, West Lafayette, IN (US); Jiazhang Qiu, West Lafayette, IN (US); Chittaranjan Das, West Lafayette, IN (US); Michael Sheedlo, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 270 days.

(21) Appl. No.: 15/478,977

(22) Filed: Apr. 4, 2017

(65) Prior Publication Data

US 2017/0283852 A1    Oct. 5, 2017

Related U.S. Application Data

(60) Provisional application No. 62/318,268, filed on Apr. 5, 2016, provisional application No. 62/430,955, filed on Dec. 7, 2016.

(51) Int. Cl.
*C12Q 1/48* (2006.01)
*C12Q 1/34* (2006.01)

(52) U.S. Cl.
CPC ............... *C12Q 1/48* (2013.01); *C12Q 1/34* (2013.01); *C12Y 204/02036* (2013.01); *C12Y 306/05* (2013.01)

(58) Field of Classification Search
None
See application file for complete search history.

(56) References Cited

PUBLICATIONS

Zhou, Y., et al., "Diversity of bacterial manipulation of the host ubiquitin pathways", Cell. Microbiol. 17, 26-34 (2015).
Cui, J., et al., "Glutamine deamidation and dysfunction of ubiquitin/NEDD8 induced by a bacterial effector family", Science 329, 1215-1218 (2010).
Xu, L., et al., "Cell biology of infection by Legionella pneumophila" Microbes Infect., 15, 157-167 (2013).
Luo, Z., et al., "Multiple substrates of the Legionella pneumophila Dot/Icm system identified by interbacterial protein transfer", Proc. Natl Acad. Sci., USA 101, 841-846 (2004).
Huang, L., et al., "The E Block motif is associated with Legionella pneumophila translocated substrates", Cell. Microbiol., 13, 227-245 (2011).
Lifshitz, Z., et al., "Computational modeling and experimental validation of the Legionella and Coxiella virulence-related type-IVB secretion signal", Proc. Natl Acad. Sci., USA 110, E707-E715 (2013).
Fontana, M., et al., "Secreted bacterial effectors that inhibit host protein synthesis are critical for induction of the innate immune response to virulent Legionella pneumophila", PLoS Pathog., 7, e1001289 (2011).
Choy, A., et al.,"The Legionella effector RavZ inhibits host autophagy through irreversible Atg8 deconjugation", Science 338, 1072-1076 (2012).
Simon, S., et al., "Icm/Dot-dependent inhibition of phagocyte migration by Legionella is antagonized by a translocated Ran GTPase activator", Cell. Microbiol. 16, 977-992 (2014).
Rolando, M., et al., "Legionella pneumophila effector RomA uniquely modifies host chromatin to repress gene expression and promote intracellular bacterial replication", Cell Host Microbe 13, 395-405 (2013).
Hsu, F., et al., "Structural basis for substrate recognition by a unique Legionella phosphoinositide phosphatase", Proc. Natl Acad. Sci. USA 109, 13567-13572 (2012).
Zhu, W., et al, "Cell biology and immunology lessons taught by Legionella pneumophila", Sci. China Life Sci. 59, 3-10 (2016).
Bardill, J., et al., "IcmS-dependent translocation of SdeA into macrophages by the Legionella pneumophila type IV secretion system", Mol. Microbiol. 56, 90-103 (2005).
Sakurai, J., et al., "Clostridium perfringens iota-toxin: structure and function", Toxins (Basel) 1, 208-228 (2009).
Wilde, C., et al., "The Rho-ADP-ribosylating C3 exoenzyme from Clostridium botulinum and related C3-like transferases", Toxicon 39, 1647-1660 (2001).
Ganesan, A., et al., "Pseudomonas aeruginosa exoenzyme S ADP-ribosylates Ras at multiple sites", J. Biol. Chem. 273, 7332-7337 (1998).
Simon, N., et al., "Novel bacterial ADP-ribosylating toxins: structure and function" Nature Rev. Microbiol. 12, 599-611 (2014).
Havey, J., et al., "Toxicity and SidJ-mediated suppression of toxicity require distinct regions in the SidE family of Legionella pneumophila effectors", Infect. Immun., 83, 3506-3514 (2015).
Jeong, K., et al., "Spatiotemporal regulation of a Legionella pneumophila T4SS substrate by the metaeffector SidJ", PLoS Pathog., 11, e1004695 (2015).
Tan, Y., et al., "Legionella pneumophila regulates the small GTPase Rab1 activity by reversible phosphorylcholination", Proc. Natl Acad. Science USA 108, 21212-21217 (2011).
Swanson, M., et al., "Association of Legionella pneumophila with the macrophage endoplasmic reticulum", Infect. Immun., 63, 3609-3620 (1995).
Liu, Y., et al., "The Legionella pneumophila effector SidJ is required for efficient recruitment of endoplasmic reticulum proteins to the bacterial phagosome", Infect. Immun., 75, 592-603 (2007).
Sherwood, R., et al., "Rab-centric perspective of bacterial pathogenoc-cupied vacuoles", Cell Host Microbe 14, 256-268 (2013).
Ortiz, S., et al., "Rab proteins of the endoplasmic reticulum: functions and interactors", Biochem. Soc. Trans. 40, 1426-1432 (2012).
Itoh, T., et al., "Golgi-resident small GTPase Rab33B interacts with Atg16L and modulates autophagosome formation", Mol. Biol. Cell 19, 2916-2925 (2008).
Sheedlo, M., et al.,"Structural basis of substrate recognition by a bacterial deubiquitinase important for dynamics of phagosome ubiquitination", Proc. Natl Acad. Sci. USA (2015).
Herhaus, L., et al.,, "Expanding the ubiquitin code through post-translationalmodification", EMBO Rep. 16, 1071-1083 (2015).

*Primary Examiner* — Iqbal H Chowdhury
(74) *Attorney, Agent, or Firm* — Purdue Research Foundation; Liang Zeng Yan

(57) ABSTRACT

An unprecedented mechanism of ubiquitination that is independent of E1 and E2 enzymes, instead relying on activation of ubiquitin by ADP-ribosylation, and which is mediated by members of the SidE effector family encoded by the bacterial pathogen *Legionella pneumophila* is disclosed. The herein disclosed method demonstrates a method in which ubiquitination can be carried out by a single enzyme. In addition, the present disclosure also provides compositions that may be used in ubiquitination assays and/or methods of screening active substance that may inhibit the ubiquitination process.

4 Claims, 26 Drawing Sheets

Specification includes a Sequence Listing.

| SEQ ID NO: | | | | | | |
|---|---|---|---|---|---|---|
| 1 | SdeA | 768 | PTRLFRGLNLS | ... 822 | GRTNASTTTEIKL | ... 862 HGEGTESEFSVYL |
| 2 | SdeB | 763 | PKKLYRGNLNL | ... 817 | GKTCASTTKNMKL | ... 857 HMTGSEDEFSVYL |
| 3 | SdeC | 753 | PKKLYRGNLNL | ... 812 | GKTCASTTKNMKL | ... 852 HMAGSEDEFSVYL |
| 4 | SidE | 775 | PTRLFRGLNLS | ... 829 | ARTCASTSTNIEV | ... 869 HVSGSESEYSIYL |
| 5 | IOTA | 331 | NLIVYRRSGPQ | ... 374 | YPNFISTSIGSVN | ... 414 PGYAGEYEVLLNH |
| 6 | C3 | 123 | NIMLFRGDDPA | ... 169 | EYGYISTSLMNVS | ... 207 SAFAGQLEMLLPR |
| 7 | ExoS | 314 | VVKTFRGTRGG | ... 338 | DDGYLSTSLNPGV | ... 374 SNYKNEKEILYNK |

FIG. 1A

SEQUENCE LISTING

<160> NUMBER OF SEQ ID NOS: 12

<210> SEQ ID NO 1
<211> LENGTH: 1506
<212> TYPE: PRT
<213> ORGANISM: Legionella pneumophila

<400> SEQUENCE: 1

Pro Val Trp Asn Gly Phe Ser Leu Tyr Thr Asp Asp Thr Val Lys Ala
1               5                   10                  15

Ala Ala Gln Tyr Ala Tyr Asp Asn Tyr Leu Gly Lys Pro Tyr Thr Gly
                20                  25                  30

Ser Val Glu Ser Ala Pro Ala Asn Phe Gly Gly Arg Met Val Tyr Arg
            35                  40                  45

Gln His His Gly Leu Ser His Thr Leu Arg Thr Met Ala Tyr Ala Glu
        50                  55                  60

Leu Ile Val Glu Glu Ala Arg Lys Ala Lys Leu Arg Gly Glu Thr Leu
65                  70                  75                  80

Gly Lys Phe Lys Asp Gly Arg Thr Ile Ala Asp Val Thr Pro Gln Glu
                85                  90                  95

Leu Lys Lys Ile Met Ile Ala Gln Ala Phe Phe Val Ala Gly Arg Asp
            100                 105                 110

Asp Glu Ala Ser Asp Ala Lys Asn Tyr Gln Lys Tyr His Glu Gln Met
        115                 120                 125

Ser Leu Gly Glu Ala Ile Met Pro Lys Tyr Val Glu Gly Val Glu Leu
    130                 135                 140

Thr Gln Glu Gly Met His Ala Ile Phe Ala Arg Met Gly Tyr Gly Asp
145                 150                 155                 160

Ile Thr Ser Gly Ser Ile Tyr Asn Gly Val Pro Thr Ile Asp Thr Gly
                165                 170                 175

Ala Leu Asn Arg Gln Gly Phe Met Pro Val Leu Thr Gly Val Gly Pro
            180                 185                 190

His Arg Asp Ser Gly His Trp Ile Met Leu Ile Lys Gly Pro Gly Asn
        195                 200                 205

Gln Tyr Tyr Leu Phe Asp Pro Leu Gly Lys Thr Ser Gly Glu Gly Tyr
    210                 215                 220

Gln Asn Ile Leu Ala Ala Gln Leu Pro Met Gly Ser Thr Leu Ser Val
225                 230                 235                 240

Ile Pro Asn Gly Ser Gly Leu Asn Met Gly Leu Cys Gly Tyr Trp Val
                245                 250                 255

Ala Ser Ala Gly Leu Arg Ala His Gln Ala Leu Asn Gln His Asn Pro
            260                 265                 270

Pro Thr Leu Leu Asn Val Gly Gln Thr Ile Thr Asn Glu Met Arg Asn
        275                 280                 285

Glu Leu Asp His Asp Gly Tyr Arg Lys Ile Thr Gly Trp Leu Arg Ala
    290                 295                 300

Val Ala Asp Glu Phe Pro Glu Gly Asp Pro Gln Leu Asp Gly Lys Ala
305                 310                 315                 320

Leu Arg Glu Asn Thr Glu Lys Asp Leu Lys Ile Glu Ile Pro Thr Leu
                325                 330                 335

Val Leu Pro Gly Lys Asp Thr Ser Pro Lys Glu Met Ser Val Lys Pro
            340                 345                 350

Thr Ala Pro Gln Asp Lys Ser Val Ser Arg Asp Ala Phe Leu Lys Tyr
        355                 360                 365

Val Lys Asp Asn Glu Ser Thr Leu Ile Pro Asp Val Phe Lys Asp Gln
    370                 375                 380

Glu Asp Val Asn Phe Tyr Ala Arg Val Ile Glu Asp Lys Ser His Asp
385                 390                 395                 400

Trp Glu Ser Thr Pro Ala His Val Leu Ile Asn Gln Gly His Met Val
                405                 410                 415

```
Asp Leu Val Arg Val Lys Gln Pro Pro Glu Ser Phe Leu Gln Arg Tyr
            420                 425                 430

Phe Ser Ser Met Gln Arg Trp Ile Gly Ser Gln Ala Thr Glu Ala Val
        435                 440                 445

Phe Gly Ile Gln Arg Gln Phe Phe His Ala Thr Tyr Glu Val Val Ala
    450                 455                 460

Gly Phe Asp Ser Asp Asn Lys Glu Pro His Leu Val Val Ser Gly Leu
465                 470                 475                 480

Gly Arg Tyr Val Ile Gly Glu Asp Gly Gln Pro Ile Arg Glu Ala Pro
                485                 490                 495

Lys Lys Gly Gln Lys Glu Gly Asp Leu Lys Val Phe Pro Gln Thr Tyr
                500                 505                 510

Lys Leu Lys Glu Asn Glu Arg Leu Met Arg Val Asp Glu Phe Leu Lys
            515                 520                 525

Leu Pro Glu Ile Gln Asn Thr Phe Pro Gly Ser Gly Lys His Leu Gln
        530                 535                 540

Gly Gly Met Pro Gly Met Asn Glu Met Asp Tyr Trp Asn Arg Leu Asn
545                 550                 555                 560

Ser Leu Asn Arg Ala Arg Cys Glu Asn Asp Val Asp Phe Cys Leu Lys
                565                 570                 575

Gln Leu Gln Thr Ala His Asp Lys Ala Lys Ile Glu Pro Ile Lys Gln
            580                 585                 590

Ala Phe Gln Ser Ser Lys Gly Lys Glu Arg Arg Gln Pro Asn Val Asp
        595                 600                 605

Glu Ile Ala Ala Ala Arg Ile Ile Gln Gln Ile Leu Ala Asn Pro Asp
    610                 615                 620

Cys Ile His Asp His Val Leu Ile Asn Gly Gln Lys Leu Glu Gln
625                 630                 635                 640

Gln Phe Phe Arg Asp Leu Leu Ala Lys Cys Glu Met Ala Val Val Gly
                645                 650                 655

Ser Leu Leu Asn Asp Thr Asp Ile Gly Asn Ile Asp Thr Leu Met Arg
            660                 665                 670

His Glu Lys Asp Thr Glu Phe His Ser Thr Asn Pro Glu Ala Val Pro
        675                 680                 685

Val Lys Ile Gly Glu Tyr Trp Ile Asn Asp Gln Arg Ile Asn Asn Ser
    690                 695                 700

Ser Gly Asn Ile Thr Gln Lys Lys His Asp Leu Ile Phe Leu Met Gln
705                 710                 715                 720

Asn Asp Ala Trp Tyr Phe Ser Arg Val Asn Ala Ile Ala Gln Asn Arg
                725                 730                 735

Asp Lys Gly Ser Thr Phe Lys Glu Val Leu Ile Thr Thr Leu Met Thr
            740                 745                 750

Pro Leu Thr Ser Lys Ala Leu Val Asp Thr Ser Gln Ala Lys Pro Pro
        755                 760                 765

Thr Arg Leu Phe Arg Gly Leu Asn Leu Ser Glu Glu Phe Thr Lys Gly
    770                 775                 780

Leu Ile Asp Gln Ala Asn Ala Met Ile Ala Asn Thr Thr Glu Arg Leu
785                 790                 795                 800

Phe Thr Asp His Ser Pro Glu Ala Phe Lys Gln Ile Lys Leu Asn Asp
                805                 810                 815

Leu Ser Lys Met Ser Gly Arg Thr Asn Ala Ser Thr Thr Glu Ile
            820                 825                 830
```

-continued

```
Lys Leu Val Lys Glu Thr Trp Asp Ser Asn Val Ile Phe Glu Met Leu
            835                 840                 845

Asp Pro Asp Gly Leu Leu His Ser Lys Gln Val Gly Arg His Gly Glu
        850                 855                 860

Gly Thr Glu Ser Glu Phe Ser Val Tyr Leu Pro Glu Asp Val Ala Leu
865                 870                 875                 880

Val Pro Val Lys Val Thr Leu Asp Gly Lys Thr Gln Lys Gly Glu Asn
                885                 890                 895

Arg Tyr Val Phe Thr Phe Val Ala Val Lys Ser Pro Asp Phe Thr Pro
                    900                 905                 910

Arg His Glu Ser Gly Tyr Ala Val Glu Pro Phe Leu Arg Met Gln Ala
            915                 920                 925

Ala Lys Leu Ala Glu Val Lys Ser Ser Ile Glu Lys Ala Gln Arg Ala
        930                 935                 940

Pro Asp Leu Glu Thr Ile Phe Asn Leu Gln Asn Val Glu Ala Val
945                 950                 955                 960

Gln Tyr Ser His Leu Ser Thr Gly Tyr Lys Asn Phe Leu Lys Asn Thr
                965                 970                 975

Val Gly Pro Val Leu Glu Asn Ser Leu Ser Gly Leu Met Glu Ser Asp
                    980                 985                 990

Thr Asp Thr Leu Ser Lys Ala Leu  Ala Ala Phe Pro Ser  Asp Thr Gln
            995                 1000                1005

Trp Ser  Ala Phe Asn Phe Glu  Glu Ala Arg Gln Ala  Lys Arg Gln
        1010                1015                1020

Met Asp  Ala Ile Lys Gln Met  Val Gly Asn Lys Val  Val Leu Asp
        1025                1030                1035

Ala Leu  Thr Gln Cys Gln Asp  Ala Leu Glu Lys Gln  Asn Ile Ala
        1040                1045                1050

Gly Ala  Leu Asp Ala Leu Lys  Lys Ile Pro Ser Glu  Lys Glu Met
        1055                1060                1065

Gly Thr  Ile Arg Arg Glu Leu  Arg Glu Gln Ile Gln  Ser Ala Arg
        1070                1075                1080

Gln Glu  Leu Glu Ser Leu Gln  Arg Ala Val Val Thr  Pro Val Val
        1085                1090                1095

Thr Asp  Glu Lys Lys Val Arg  Glu Arg Tyr Asp Ala  Leu Ile Glu
        1100                1105                1110

Asn Thr  Ser Lys Lys Ile Thr  Glu Leu Glu Thr Gly  Lys Leu Pro
        1115                1120                1125

Asn Leu  Asp Ala Val Lys Lys  Gly Ile Ser Asn Leu  Ser Asn Leu
        1130                1135                1140

Lys Gln  Glu Val Thr Val Leu  Arg Asn Glu Lys Ile  Arg Met His
        1145                1150                1155

Val Gly  Thr Asp Lys Val Asp  Phe Ser Asp Val Glu  Lys Leu Glu
        1160                1165                1170

Gln Gln  Ile Gln Val Ile Asp  Thr Lys Leu Ala Asp  Ala Tyr Leu
        1175                1180                1185

Leu Glu  Val Thr Lys Gln Ile  Ser Ala Leu Asp Asn  Thr Lys Pro
        1190                1195                1200

Lys Asn  Gln Thr Glu Leu Lys  Thr Lys Ile Ala Ala  Phe Leu Asp
        1205                1210                1215

Arg Thr  Thr Asp Ile Glu Met  Leu Arg Asn Glu Arg  Ile Lys Lys
        1220                1225                1230

His Gly  Ser Ser Lys Asp Pro  Leu Asp Leu Ser Asp  Leu Asp Lys
```

```
    1235                1240                1245

Leu Ser  Gly Ser Leu Gln Arg  Ile Asn Gln Ser Leu  Val Ser Asp
    1250                1255                1260

Leu Ile  Thr Thr Ile Arg Val  Ser Ile Asn Gln Met  Glu Ala Lys
    1265                1270                1275

Thr Phe  His Glu Gln Glu Lys  Glu Ile Gln Gln Asn  Phe Glu Leu
    1280                1285                1290

Leu Ala  Lys Leu Glu Lys Thr  Leu Asp Lys Ser Lys  Thr Ser Glu
    1295                1300                1305

Lys Leu  Arg Glu Asp Ile Pro  Lys Leu Asn Asp Leu  Leu Val Ala
    1310                1315                1320

Lys Gln  Lys Ala Tyr Pro Gln  Met Val Gln Met Gln  Leu Lys Ser
    1325                1330                1335

Glu Val  Phe Val Thr Gln Leu  Arg Glu Val Cys Gln  Ala Asn His
    1340                1345                1350

Asp Asp  Leu Asp Lys Thr Arg  Asn Ala Arg Leu Arg  Glu Leu Asp
    1355                1360                1365

Arg Leu  Asp Arg Glu Ala Gly  Ile Thr Arg Met Val  Gly Asn Leu
    1370                1375                1380

Ile Trp  Gly Leu Thr Asn Lys  Val Gly Leu Thr Thr  Asp Glu Arg
    1385                1390                1395

Leu Asp  Ile Arg Thr Lys Gln  Gln Ser Leu Ala Arg  Phe Lys Asn
    1400                1405                1410

Glu Leu  Phe Asn Asp Lys Ile  Asp Thr Asp Gln Leu  Ile Ser Asn
    1415                1420                1425

Leu Ala  Arg Lys Arg Pro Ser  Glu Leu Gln Glu Gly  Leu Gly Ile
    1430                1435                1440

Ser Thr  Asp Asn Ala Met Glu  Leu His Leu Leu Leu  Thr Glu Leu
    1445                1450                1455

Ala Gly  Lys Thr Thr Ser Pro  Asp Glu Leu Glu Glu  Arg Met Lys
    1460                1465                1470

Ala Ile  Asp Asp Ile Ser Thr  Lys Ile Gly Arg Glu  Pro Glu His
    1475                1480                1485

Leu Lys  Phe Val Met Val Glu  Glu Asp Glu Ser Asn  Lys Lys Thr
    1490                1495                1500

Ile Gly  Phe
    1505

<210> SEQ ID NO 2
<211> LENGTH: 1926
<212> TYPE: PRT
<213> ORGANISM: Legionella pneumophila

<400> SEQUENCE: 2

Met Gly Glu Ser Lys Met Pro Lys Tyr Val Glu Gly Val Glu Leu Thr
1               5                   10                  15

Gln Glu Gly Met His Ala Ile Phe Ala Arg Met Gly His Pro Glu Ile
            20                  25                  30

Lys Ser Gly Thr Ile Tyr Asn Gly Val Pro Thr Ile Asp Gln Glu Ala
        35                  40                  45

Leu Asp Lys Gln Gly Phe Met Pro Val Leu Thr Gly Val Gly Pro Lys
    50                  55                  60

Arg Asp Ser Gly His Trp Ile Met Leu Ile Lys Gly Ser Gly Asn Gln
65                  70                  75                  80
```

-continued

```
Tyr His Leu Phe Asp Pro Met Gly Lys Ile Ser Gly Glu Gly Tyr Gln
                85                  90                  95
Asp Ile Leu Ala Thr Gln Leu Pro Lys Gly Ser Thr Leu Ser Val Ile
            100                 105                 110
Pro Asn Glu Pro Gly Leu Asn Lys Gly Leu Cys Gly Tyr Trp Val Ala
        115                 120                 125
Ser Val Gly Leu Lys Ala Cys Ser Ala Leu Asn Lys Asp Asn Pro Pro
    130                 135                 140
Asn Leu Glu Thr Leu Gly Gln Ile Thr Thr Asp Ala Met Lys Asp Glu
145                 150                 155                 160
Leu Thr Asp Asn Gly Tyr Leu Lys Ile Thr Gly Trp Leu Lys Ala Val
                165                 170                 175
Ala Asp Lys Phe Pro Glu Gly Asp Pro Gln Pro Asp Ala Lys Ala Leu
            180                 185                 190
Arg Gln Thr Thr Glu Lys Asp Leu His Ile Glu Ile Pro Ser Pro Val
        195                 200                 205
Ser Pro Val Lys Asp Thr Ala Pro Lys Glu Val Ser Thr Lys Pro Thr
    210                 215                 220
Ala Pro Gln Val Ala Pro Lys Tyr Ser Leu Asp Ser Lys Leu Leu Glu
225                 230                 235                 240
Asn Asp Asp Asp Val Leu Asp Thr Ile Lys Tyr Val His Lys Glu Tyr
                245                 250                 255
Leu Gly Lys Pro Tyr Pro Gly Pro Leu Lys Asn Pro Lys Ala Pro Glu
            260                 265                 270
Glu Gly Arg Leu Pro Pro Asn Glu Gly Pro Asp Arg Gly Pro His Gly
        275                 280                 285
Leu Ala His Thr Val Arg Thr Met Ala Cys Ala Glu Val Met Ile Glu
    290                 295                 300
Glu Ala Arg Lys Ala Gln Leu Arg Gly Glu Thr Leu Gly Lys Ala Lys
305                 310                 315                 320
Asn Gly Gln Thr Leu Ala Asp Val Thr Pro Glu Glu Leu Lys Lys Ile
                325                 330                 335
Leu Ile Ala Gln Ala Phe Phe Val Val Gly Arg Asp Asp Glu Arg Ser
            340                 345                 350
Gly Tyr Asp Asp Val His Lys Arg Asn Phe Tyr Ala Glu Tyr His Glu
        355                 360                 365
Lys Ser Glu Gln Ala Phe Arg Lys Tyr Val Glu Asp Asn Lys Leu Ile
    370                 375                 380
Gly Lys Ile Phe Lys Asp Gln Lys Glu Val Asp Phe Tyr Ala Ala Ile
385                 390                 395                 400
Ile Leu Asp Lys Asn His Glu Trp Asp Ala Thr Pro Ala His Ile Leu
                405                 410                 415
Ile Asn Gln Gly His Met Val Asp Leu Met Arg Thr Lys Ala Pro Ala
            420                 425                 430
Glu Val Ala Leu Glu Arg Thr Tyr Asn Thr Leu Lys Gly Thr Val Gly
        435                 440                 445
Ser Lys Gly Ala Glu Val Val Leu Lys Ala His Arg Asp Phe Phe Phe
    450                 455                 460
Ala Thr Gly Ala Val Val Pro Leu Val Asn Pro Glu Ala Ile Asp Asp
465                 470                 475                 480
Pro Ser Arg Gly Gly Pro Tyr Glu Asn Pro Tyr Ser Gly Glu Lys Phe
                485                 490                 495
Val Ile Val Asp Asp Lys Val Pro Ala Ser Lys Lys Asp Leu Pro Lys
```

```
                500             505             510
Ala Val Asn Arg Asp Tyr Lys Leu Lys Asp Asn Glu Arg Phe Leu Thr
            515                 520             525

Ile Lys Glu Tyr Tyr Ala Phe Pro Asp Val Gln Gln Thr Tyr Pro Gly
            530                 535             540

Tyr Lys Thr Arg Leu Glu Ala Ser Ser Tyr Tyr Phe Pro Thr Pro Phe
545                 550                 555                 560

Ala Gly Glu Cys Glu Gln Asn Pro Ala Lys Cys Leu Gly Ala Ile Gln
                565                 570             575

Lys Ala Arg Ser Lys Leu Gln Thr Asp Ala Ile Lys Asn Gly Phe Gln
            580                 585             590

Ser Ser Ser Glu Lys Glu Arg Arg Gln Pro Asn Met Asp Glu Ile Ala
            595                 600             605

Ala Ala Arg Ile Ile Gln Gln Ile Met Ala Asn Pro Asp Cys Ile His
            610                 615             620

Asp Asp His Val Leu Ile Asn Gly Gln Lys Leu Glu Glu Lys Phe Phe
625                 630                 635                 640

Arg Asp Leu Leu Ala Lys Cys Asp Met Ala Val Val Gly Ser Leu Leu
                645                 650             655

Asn Asp Thr Asp Ile Lys Asn Ile Asp Thr Leu Met Arg His Glu Lys
            660                 665             670

Asn Thr Glu Phe His Ser Thr Asp Pro Lys Ala Val Pro Val Lys Ile
            675                 680             685

Gly Asp Ala Trp Glu Asn Arg Ile Arg Thr Lys Gly Gly Asp Val Thr
            690                 695             700

Gln Met Lys His Asp Leu Ile Phe Leu Met Gln Asn Asp Ala Trp Tyr
705                 710                 715                 720

Phe Ser Arg Val Asn Ala Ile Ala Gln Asn Arg Asp Lys Gly Ser Asn
                725                 730             735

Phe Lys Glu Val Leu Phe Thr Thr Leu Met Thr Pro Leu Thr Asn Lys
                740                 745             750

Ser Leu Ile Asp Thr Ser His Val Pro Ala Pro Lys Lys Leu Tyr Arg
            755                 760             765

Gly Leu Asn Leu Pro Gln Glu Phe Thr Asn Lys Leu Ile Asn Gln Ser
            770                 775             780

Asn Ala Ile Ile Ala Asn Thr Glu Asn Thr Leu Phe Thr Asp Leu Ser
785                 790                 795                 800

Ala Glu Ala Phe Lys Gln Ile Lys Leu Asn Asp Phe Ser Gln Met Ser
                805                 810             815

Gly Lys Thr Cys Ala Ser Thr Thr Lys Asn Met Lys Leu Leu Thr Asp
                820                 825             830

Ile Trp Gly Ser Asn Val Ile Phe Glu Met Leu Asp Pro Asp Gly Leu
            835                 840             845

Leu His Pro Lys Gln Val Gly Thr His Met Thr Gly Ser Glu Asp Glu
            850                 855             860

Phe Ser Val Tyr Leu Pro Glu Asp Val Ala Leu Val Pro Thr Lys Val
865                 870                 875                 880

Thr Leu Glu Gly Lys Thr Asp Thr Gly Glu Asp Arg Tyr Ile Phe Thr
                885                 890             895

Leu Val Ala Val Lys Ser Pro Asp Phe Ile Pro Arg His Glu Ser Gly
            900                 905             910

Tyr Ala Val Glu Pro Phe Met Lys Met Gln Lys Glu Lys Val Thr Gln
            915                 920             925
```

```
Ala Leu Asp Ala Ile Glu Lys Asp Lys Asp Ser Tyr Asn Ile Asp Glu
            930                 935                 940

Gln Leu Lys Ser Leu Arg Thr Glu Met Val Arg Gln Ala Lys Leu Pro
945                 950                 955                 960

Leu Arg Glu Gly Val Phe Asp Arg Leu Ser His Arg Phe Ser Leu Glu
                965                 970                 975

Thr Ser Asp Asn Lys Ile Ser Pro Glu Arg Arg Asp Phe Leu Asn Gln
            980                 985                 990

His Val Ile Pro Val Leu Gln Glu Cys His Ile Ala Leu Arg Thr Asn
        995                 1000                1005

Asn Met Glu Met Met Gln Lys Ala Leu Ala Lys Phe Pro Thr Asp
        1010                1015                1020

Lys Gln Trp Ser Ala Phe Lys Ser Gly Glu Ala Val Arg Ala Lys
    1025                1030                1035

Ala Gln Met Asp Val Leu Lys Gln Gln Ile Glu Lys Lys Ile Met
    1040                1045                1050

Leu Gln Thr Gln Ile Ile Pro Ala Leu Thr Glu Cys Gly Glu Ala
    1055                1060                1065

Leu Asp Lys Gln Asn Val Thr Glu Ala Leu Gln Ala Leu Asn Lys
    1070                1075                1080

Leu Pro Ala Glu Lys Glu Ile Gly Lys Ala Lys Gly Ile Gly Gln
    1085                1090                1095

Glu Leu Arg Gly Gln Ile Val Gly Val Lys Gln Glu Leu Thr Gly
    1100                1105                1110

Asn Leu Glu Ser Leu Gln Arg Ala Val Thr Thr Pro Val Val Lys
    1115                1120                1125

Asp Ala Glu Lys Met Arg Val Arg Tyr Glu Thr Leu Leu Thr Asp
    1130                1135                1140

Val Thr Lys Arg Val Thr Asp Phe Glu Lys Ile Lys Pro Ala Asn
    1145                1150                1155

Leu Asp Gly Tyr Asn Lys Ala Ile Ala Asp Leu Asn Asn Ile Gln
    1160                1165                1170

Gln Glu Leu Asn Leu Leu Arg Asn Glu Lys Ile Arg Met His Thr
    1175                1180                1185

Asp Lys Asp Lys Ala Val Asp Phe Ser Asp Ile Glu Ala Leu Glu
    1190                1195                1200

Lys Arg Leu Lys Glu Ala Gln Pro Asn Leu Tyr Pro Ser Leu Val
    1205                1210                1215

Glu Gly Thr Thr Lys Gly Ile Gln Glu Leu Glu Lys Ile Pro Lys
    1220                1225                1230

Ser Ile Ser Phe Asp Asp Val Lys Ser Met Thr Ser Lys Ile Asn
    1235                1240                1245

Gly Tyr Leu Glu Thr Leu Glu Phe Ile Arg Asn Glu Arg Val Lys
    1250                1255                1260

Lys His Gly Glu Ser Thr Glu Pro Leu Asp Met Ser Asp Leu Asp
    1265                1270                1275

Lys Leu Lys Asn Gln Leu Gln Gly Val Ser Gln His Leu Ala Gln
    1280                1285                1290

Ile Leu Leu Asn Gly Ala Lys Asn Ser Leu Asp Lys Ile Lys Asp
    1295                1300                1305

Pro Val Thr Leu Glu Lys Glu Gly Gln Tyr Ile Lys Arg Cys Leu
    1310                1315                1320
```

```
Asp His Phe Ala Glu Leu Glu Lys Thr Leu Asp Ser Ser Val Lys
1325                1330                1335

Gly Met Lys Gln Lys Glu Asp Phe Asn Thr Tyr Lys Asn Ser Leu
1340                1345                1350

Met Glu Lys Gln Glu Lys Ala Tyr Pro Glu Met Leu Gln Leu Gln
1355                1360                1365

Tyr Lys Ser Glu Ala Leu Ile Thr Gln Leu Arg Asn Leu Cys Asn
1370                1375                1380

Ile His His Asp Asn Leu Ala Lys Thr Arg Glu Glu Gln Gln Gln
1385                1390                1395

Leu Leu Asn Lys Thr Gly Gly Ile Leu Gly Gly Phe Phe Ser Gln
1400                1405                1410

Ile Thr Thr Ala Ile Ser Gln Ala Glu Ser Lys Lys Ala Asn Glu
1415                1420                1425

Phe Ala Arg Phe Lys Thr Glu Leu Asn Asn Asp Lys Ser Asp Val
1430                1435                1440

Ser Gln Leu Ile Gln Phe Leu Val Lys Lys Lys Pro Ser Glu Leu
1445                1450                1455

Glu Glu Asn Leu Gly Ile Ser Lys Glu Asn Ala Glu Gln Leu His
1460                1465                1470

Gly Leu Leu Lys Gln Leu Asp Ala Lys Ala Thr Pro Ile Asp Lys
1475                1480                1485

Leu Gln Glu Asn Thr Arg Leu Ile Asp Glu Ile Ser Thr Lys Met
1490                1495                1500

Gly Ser Lys Pro Val Ser Pro Glu His Val Ala Ala Thr Lys Ala
1505                1510                1515

Arg Glu Tyr Tyr Gln Phe Leu Leu Tyr Gly Ala Thr Gln Lys Ile
1520                1525                1530

Gly Asn Phe Glu Lys Ile Lys Pro Ile Asp Pro Glu Ser Tyr Lys
1535                1540                1545

Lys Ala Met Ser Asp Leu Asn Asn Met Gln Glu Ala Leu Gln Phe
1550                1555                1560

Leu Arg Ser Glu Lys Ser Arg Ile His Asp Gly Lys Glu Lys Ala
1565                1570                1575

Val Glu Phe Ser Asp Ile Glu Ala Leu Glu Lys Arg Val Gln Asn
1580                1585                1590

Ala Gln Pro Lys Leu Leu Thr Ala Leu Leu Asp Lys Thr Thr Arg
1595                1600                1605

Glu Ile Ser Ala Leu Val Lys Ile Pro Arg Lys Leu Thr Phe Glu
1610                1615                1620

Asp Ile Lys Ser Met Thr Thr Lys Leu Asn Ser Tyr Leu Glu Thr
1625                1630                1635

Leu Glu Leu Ile Arg Asn Glu Arg Ile Lys Gln His Gly Lys Ser
1640                1645                1650

Pro Glu Leu Leu Asp Met Ser Asp Leu Asp Ser Leu Lys Gly Gln
1655                1660                1665

Leu Gln Thr Phe Asn Gln Asn Leu Thr Gly Met Ile Leu Asn Ala
1670                1675                1680

Thr Lys Asp Gly Leu Asp Arg Ile Asn Asp Arg Ala Asn Phe Lys
1685                1690                1695

Glu Gly Glu Pro Tyr Val Lys Ala Cys Leu Asp Leu Leu Thr Glu
1700                1705                1710

Leu Glu Lys Thr Leu Asp Ser Ser Val Lys Gly Met Lys Gln Lys
```

```
    1715                1720                1725

Glu Asp  Ile Ser Ala Cys Arg  Asn Ser Leu Leu Asp  Lys Gln Glu
    1730                1735                1740

Lys Ala  Asn Ser Gly Met Leu  Asp Leu Gln Ser Lys  Ser Lys Asp
    1745                1750                1755

Leu Val  Thr Gln Leu Arg Asp  Ile Cys Lys Ile His  His Gly Asn
    1760                1765                1770

Leu Ala  Glu Ala Arg Arg Thr  Arg Leu His Ser Leu  Asp Asn Gln
    1775                1780                1785

Glu Gly  Gly Leu Leu Gly Gly  Leu Trp Ser Val Thr  Asn Lys Leu
    1790                1795                1800

Gly Val  Thr Thr Asp Thr Val  Gly Ile Glu Arg Met  Gln Ile Lys
    1805                1810                1815

Met Lys  Glu Gln Ala Leu Ala  Arg Phe Lys Thr Glu  Leu Asn Asn
    1820                1825                1830

Asp Lys  Tyr Asp Thr Asn Gln  Val Ile Ala Phe Leu  Ala Asn Lys
    1835                1840                1845

Lys Pro  Ser Glu Leu Glu Glu  Gly Leu Gly Ile Ser  Lys Glu Asn
    1850                1855                1860

Ala Glu  Glu Leu His Gly Leu  Leu Ser Lys Leu Thr  Ser Lys Met
    1865                1870                1875

Thr Ser  Lys Ile Glu Ile Glu  Glu Asn Thr Gln Leu  Ile Asp Glu
    1880                1885                1890

Ile Ser  Thr Lys Ile Gly Thr  Glu Pro Val Lys Leu  Glu Ser Thr
    1895                1900                1905

His Thr  Val Asp Glu Asp Glu  Arg Asp Thr Tyr His  Arg Glu Ser
    1910                1915                1920

Gly Tyr  Phe
    1925

<210> SEQ ID NO 3
<211> LENGTH: 1533
<212> TYPE: PRT
<213> ORGANISM: Legionella pneumophila

<400> SEQUENCE: 3

Met Pro Lys Tyr Val Glu Gly Val Glu Leu Thr Gln Glu Gly Met His
1               5                   10                  15

Ala Ile Phe Ala Arg Met Gly His Gly Asp Ile Thr Ser Gly Ser Ile
            20                  25                  30

Tyr Asn Gly Val Pro Thr Ile Asp Thr Glu Ala Leu Asn Arg Gln Gly
        35                  40                  45

Phe Met Pro Val Leu Thr Gly Val Gly Pro Arg Arg Asp Ser Gly His
    50                  55                  60

Trp Ile Met Leu Ile Lys Gly Pro Gly Asn Gln Tyr Phe Leu Phe Asp
65                  70                  75                  80

Pro Leu Gly Lys Thr Ser Gly Glu Gly Tyr Lys Asn Thr Leu Leu Ala
                85                  90                  95

Gln Leu Pro Ile Ala Ser Thr Leu Ser Val Ile Pro Asn Glu Pro Gly
            100                 105                 110

Leu Asn Lys Gly Leu Cys Gly Tyr Trp Val Ala Ser Val Gly Leu Lys
        115                 120                 125

Ala Arg Ser Glu Leu Ser Lys Asp Asn Pro Pro Asn Leu Glu Thr Leu
    130                 135                 140
```

-continued

Gly Gln Ile Thr Thr Asp Ala Met Lys Asp Glu Leu Thr Asp Asn Gly
145                 150                 155                 160

Tyr Leu Lys Ile Thr Gly Trp Leu Lys Ala Val Ala Asp Lys Phe Pro
                165                 170                 175

Glu Gly Asp Pro Gln Pro Asp Ala Lys Ala Leu Arg Gln Thr Thr Glu
            180                 185                 190

Lys Asp Leu His Ile Glu Ile Pro Ser Pro Val Ser Pro Ile Lys Asp
        195                 200                 205

Thr Ala Pro Lys Glu Val Ser Thr Lys Pro Thr Ala Pro Gln Val Ala
210                 215                 220

Pro Lys His Ser Leu Asp Ser Lys Leu Leu Glu Asn Asp Asp Asp Val
225                 230                 235                 240

Leu Asp Thr Ile Lys Tyr Val His Lys Glu Tyr Leu Gly Lys Pro Tyr
                245                 250                 255

Pro Gly Pro Leu Lys Asn Pro Lys Ala Pro Glu Glu Gly Arg Leu Pro
            260                 265                 270

Pro Asn Glu Gly Pro Asp Arg Gly Pro His Gly Leu Ala His Thr Val
        275                 280                 285

Arg Thr Met Ala Cys Ala Glu Val Met Ile Glu Glu Ala Arg Lys Ala
290                 295                 300

Gln Leu Arg Gly Glu Thr Leu Gly Lys Ala Lys Asn Gly Gln Thr Leu
305                 310                 315                 320

Ala Asp Val Thr Pro Glu Glu Leu Lys Lys Ile Leu Ile Ala Gln Ala
                325                 330                 335

Phe Phe Val Val Gly Arg Asp Asp Glu Arg Ser Gly Tyr Asp Asp Val
            340                 345                 350

His Lys Arg Asn Phe Tyr Ala Glu Tyr His Glu Lys Ser Glu Gln Ala
        355                 360                 365

Phe Arg Lys Tyr Val Glu Asp Asn Lys Leu Ile Gly Lys Ile Phe Lys
        370                 375                 380

Asp Gln Lys Glu Val Asp Phe Tyr Ala Ala Ile Leu Asp Lys Asn
385                 390                 395                 400

His Glu Trp Asp Ala Thr Pro Ala His Ile Leu Ile Asn Gln Gly His
                405                 410                 415

Met Val Asp Leu Met Arg Thr Lys Ala Pro Ala Glu Val Ala Leu Glu
            420                 425                 430

Arg Thr Tyr Asn Thr Leu Lys Gly Thr Val Gly Ser Lys Gly Ala Glu
        435                 440                 445

Val Val Leu Lys Ala His Arg Asp Phe Phe Ala Thr Gly Ala Val
450                 455                 460

Val Pro Leu Val Asn Pro Glu Ala Ile Asp Asp Pro Ser Arg Gly Gly
465                 470                 475                 480

Pro Tyr Glu Asn Pro Tyr Ser Gly Glu Lys Phe Val Ile Val Asp Asp
                485                 490                 495

Lys Val Pro Ala Ser Lys Lys Asp Leu Pro Lys Ala Val Asn Arg Asp
            500                 505                 510

Tyr Lys Leu Lys Asp Asn Glu Arg Phe Leu Thr Ile Lys Glu Tyr Tyr
        515                 520                 525

Ala Phe Pro Asp Val Gln Gln Thr Tyr Pro Gly Tyr Lys Thr Arg Leu
        530                 535                 540

Glu Ala Ser Ser Tyr Tyr Phe Pro Thr Pro Phe Ala Gly Glu Cys Glu
545                 550                 555                 560

Gln Asn Pro Ala Lys Cys Leu Gly Ala Ile Gln Lys Ala Arg Ser Lys

-continued

```
            565                 570                 575
Leu Gln Thr Asp Ala Ile Lys Asn Gly Phe Gln Ser Ser Glu Lys
            580                 585                 590

Glu Arg Arg Gln Pro Asn Met Asp Glu Ile Ala Ala Arg Ile Ile
            595                 600                 605

Gln Gln Ile Met Ala Asn Pro Asp Cys Ile His Asp His Val Leu
            610                 615                 620

Ile Asn Gly Gln Lys Leu Glu Glu Lys Phe Phe Arg Asp Leu Leu Ala
625                 630                 635                 640

Lys Cys Asp Met Ala Val Val Gly Ser Leu Leu Asn Asp Thr Asp Ile
                    645                 650                 655

Lys Asn Ile Asp Thr Leu Met Arg His Glu Lys Asn Thr Glu Phe His
                660                 665                 670

Ser Thr Asp Pro Lys Ala Val Pro Val Lys Ile Gly Asp Ala Trp Glu
                675                 680                 685

Asn Arg Ile Arg Thr Lys Gly Gly Asp Val Thr Gln Met Lys His Asp
690                 695                 700

Leu Ile Phe Leu Met Gln Asn Asp Ala Trp Tyr Phe Ser Arg Val Asn
705                 710                 715                 720

Ala Ile Ala Gln Asn Arg Asp Lys Gly Ser Asn Phe Lys Glu Val Leu
                    725                 730                 735

Phe Thr Thr Leu Met Thr Pro Leu Thr Asn Lys Ser Leu Ile Asp Thr
                740                 745                 750

Ser His Val Pro Ala Pro Lys Lys Leu Tyr Arg Gly Leu Asn Leu Pro
                755                 760                 765

Gln Glu Phe Thr Asn Lys Leu Ile Asn Gln Ser Asn Ala Ile Ile Ala
            770                 775                 780

Asn Thr Glu Asn Thr Leu Phe Thr Asp Leu Ala Glu Ala Phe Lys
785                 790                 795                 800

Gln Ile Lys Leu Asn Asp Phe Ser Gln Met Ser Gly Lys Thr Cys Ala
                    805                 810                 815

Ser Thr Thr Lys Asn Met Lys Leu Leu Thr Asp Ile Trp Gly Ser Asn
                820                 825                 830

Val Ile Phe Glu Met Leu Asp Pro Asp Gly Leu Leu His Pro Lys Gln
            835                 840                 845

Val Gly Thr His Met Ala Gly Ser Glu Asp Glu Phe Ser Val Tyr Leu
            850                 855                 860

Pro Glu Asp Val Ala Leu Val Pro Thr Lys Val Thr Leu Glu Gly Lys
865                 870                 875                 880

Thr Asp Thr Gly Glu Asp Arg Tyr Ile Phe Thr Leu Val Ala Val Lys
                    885                 890                 895

Ser Pro Asp Phe Ile Pro Arg His Glu Ser Gly Tyr Ala Val Glu Pro
                900                 905                 910

Phe Met Lys Met Gln Lys Glu Lys Val Thr Gln Ala Leu Asp Ala Ile
            915                 920                 925

Glu Lys Asp Lys Asp Ser Tyr Asn Ile Asp Glu Gln Leu Lys Ser Leu
930                 935                 940

Arg Thr Glu Met Val Arg Gln Ala Lys Leu Pro Leu Arg Glu Gly Val
945                 950                 955                 960

Phe Asp Arg Leu Ser His Arg Leu Ser Leu Glu Thr Ser Asp Asn Lys
                965                 970                 975

Ile Ser Pro Glu Arg Arg Asp Phe Leu Asn Gln His Val Ile Pro Val
                980                 985                 990
```

-continued

```
Leu Gln Glu Cys His Ile Ala Leu Arg Ala Asn Asp Met Asp Met Met
        995             1000                1005

Gln Lys Ala Leu Ala Lys Phe Pro Thr Asp Lys Gln Trp Ser Ala
    1010            1015            1020

Phe Lys Ser Gly Glu Ala Val Arg Ala Lys Ala Gln Met Asp Val
    1025            1030            1035

Leu Lys Gln Gln Ile Glu Lys Lys Ile Met Leu Gln Thr Gln Ile
    1040            1045            1050

Ile Pro Ala Leu Thr Glu Cys Gly Glu Ala Leu Asp Lys Gln Asn
    1055            1060            1065

Val Thr Glu Ala Leu Gln Ala Leu Asn Lys Leu Pro Ala Glu Lys
    1070            1075            1080

Glu Ile Gly Lys Val Lys Thr Ile Gly Gln Glu Leu Arg Gly Gln
    1085            1090            1095

Ile Val Gly Val Lys Gln Glu Leu Thr Gly Asn Leu Glu Pro Leu
    1100            1105            1110

Gln Arg Ala Thr Thr Thr Pro Ile Val Gln Asp Ala Glu Lys Ile
    1115            1120            1125

Lys Val Arg Tyr Glu Thr Leu Leu Thr Asp Val Thr Lys Arg Val
    1130            1135            1140

Thr Asp Phe Glu Lys Ile Lys Pro Ala Asn Leu Asp Gly Tyr Asn
    1145            1150            1155

Lys Ala Ile Ala Asp Leu Asn Asn Ile Gln Gln Glu Leu Asn Leu
    1160            1165            1170

Leu Arg Asn Glu Lys Ile Arg Met His Thr Asp Lys Asp Lys Ala
    1175            1180            1185

Val Asp Phe Ser Asp Ile Glu Ala Leu Asp Lys Arg Leu Gln Asp
    1190            1195            1200

Val Gln Ser Lys Leu Pro Thr Gln Leu Leu Glu Gln Thr Ser Lys
    1205            1210            1215

Asp Val Ala Lys Leu Ala Lys Met Pro Glu Lys Ile Thr Phe Asn
    1220            1225            1230

Asp Ile Lys Ser Met Thr Ser Lys Met Asn Asn Tyr Leu Glu Thr
    1235            1240            1245

Leu Glu Leu Ile Arg Asn Asp Arg Ile Lys Lys His Ala Gly Ser
    1250            1255            1260

Thr Asp Pro Leu Asp Met Ser Asp Leu Asp Gly Leu Lys Gly Gln
    1265            1270            1275

Leu Gln Thr Tyr Asn Gln Ser Met Ala Asp Ile Leu Leu Arg Ala
    1280            1285            1290

Ala Lys Ser Ser Leu Asp Lys Ile Lys Asp Pro Ala Thr Phe Glu
    1295            1300            1305

Lys Glu Ser Pro Tyr Ile Lys Gln Cys Phe Asp His Leu Ala Glu
    1310            1315            1320

Leu Glu Lys Thr Leu Asp Asp Ser Asp Lys Gly Arg Lys Gln Lys
    1325            1330            1335

Glu Asp Phe Thr Ala Tyr Lys Ser Ala Leu Met Asp Lys Gln Glu
    1340            1345            1350

Lys Ala Tyr Pro Glu Met Leu Gln Leu Gln Tyr Lys Ser Glu Ala
    1355            1360            1365

Leu Ile Met Gln Leu Arg Asp Ile Cys Lys Ile His His Asp Asn
    1370            1375            1380
```

```
Leu Ala  Glu Ala Arg Arg Val  Arg Leu Gln Gln Leu  Asp Ser Gln
    1385                 1390                 1395

Gly Gly  Gly Leu Leu Gly Gly  Leu Trp Ala Val Thr  Asn Thr Ile
    1400                 1405                 1410

Gly Leu  Thr Thr Asp Asn Val  Asn Ile Glu Lys Met  Gln Ile Arg
    1415                 1420                 1425

Met Lys  Glu Gln Thr Leu Arg  Ala Phe Lys Thr Glu  Leu Thr Asn
    1430                 1435                 1440

Asp Lys  Leu Asn Thr Asp Gln  Val Ile Ala Phe Leu  Ala Lys Gly
    1445                 1450                 1455

Ser Pro  Ser Glu Leu Gln Glu  Ala Leu Gly Ile Ser  Lys Glu Asn
    1460                 1465                 1470

Ala Glu  Gln Leu His Gly Leu  Leu Lys Gln Leu Glu  Ile Lys Thr
    1475                 1480                 1485

Ala Ser  Thr Asp Lys Leu Gln  Glu Ile Glu Lys Leu  Ile Asp Glu
    1490                 1495                 1500

Val Ser  Thr Lys Ile Gly Lys  Glu Pro Val Lys Gln  Asp His Thr
    1505                 1510                 1515

Ile Thr  Ile Asp Glu Glu Glu  Ser Asp Asp Ile Arg  Tyr Gly Phe
    1520                 1525                 1530

<210> SEQ ID NO 4
<211> LENGTH: 1514
<212> TYPE: PRT
<213> ORGANISM: Legionella pneumophila

<400> SEQUENCE: 4

Met Leu Ile Phe Lys Ser Gln Ile Leu Ile Leu Lys Tyr Leu Ser Arg
1               5                   10                  15

Ser Cys Val Met Pro Lys Tyr Val Glu Gly Ile Glu Leu Thr Gln Glu
            20                  25                  30

Gly Met His Ala Ile Phe Glu Arg Met Gly His Pro Asn Ile Thr Ser
        35                  40                  45

Gly Thr Ile Tyr Asn Gly Glu Pro Thr Ile Asp Lys Gly Ala Leu Asp
    50                  55                  60

Arg Gln Gly Phe Met Pro Val Leu Thr Gly Val Ser Pro Arg Gln Asp
65                  70                  75                  80

Ser Gly His Trp Ile Met Leu Ile Lys Gly Gln Gly Asn Gln Tyr Phe
                85                  90                  95

Leu Phe Asp Pro Leu Gly Glu Ser Ser Gly Lys Tyr Tyr Gln Asn Ile
            100                 105                 110

Leu Ala Lys Lys Leu Pro Gly Ala Thr Leu Ser Val Ile Pro Asn Asn
        115                 120                 125

Ala Gly Leu Asn Met Gly Leu Cys Gly Tyr Trp Val Ala Ser Val Gly
    130                 135                 140

Leu Arg Ala His Ala Ala Leu Thr Gln Pro Ile Pro Pro Ser Leu Arg
145                 150                 155                 160

Asn Leu Gly Gln Thr Ile Thr Gln Glu Met Arg Asp Glu Leu Thr Gln
                165                 170                 175

Asp Gly Ser Glu Lys Ile Thr Gln Trp Leu Arg Ala Val Gly Asn Glu
            180                 185                 190

Phe Pro Asp Gly Asp Ile Gln Pro Asp Ala Thr Ala Leu Arg Arg Ala
        195                 200                 205

Thr Glu Lys Asn Val Arg Ile Asp Glu Phe Gln Pro Val Leu Thr Gly
    210                 215                 220
```

-continued

Thr Ser Pro Lys Glu Ile Ser Ile Asn Pro Thr Ala Pro Gln Glu Val
225                 230                 235                 240

Ser Val Pro Thr Trp Asn Gly Phe Ser Leu Tyr Thr Asp Glu Thr Val
            245                 250                 255

Arg Asn Ala Ala Arg Tyr Ala Tyr Asp Asn Tyr Leu Gly Lys Pro Tyr
                260                 265                 270

Thr Gly Thr Val Glu Ala Thr Pro Val Asn Phe Gly Gly Gln Met Val
            275                 280                 285

Tyr Arg Gln His His Gly Leu Ala His Thr Leu Arg Thr Met Ala Tyr
        290                 295                 300

Ala Glu Ile Ile Val Glu Ala Arg Lys Ala Lys Leu Arg Gly Glu
305                 310                 315                 320

Ser Leu Lys Thr Phe Ala Asp Gly Arg Thr Leu Ala Asp Val Thr Pro
                325                 330                 335

Glu Glu Leu Arg Lys Ile Met Ile Ala Gln Ala Phe Phe Val Thr Gly
            340                 345                 350

Arg Asp Asp Glu Glu Ser Ser Lys Asn Tyr Glu Lys Tyr His Glu Gln
        355                 360                 365

Ser Arg Asp Ala Phe Leu Lys Tyr Val Glu Glu Asn Lys Ser Thr Leu
370                 375                 380

Ile Pro Asp Val Phe Lys Asp Glu Lys Asp Val Lys Phe Tyr Ala Asp
385                 390                 395                 400

Val Ile Glu Asp Lys Asp His Lys Trp Ala Asp Ser Pro Ala His Val
                405                 410                 415

Leu Val Asn Gln Gly His Met Val Asp Leu Val Arg Val Lys Gln Pro
            420                 425                 430

Pro Glu Ser Tyr Leu Glu Tyr Tyr Phe Ser Gln Leu Gln Pro Trp Ile
        435                 440                 445

Gly Ser Thr Ala Thr Glu Ala Val Phe Ala Thr Gln Arg Gln Phe Phe
    450                 455                 460

His Ala Thr Tyr Glu Ala Val Ala Gly Phe Asp Ser Glu Asn Lys Glu
465                 470                 475                 480

Pro His Leu Val Val Asp Gly Leu Gly Arg Tyr Val Ile Gly Gln Asp
                485                 490                 495

Gly Asn Pro Ile Arg Glu Glu Ser Asp Asp Glu Asp Glu Glu Glu Ser
            500                 505                 510

Gly Glu Leu Lys Phe Phe Ser Gln Lys Lys Leu Glu Glu Asn Gln
        515                 520                 525

Arg Tyr Met Arg Val Asp Glu Tyr Leu Lys Leu Asp Glu Val Gln Lys
        530                 535                 540

Arg Phe Pro Gly Ala Gly Lys Lys Leu Asp Gly Gly Leu Pro Gly Leu
545                 550                 555                 560

Lys Glu Tyr Gln Tyr Leu Gln Arg Leu Asn Ser Ile Asn Arg Ala Arg
                565                 570                 575

Cys Glu Asn Asp Val Asp Phe Cys Leu Gly Gln Leu Gln Thr Ala His
            580                 585                 590

His Gln Thr Lys Ile Thr Pro Ile Lys Arg Ala Phe Gln Ser Ser Ser
        595                 600                 605

Glu Lys Ala Arg Arg Gln Pro Asn Met Asp Glu Ile Ala Ala Ala Arg
    610                 615                 620

Ile Val Gln Gln Ile Met Ala Asn Pro Asp Cys Ile His Asp Asp His
625                 630                 635                 640

```
Val Phe Leu Asn Gly Gln Lys Leu Glu Glu Lys Phe Arg Asp Leu
                    645                 650                 655

Leu Ala Lys Cys Asp Met Ala Ile Val Gly Ser Leu Leu Asn Asp Thr
            660                 665                 670

Asp Ile Arg Asn Ile Asp Thr Leu Met Gln His Glu Arg Asn Thr Glu
            675                 680                 685

Phe His Ser Thr Asp Ala Lys Ala Lys Pro Val Lys Leu Gly Glu Thr
            690                 695                 700

Trp Glu Lys Thr Ile Arg Ser Gly Gly Val Thr Gln Ile Lys His
705                 710                 715                 720

Asp Leu Ile Phe Leu Met Gln Asn Asp Ala Trp Tyr His Thr Arg Val
                725                 730                 735

Asn Ala Ile Ala Gln Asn Arg Asp Lys Asp Ser Thr Phe Lys Glu Val
                740                 745                 750

Leu Ile Thr Ala Leu Met Thr Pro Leu Thr Asn Lys Ser Leu Met Asp
                755                 760                 765

Thr Ser Arg Ser Pro Ala Pro Lys Thr Leu Phe Arg Gly Leu Asp Leu
        770                 775                 780

Ser Glu Glu Phe Lys Asn Lys Leu Ile Asn Gln Ala Glu Thr Ile Ile
785                 790                 795                 800

Ala Asn Thr Thr Glu His Leu Phe Thr Asp Leu Ser Thr Glu Ala Phe
                805                 810                 815

Lys Gln Ile Lys Leu Asn Asp Phe Ser Gln Val Ser Ala Arg Thr Cys
                820                 825                 830

Ala Ser Thr Ser Thr Asn Ile Glu Val Pro Arg Thr Ile Phe Gly Ser
        835                 840                 845

Asn Thr Ile Phe Glu Ile Leu Asp Pro Asp Gly Leu Leu His Pro Lys
    850                 855                 860

Gln Val Gly Thr His Val Ser Gly Ser Glu Ser Glu Tyr Ser Ile Tyr
865                 870                 875                 880

Leu Pro Glu Asp Val Ala Leu Val Pro Ile Lys Val Ser Phe Asp Gly
                885                 890                 895

Lys Thr Gly Lys Gly Lys Asp Arg His Ile Phe Thr Leu Val Ala Val
            900                 905                 910

Lys Ser Pro Asp Phe Thr Pro Arg His Glu Ser Gly Tyr Ala Val Gly
        915                 920                 925

Pro Leu Leu Lys Met Gln Thr Pro Lys Leu Glu Glu Ile Gln Arg Leu
    930                 935                 940

Val Glu Gln Ala Arg Glu Glu Pro Asp Leu Glu Arg Val Phe Asn Leu
945                 950                 955                 960

Gln Ser Arg Val Ala Arg Gln Ala Lys Phe Ser Thr Glu Ser Gly Tyr
            965                 970                 975

Lys Thr Phe Leu Asn Glu Lys Val Ala Pro Val Leu Glu Gln Ser Leu
            980                 985                 990

Asn Gly Leu Leu Asp Asn Asn Val Thr Ile Leu Gly Lys Val Leu Ser
        995                 1000                1005

Ala Phe Pro Ser Asp Gly Gln Trp Ser Ala Phe Asn Ser Val Glu
    1010                1015                1020

Ala Arg Gln Met Lys Ile Gln Met Asp Ala Ile Lys Gln Met Val
    1025                1030                1035

Glu Lys Lys Ala Val Leu Glu Gly Gln Ile Leu Pro Ala Leu Ala
    1040                1045                1050

Gln Cys Gln Asn Ala Leu Glu Lys Gln Asn Ile Ala Gly Ala Leu
```

-continued

```
            1055                1060                1065
Gln  Ala  Leu  Arg  Asn  Ile  Pro  Ser  Glu  Lys  Glu  Met  Gln  Thr  Met
            1070                1075                1080

Leu  Ser  Ile  Ser  Gly  Gly  Leu  Arg  Gly  Gln  Ile  Gln  Arg  Ala  Lys
            1085                1090                1095

Gln  Asp  Leu  Thr  Glu  Thr  Leu  Glu  Pro  Leu  Gln  Arg  Ala  Ile  Thr
            1100                1105                1110

Ala  Lys  Leu  Val  Ser  Asp  Gln  Glu  Lys  Val  Lys  Val  Arg  Tyr  Glu
            1115                1120                1125

Lys  Leu  Ile  Ala  Gly  Ile  Pro  Gln  Gln  Ile  Ala  Asp  Leu  Glu  Lys
            1130                1135                1140

Ala  Glu  Leu  Ala  Asp  Leu  Ala  Lys  Val  Lys  Val  Val  Ser  Arg
            1145                1150                1155

Phe  Asn  His  Leu  Gln  Glu  Glu  Leu  Lys  Leu  Leu  Arg  Asn  Glu  Lys
            1160                1165                1170

Ile  Arg  Met  His  Thr  Gly  Ser  Glu  Lys  Val  Asp  Phe  Ser  Asp  Ile
            1175                1180                1185

Ala  Gln  Leu  Glu  Ala  Gln  Leu  Gln  Lys  Ile  His  Thr  Lys  Leu  Tyr
            1190                1195                1200

Asp  Ala  Tyr  Leu  Val  Glu  Leu  Thr  Lys  Glu  Ile  Ser  Ala  Leu  Val
            1205                1210                1215

Lys  Glu  Lys  Pro  Lys  Asn  Leu  Ala  Asp  Val  Lys  Arg  Met  Val  Ser
            1220                1225                1230

Asn  Phe  Tyr  Ala  Met  Ser  Ala  Asp  Ile  Glu  Gln  Leu  Arg  Gln  Glu
            1235                1240                1245

Lys  Ile  Lys  Glu  His  Gly  Glu  Ser  Lys  Asp  Pro  Ile  Asp  Met  Ser
            1250                1255                1260

Asp  Ile  Asp  Lys  Leu  Lys  Glu  Glu  Leu  Gln  Lys  Ile  Asn  Gln  Phe
            1265                1270                1275

Leu  Val  Lys  Ala  Met  Gly  Thr  Asn  Ile  Arg  Val  Ser  Leu  Asn  Gln
            1280                1285                1290

Met  Glu  Val  Lys  Thr  Phe  Asp  Ala  Gln  Glu  Lys  Glu  Ala  Gln  Gln
            1295                1300                1305

Asn  Leu  Lys  Gln  Leu  Asp  Ala  Leu  Ile  Asn  Lys  Leu  Glu  Ser  Ser
            1310                1315                1320

Asp  Ala  Val  Gln  Lys  Gln  Lys  Glu  Glu  Leu  Glu  Lys  Leu  Asn  Gln
            1325                1330                1335

Leu  Leu  Val  Glu  Lys  Arg  Lys  Ala  Tyr  Pro  Ala  Met  Val  Gln  Leu
            1340                1345                1350

Gln  Phe  Arg  Ser  Glu  Ala  Leu  Ile  Ile  His  Leu  Arg  Glu  Leu  Cys
            1355                1360                1365

Glu  Ala  His  Gln  Ala  Gln  Met  Ala  Lys  Thr  Arg  Asn  Val  Arg  Ala
            1370                1375                1380

Gln  Glu  Ile  Thr  Asn  Gly  Arg  Trp  Lys  Val  Gln  Trp  Leu  Thr  Asp
            1385                1390                1395

Trp  Val  Gly  Leu  Thr  Thr  Asp  Glu  Arg  Val  Thr  Leu  Ala  Asn  Lys
            1400                1405                1410

Glu  Lys  Glu  Leu  Ala  Lys  Phe  Lys  Glu  Asp  Leu  Asn  Asn  Asp  Glu
            1415                1420                1425

Tyr  Asp  Leu  Gln  Glu  Leu  Ile  Ser  Asn  Leu  Ala  Glu  Lys  Asn  Pro
            1430                1435                1440

Ser  Glu  Leu  Glu  Glu  Ala  Ile  Gly  Ile  Ser  Lys  Glu  Ser  Ala  Gln
            1445                1450                1455
```

```
Lys Leu His Lys Leu Leu Thr His Leu Asn His Ser Thr Thr Phe
    1460                1465                1470

Met Ser Lys Ile Glu Gln Arg Leu Gln Ser Ile Asp Glu Leu Leu
    1475                1480                1485

Asn Glu Phe Gly Lys Gln Ala Pro Arg Thr Glu Met Ile Lys Thr
    1490                1495                1500

Val Glu Glu Lys Gln Gly Thr Leu Leu Arg Leu
    1505                1510

<210> SEQ ID NO 5
<211> LENGTH: 413
<212> TYPE: PRT
<213> ORGANISM: Clostridium perfringens

<400> SEQUENCE: 5

Ala Phe Ile Glu Arg Pro Glu Asp Phe Leu Lys Asp Lys Glu Asn Ala
1               5                   10                  15

Ile Gln Trp Glu Lys Lys Glu Ala Glu Arg Val Glu Lys Asn Leu Asp
            20                  25                  30

Thr Leu Glu Lys Glu Ala Leu Glu Leu Tyr Lys Lys Asp Ser Glu Gln
        35                  40                  45

Ile Ser Asn Tyr Ser Gln Thr Arg Gln Tyr Phe Tyr Asp Tyr Gln Ile
    50                  55                  60

Glu Ser Asn Pro Arg Glu Lys Glu Tyr Lys Asn Leu Arg Asn Ala Ile
65                  70                  75                  80

Ser Lys Asn Lys Ile Asp Lys Pro Ile Asn Val Tyr Tyr Phe Glu Ser
                85                  90                  95

Pro Glu Lys Phe Ala Phe Asn Lys Glu Ile Arg Thr Glu Asn Gln Asn
            100                 105                 110

Glu Ile Ser Leu Glu Lys Phe Asn Glu Leu Lys Glu Thr Ile Gln Asp
        115                 120                 125

Lys Leu Phe Lys Gln Asp Gly Phe Lys Asp Val Ser Leu Tyr Glu Pro
    130                 135                 140

Gly Asn Gly Asp Glu Lys Pro Thr Pro Leu Leu Ile His Leu Lys Leu
145                 150                 155                 160

Pro Lys Asn Thr Gly Met Leu Pro Tyr Ile Asn Ser Asn Asp Val Lys
                165                 170                 175

Thr Leu Ile Glu Gln Asp Tyr Ser Ile Lys Ile Asp Lys Ile Val Arg
            180                 185                 190

Ile Val Ile Glu Gly Lys Gln Tyr Ile Lys Ala Glu Ala Ser Ile Val
        195                 200                 205

Asn Ser Leu Asp Phe Lys Asp Asp Val Ser Lys Gly Asp Leu Trp Gly
    210                 215                 220

Lys Glu Asn Tyr Ser Asp Trp Ser Asn Lys Leu Thr Pro Asn Glu Leu
225                 230                 235                 240

Ala Asp Val Asn Asp Tyr Met Arg Gly Gly Tyr Thr Ala Ile Asn Asn
                245                 250                 255

Tyr Leu Ile Ser Asn Gly Pro Leu Asn Asn Pro Asn Pro Glu Leu Asp
            260                 265                 270

Ser Lys Val Asn Asn Ile Glu Asn Ala Leu Lys Leu Thr Pro Ile Pro
        275                 280                 285

Ser Asn Leu Ile Val Tyr Arg Arg Ser Gly Pro Gln Glu Phe Gly Leu
    290                 295                 300

Thr Leu Thr Ser Pro Glu Tyr Asp Phe Asn Lys Ile Glu Asn Ile Asp
```

```
            305                 310                 315                 320
    Ala Phe Lys Glu Lys Trp Glu Gly Lys Val Ile Thr Tyr Pro Asn Phe
                    325                 330                 335

Ile Ser Thr Ser Ile Gly Ser Val Asn Met Ser Ala Phe Ala Lys Arg
                    340                 345                 350

Lys Ile Ile Leu Arg Ile Asn Ile Pro Lys Asp Ser Pro Gly Ala Tyr
                    355                 360                 365

Leu Ser Ala Ile Pro Gly Tyr Ala Gly Glu Tyr Glu Val Leu Leu Asn
                    370                 375                 380

His Gly Ser Lys Phe Lys Ile Asn Lys Val Asp Ser Tyr Lys Asp Gly
    385                 390                 395                 400

Thr Val Thr Lys Leu Ile Leu Asp Ala Thr Leu Ile Asn
                    405                 410
```

<210> SEQ ID NO 6
<211> LENGTH: 211
<212> TYPE: PRT
<213> ORGANISM: Clostridium botulinum

<400> SEQUENCE: 6

```
Ala Tyr Ser Asn Thr Tyr Gln Glu Phe Thr Asn Ile Asp Gln Ala Lys
1               5                   10                  15

Ala Trp Gly Asn Ala Gln Tyr Lys Lys Tyr Gly Leu Ser Lys Ser Glu
                20                  25                  30

Lys Glu Ala Ile Val Ser Tyr Thr Lys Ser Ala Ser Glu Ile Asn Gly
            35                  40                  45

Lys Leu Arg Gln Asn Lys Gly Val Ile Asn Gly Phe Pro Ser Asn Leu
        50                  55                  60

Ile Lys Gln Val Glu Leu Leu Asp Lys Ser Phe Asn Lys Met Lys Thr
65                  70                  75                  80

Pro Glu Asn Ile Met Leu Phe Arg Gly Asp Asp Pro Ala Tyr Leu Gly
                85                  90                  95

Thr Glu Phe Gln Asn Thr Leu Leu Asn Ser Asn Gly Thr Ile Asn Lys
            100                 105                 110

Thr Ala Phe Glu Lys Ala Lys Ala Lys Phe Leu Asn Lys Asp Arg Leu
        115                 120                 125

Glu Tyr Gly Tyr Ile Ser Thr Ser Leu Met Asn Val Ser Gln Phe Ala
    130                 135                 140

Gly Arg Pro Ile Ile Thr Lys Phe Lys Val Ala Lys Gly Ser Lys Ala
145                 150                 155                 160

Gly Tyr Ile Asp Pro Ile Ser Ala Phe Ala Gly Gln Leu Glu Met Leu
                165                 170                 175

Leu Pro Arg His Ser Thr Tyr His Ile Asp Asp Met Arg Leu Ser Ser
            180                 185                 190

Asp Gly Lys Gln Ile Ile Ile Thr Ala Thr Met Met Gly Thr Ala Ile
        195                 200                 205

Asn Pro Lys
    210
```

<210> SEQ ID NO 7
<211> LENGTH: 453
<212> TYPE: PRT
<213> ORGANISM: Pseudomonas aeruginosa

<400> SEQUENCE: 7

Met His Ile Gln Ser Leu Gln Gln Ser Pro Ser Phe Ala Val Glu Leu

-continued

```
1               5                   10                  15
His Gln Ala Ala Ser Gly Arg Leu Gly Gln Ile Glu Ala Arg Gln Val
            20                  25                  30
Ala Thr Pro Ser Glu Ala Gln Gln Leu Ala Gln Arg Gln Asp Ala Pro
            35                  40                  45
Lys Gly Glu Gly Leu Leu Ala Arg Leu Gly Ala Ala Leu Met Arg Pro
            50                  55                  60
Phe Val Ala Ile Met Asp Trp Leu Gly Lys Leu Leu Gly Ser His Ala
65                  70                  75                  80
Arg Thr Gly Pro Gln Pro Ser Gln Asp Ala Gln Pro Ala Val Met Ser
            85                  90                  95
Ser Ala Val Val Phe Lys Gln Met Val Leu Gln Gln Ala Leu Pro Met
            100                 105                 110
Thr Leu Lys Gly Leu Asp Lys Ala Ser Glu Leu Ala Thr Leu Thr Pro
            115                 120                 125
Glu Gly Leu Ala Arg Glu His Ser Arg Leu Ala Ser Gly Asp Gly Ala
            130                 135                 140
Leu Arg Ser Leu Ser Thr Ala Leu Ala Gly Ile Arg Ala Gly Ser Gln
145                 150                 155                 160
Val Glu Glu Ser Arg Ile Gln Ala Gly Arg Leu Leu Glu Arg Ser Ile
            165                 170                 175
Gly Gly Ile Ala Leu Gln Gln Trp Gly Thr Thr Gly Gly Ala Ala Ser
            180                 185                 190
Gln Leu Val Leu Asp Ala Ser Pro Glu Leu Arg Arg Glu Ile Thr Asp
            195                 200                 205
Gln Leu His Gln Val Met Ser Glu Val Ala Leu Leu Arg Gln Ala Val
            210                 215                 220
Glu Ser Glu Val Ser Arg Val Ser Ala Asp Lys Ala Leu Ala Asp Gly
225                 230                 235                 240
Leu Val Lys Arg Phe Gly Ala Asp Ala Glu Lys Tyr Leu Gly Arg Gln
            245                 250                 255
Pro Gly Gly Ile His Ser Asp Ala Glu Val Met Ala Leu Gly Leu Tyr
            260                 265                 270
Thr Gly Ile His Tyr Ala Asp Leu Asn Arg Ala Leu Arg Gln Gly Gln
            275                 280                 285
Glu Leu Asp Ala Gly Gln Lys Leu Ile Asp Gln Gly Met Ser Ala Ala
            290                 295                 300
Phe Glu Lys Ser Gly Gln Ala Glu Gln Val Val Lys Thr Phe Arg Gly
305                 310                 315                 320
Thr Arg Gly Gly Asp Ala Phe Asn Ala Val Glu Glu Gly Lys Val Gly
            325                 330                 335
His Asp Asp Gly Tyr Leu Ser Thr Ser Leu Asn Pro Gly Val Ala Arg
            340                 345                 350
Ser Phe Gly Gln Gly Thr Ile Ser Thr Val Phe Gly Arg Ser Gly Ile
            355                 360                 365
Asp Val Ser Gly Ile Ser Asn Tyr Lys Asn Glu Lys Glu Ile Leu Tyr
            370                 375                 380
Asn Lys Glu Thr Asp Met Arg Val Leu Leu Ser Ala Ser Asp Glu Gln
385                 390                 395                 400
Gly Val Thr Arg Arg Val Leu Glu Glu Ala Leu Gly Glu Gln Ser
            405                 410                 415
Gly His Ser Gln Gly Leu Leu Asp Ala Leu Asp Leu Ala Ser Lys Pro
            420                 425                 430
```

-continued

Glu Arg Ser Gly Glu Val Gln Glu Gln Asp Val Arg Leu Arg Met Arg
            435                 440                 445

Gly Leu Asp Leu Ala
        450

<210> SEQ ID NO 8
<211> LENGTH: 1506
<212> TYPE: PRT
<213> ORGANISM: artificial
<220> FEATURE:
<223> OTHER INFORMATION: mutant of SdeA E/A

<400> SEQUENCE: 8

Pro Val Trp Asn Gly Phe Ser Leu Tyr Thr Asp Asp Thr Val Lys Ala
1               5                   10                  15

Ala Ala Gln Tyr Ala Tyr Asp Asn Tyr Leu Gly Lys Pro Tyr Thr Gly
                20                  25                  30

Ser Val Glu Ser Ala Pro Ala Asn Phe Gly Gly Arg Met Val Tyr Arg
            35                  40                  45

Gln His His Gly Leu Ser His Thr Leu Arg Thr Met Ala Tyr Ala Glu
        50                  55                  60

Leu Ile Val Glu Glu Ala Arg Lys Ala Lys Leu Arg Gly Glu Thr Leu
65                  70                  75                  80

Gly Lys Phe Lys Asp Gly Arg Thr Ile Ala Asp Val Thr Pro Gln Glu
                85                  90                  95

Leu Lys Lys Ile Met Ile Ala Gln Ala Phe Phe Val Ala Gly Arg Asp
            100                 105                 110

Asp Glu Ala Ser Asp Ala Lys Asn Tyr Gln Lys Tyr His Glu Gln Met
        115                 120                 125

Ser Leu Gly Glu Ala Ile Met Pro Lys Tyr Val Glu Gly Val Glu Leu
    130                 135                 140

Thr Gln Glu Gly Met His Ala Ile Phe Ala Arg Met Gly Tyr Gly Asp
145                 150                 155                 160

Ile Thr Ser Gly Ser Ile Tyr Asn Gly Val Pro Thr Ile Asp Thr Gly
                165                 170                 175

Ala Leu Asn Arg Gln Gly Phe Met Pro Val Leu Thr Gly Val Gly Pro
            180                 185                 190

His Arg Asp Ser Gly His Trp Ile Met Leu Ile Lys Gly Pro Gly Asn
        195                 200                 205

Gln Tyr Tyr Leu Phe Asp Pro Leu Gly Lys Thr Ser Gly Glu Gly Tyr
    210                 215                 220

Gln Asn Ile Leu Ala Ala Gln Leu Pro Met Gly Ser Thr Leu Ser Val
225                 230                 235                 240

Ile Pro Asn Gly Ser Gly Leu Asn Met Gly Leu Cys Gly Tyr Trp Val
                245                 250                 255

Ala Ser Ala Gly Leu Arg Ala His Gln Ala Leu Asn Gln His Asn Pro
            260                 265                 270

Pro Thr Leu Leu Asn Val Gly Gln Thr Ile Thr Asn Glu Met Arg Asn
        275                 280                 285

Glu Leu Asp His Asp Gly Tyr Arg Lys Ile Thr Gly Trp Leu Arg Ala
    290                 295                 300

Val Ala Asp Glu Phe Pro Glu Gly Asp Pro Gln Leu Asp Gly Lys Ala
305                 310                 315                 320

Leu Arg Glu Asn Thr Glu Lys Asp Leu Lys Ile Glu Ile Pro Thr Leu
                325                 330                 335

```
Val Leu Pro Gly Lys Asp Thr Ser Pro Lys Glu Met Ser Val Lys Pro
                340                 345                 350

Thr Ala Pro Gln Asp Lys Ser Val Ser Arg Asp Ala Phe Leu Lys Tyr
            355                 360                 365

Val Lys Asp Asn Glu Ser Thr Leu Ile Pro Asp Val Phe Lys Asp Gln
        370                 375                 380

Glu Asp Val Asn Phe Tyr Ala Arg Val Ile Glu Asp Lys Ser His Asp
385                 390                 395                 400

Trp Glu Ser Thr Pro Ala His Val Leu Ile Asn Gln Gly His Met Val
                405                 410                 415

Asp Leu Val Arg Val Lys Gln Pro Pro Glu Ser Phe Leu Gln Arg Tyr
            420                 425                 430

Phe Ser Ser Met Gln Arg Trp Ile Gly Ser Gln Ala Thr Glu Ala Val
        435                 440                 445

Phe Gly Ile Gln Arg Gln Phe Phe His Ala Thr Tyr Glu Val Val Ala
    450                 455                 460

Gly Phe Asp Ser Asp Asn Lys Glu Pro His Leu Val Val Ser Gly Leu
465                 470                 475                 480

Gly Arg Tyr Val Ile Gly Glu Asp Gly Gln Pro Ile Arg Glu Ala Pro
                485                 490                 495

Lys Lys Gly Gln Lys Glu Gly Asp Leu Lys Val Phe Pro Gln Thr Tyr
            500                 505                 510

Lys Leu Lys Glu Asn Glu Arg Leu Met Arg Val Asp Glu Phe Leu Lys
        515                 520                 525

Leu Pro Glu Ile Gln Asn Thr Phe Pro Gly Ser Gly Lys His Leu Gln
    530                 535                 540

Gly Gly Met Pro Gly Met Asn Glu Met Asp Tyr Trp Asn Arg Leu Asn
545                 550                 555                 560

Ser Leu Asn Arg Ala Arg Cys Glu Asn Asp Val Asp Phe Cys Leu Lys
                565                 570                 575

Gln Leu Gln Thr Ala His Asp Lys Ala Lys Ile Glu Pro Ile Lys Gln
            580                 585                 590

Ala Phe Gln Ser Ser Lys Gly Lys Glu Arg Arg Gln Pro Asn Val Asp
        595                 600                 605

Glu Ile Ala Ala Ala Arg Ile Ile Gln Gln Ile Leu Ala Asn Pro Asp
    610                 615                 620

Cys Ile His Asp Asp His Val Leu Ile Asn Gly Gln Lys Leu Glu Gln
625                 630                 635                 640

Gln Phe Phe Arg Asp Leu Leu Ala Lys Cys Glu Met Ala Val Val Gly
                645                 650                 655

Ser Leu Leu Asn Asp Thr Asp Ile Gly Asn Ile Asp Thr Leu Met Arg
            660                 665                 670

His Glu Lys Asp Thr Glu Phe His Ser Thr Asn Pro Glu Ala Val Pro
        675                 680                 685

Val Lys Ile Gly Glu Tyr Trp Ile Asn Asp Gln Arg Ile Asn Asn Ser
    690                 695                 700

Ser Gly Asn Ile Thr Gln Lys Lys His Asp Leu Ile Phe Leu Met Gln
705                 710                 715                 720

Asn Asp Ala Trp Tyr Phe Ser Arg Val Asn Ala Ile Ala Gln Asn Arg
                725                 730                 735

Asp Lys Gly Ser Thr Phe Lys Glu Val Leu Ile Thr Thr Leu Met Thr
            740                 745                 750
```

```
Pro Leu Thr Ser Lys Ala Leu Val Asp Thr Ser Gln Ala Lys Pro Pro
            755                 760                 765
Thr Arg Leu Phe Arg Gly Leu Asn Leu Ser Glu Glu Phe Thr Lys Gly
    770                 775                 780
Leu Ile Asp Gln Ala Asn Ala Met Ile Ala Asn Thr Thr Glu Arg Leu
785                 790                 795                 800
Phe Thr Asp His Ser Pro Glu Ala Phe Lys Gln Ile Lys Leu Asn Asp
                805                 810                 815
Leu Ser Lys Met Ser Gly Arg Thr Asn Ala Ser Thr Thr Thr Glu Ile
                820                 825                 830
Lys Leu Val Lys Glu Thr Trp Asp Ser Asn Val Ile Phe Glu Met Leu
                835                 840                 845
Asp Pro Asp Gly Leu Leu His Ser Lys Gln Val Gly Arg His Gly Glu
850                 855                 860
Gly Thr Ala Ser Ala Phe Ser Val Tyr Leu Pro Glu Asp Val Ala Leu
865                 870                 875                 880
Val Pro Val Lys Val Thr Leu Asp Gly Lys Thr Gln Lys Gly Glu Asn
                885                 890                 895
Arg Tyr Val Phe Thr Phe Val Ala Val Lys Ser Pro Asp Phe Thr Pro
            900                 905                 910
Arg His Glu Ser Gly Tyr Ala Val Glu Pro Phe Leu Arg Met Gln Ala
            915                 920                 925
Ala Lys Leu Ala Glu Val Lys Ser Ser Ile Glu Lys Ala Gln Arg Ala
            930                 935                 940
Pro Asp Leu Glu Thr Ile Phe Asn Leu Gln Asn Glu Val Glu Ala Val
945                 950                 955                 960
Gln Tyr Ser His Leu Ser Thr Gly Tyr Lys Asn Phe Leu Lys Asn Thr
                965                 970                 975
Val Gly Pro Val Leu Glu Asn Ser Leu Ser Gly Leu Met Glu Ser Asp
                980                 985                 990
Thr Asp Thr Leu Ser Lys Ala Leu Ala Ala Phe Pro Ser Asp Thr Gln
            995                 1000                1005
Trp Ser Ala Phe Asn Phe Glu Glu Ala Arg Gln Ala Lys Arg Gln
        1010                1015                1020
Met Asp Ala Ile Lys Gln Met Val Gly Asn Lys Val Val Leu Asp
        1025                1030                1035
Ala Leu Thr Gln Cys Gln Asp Ala Leu Glu Lys Gln Asn Ile Ala
        1040                1045                1050
Gly Ala Leu Asp Ala Leu Lys Lys Ile Pro Ser Glu Lys Glu Met
        1055                1060                1065
Gly Thr Ile Arg Arg Glu Leu Arg Glu Gln Ile Gln Ser Ala Arg
        1070                1075                1080
Gln Glu Leu Glu Ser Leu Gln Arg Ala Val Val Thr Pro Val Val
        1085                1090                1095
Thr Asp Glu Lys Lys Val Arg Glu Arg Tyr Asp Ala Leu Ile Glu
        1100                1105                1110
Asn Thr Ser Lys Lys Ile Thr Glu Leu Glu Thr Gly Lys Leu Pro
        1115                1120                1125
Asn Leu Asp Ala Val Lys Lys Gly Ile Ser Asn Leu Ser Asn Leu
        1130                1135                1140
Lys Gln Glu Val Thr Val Leu Arg Asn Glu Lys Ile Arg Met His
        1145                1150                1155
Val Gly Thr Asp Lys Val Asp Phe Ser Asp Val Glu Lys Leu Glu
```

```
            1160                1165                1170

Gln Gln Ile Gln Val Ile Asp Thr Lys Leu Ala Asp Ala Tyr Leu
    1175                1180                1185

Leu Glu Val Thr Lys Gln Ile Ser Ala Leu Asp Asn Thr Lys Pro
    1190                1195                1200

Lys Asn Gln Thr Glu Leu Lys Thr Lys Ile Ala Ala Phe Leu Asp
    1205                1210                1215

Arg Thr Thr Asp Ile Glu Met Leu Arg Asn Glu Arg Ile Lys Lys
    1220                1225                1230

His Gly Ser Ser Lys Asp Pro Leu Asp Leu Ser Asp Leu Asp Lys
    1235                1240                1245

Leu Ser Gly Ser Leu Gln Arg Ile Asn Gln Ser Leu Val Ser Asp
    1250                1255                1260

Leu Ile Thr Thr Ile Arg Val Ser Ile Asn Gln Met Glu Ala Lys
    1265                1270                1275

Thr Phe His Glu Gln Glu Lys Glu Ile Gln Gln Asn Phe Glu Leu
    1280                1285                1290

Leu Ala Lys Leu Glu Lys Thr Leu Asp Lys Ser Lys Thr Ser Glu
    1295                1300                1305

Lys Leu Arg Glu Asp Ile Pro Lys Leu Asn Asp Leu Leu Val Ala
    1310                1315                1320

Lys Gln Lys Ala Tyr Pro Gln Met Val Gln Met Gln Leu Lys Ser
    1325                1330                1335

Glu Val Phe Val Thr Gln Leu Arg Glu Val Cys Gln Ala Asn His
    1340                1345                1350

Asp Asp Leu Asp Lys Thr Arg Asn Ala Arg Leu Arg Glu Leu Asp
    1355                1360                1365

Arg Leu Asp Arg Glu Ala Gly Ile Thr Arg Met Val Gly Asn Leu
    1370                1375                1380

Ile Trp Gly Leu Thr Asn Lys Val Gly Leu Thr Thr Asp Glu Arg
    1385                1390                1395

Leu Asp Ile Arg Thr Lys Gln Gln Ser Leu Ala Arg Phe Lys Asn
    1400                1405                1410

Glu Leu Phe Asn Asp Lys Ile Asp Thr Asp Gln Leu Ile Ser Asn
    1415                1420                1425

Leu Ala Arg Lys Arg Pro Ser Glu Leu Gln Glu Gly Leu Gly Ile
    1430                1435                1440

Ser Thr Asp Asn Ala Met Glu Leu His Leu Leu Leu Thr Glu Leu
    1445                1450                1455

Ala Gly Lys Thr Thr Ser Pro Asp Glu Leu Glu Arg Met Lys
    1460                1465                1470

Ala Ile Asp Asp Ile Ser Thr Lys Ile Gly Arg Glu Pro Glu His
    1475                1480                1485

Leu Lys Phe Val Met Val Glu Glu Asp Glu Ser Asn Lys Lys Thr
    1490                1495                1500

Ile Gly Phe
    1505

<210> SEQ ID NO 9
<211> LENGTH: 1926
<212> TYPE: PRT
<213> ORGANISM: artificial
<220> FEATURE:
<223> OTHER INFORMATION: SdeB mutant E/A
```

<400> SEQUENCE: 9

```
Met Gly Glu Ser Lys Met Pro Lys Tyr Val Glu Gly Val Glu Leu Thr
1               5                   10                  15

Gln Glu Gly Met His Ala Ile Phe Ala Arg Met Gly His Pro Glu Ile
            20                  25                  30

Lys Ser Gly Thr Ile Tyr Asn Gly Val Pro Thr Ile Asp Gln Glu Ala
        35                  40                  45

Leu Asp Lys Gln Gly Phe Met Pro Val Leu Thr Gly Val Gly Pro Lys
    50                  55                  60

Arg Asp Ser Gly His Trp Ile Met Leu Ile Lys Gly Ser Gly Asn Gln
65                  70                  75                  80

Tyr His Leu Phe Asp Pro Met Gly Lys Ile Ser Gly Glu Gly Tyr Gln
                85                  90                  95

Asp Ile Leu Ala Thr Gln Leu Pro Lys Gly Ser Thr Leu Ser Val Ile
            100                 105                 110

Pro Asn Glu Pro Gly Leu Asn Lys Gly Leu Cys Gly Tyr Trp Val Ala
        115                 120                 125

Ser Val Gly Leu Lys Ala Cys Ser Ala Leu Asn Lys Asp Asn Pro Pro
    130                 135                 140

Asn Leu Glu Thr Leu Gly Gln Ile Thr Thr Asp Ala Met Lys Asp Glu
145                 150                 155                 160

Leu Thr Asp Asn Gly Tyr Leu Lys Ile Thr Gly Trp Leu Lys Ala Val
                165                 170                 175

Ala Asp Lys Phe Pro Glu Gly Asp Pro Gln Pro Asp Ala Lys Ala Leu
            180                 185                 190

Arg Gln Thr Thr Glu Lys Asp Leu His Ile Glu Ile Pro Ser Pro Val
        195                 200                 205

Ser Pro Val Lys Asp Thr Ala Pro Lys Glu Val Ser Thr Lys Pro Thr
    210                 215                 220

Ala Pro Gln Val Ala Pro Lys Tyr Ser Leu Asp Ser Lys Leu Leu Glu
225                 230                 235                 240

Asn Asp Asp Asp Val Leu Asp Thr Ile Lys Tyr Val His Lys Glu Tyr
                245                 250                 255

Leu Gly Lys Pro Tyr Pro Gly Pro Leu Lys Asn Pro Lys Ala Pro Glu
            260                 265                 270

Glu Gly Arg Leu Pro Pro Asn Glu Gly Pro Asp Arg Gly Pro His Gly
        275                 280                 285

Leu Ala His Thr Val Arg Thr Met Ala Cys Ala Glu Val Met Ile Glu
    290                 295                 300

Glu Ala Arg Lys Ala Gln Leu Arg Gly Glu Thr Leu Gly Lys Ala Lys
305                 310                 315                 320

Asn Gly Gln Thr Leu Ala Asp Val Thr Pro Glu Glu Leu Lys Lys Ile
                325                 330                 335

Leu Ile Ala Gln Ala Phe Phe Val Gly Arg Asp Asp Glu Arg Ser
            340                 345                 350

Gly Tyr Asp Asp Val His Lys Arg Asn Phe Tyr Ala Glu Tyr His Glu
        355                 360                 365

Lys Ser Glu Gln Ala Phe Arg Lys Tyr Val Asp Asn Lys Leu Ile
    370                 375                 380

Gly Lys Ile Phe Lys Asp Gln Lys Glu Val Asp Phe Tyr Ala Ala Ile
385                 390                 395                 400

Ile Leu Asp Lys Asn His Glu Trp Asp Ala Thr Pro Ala His Ile Leu
                405                 410                 415
```

-continued

```
Ile Asn Gln Gly His Met Val Asp Leu Met Arg Thr Lys Ala Pro Ala
            420                 425                 430

Glu Val Ala Leu Glu Arg Thr Tyr Asn Thr Leu Lys Gly Thr Val Gly
            435                 440                 445

Ser Lys Gly Ala Glu Val Val Leu Lys Ala His Arg Asp Phe Phe Phe
    450                 455                 460

Ala Thr Gly Ala Val Val Pro Leu Val Asn Pro Glu Ala Ile Asp Asp
465                 470                 475                 480

Pro Ser Arg Gly Gly Pro Tyr Glu Asn Pro Tyr Ser Gly Glu Lys Phe
                485                 490                 495

Val Ile Val Asp Asp Lys Val Pro Ala Ser Lys Asp Leu Pro Lys
                    500                 505                 510

Ala Val Asn Arg Asp Tyr Lys Leu Lys Asp Asn Glu Arg Phe Leu Thr
            515                 520                 525

Ile Lys Glu Tyr Tyr Ala Phe Pro Asp Val Gln Gln Thr Tyr Pro Gly
        530                 535                 540

Tyr Lys Thr Arg Leu Glu Ala Ser Ser Tyr Tyr Phe Pro Thr Pro Phe
545                 550                 555                 560

Ala Gly Glu Cys Glu Gln Asn Pro Ala Lys Cys Leu Gly Ala Ile Gln
                565                 570                 575

Lys Ala Arg Ser Lys Leu Gln Thr Asp Ala Ile Lys Asn Gly Phe Gln
                580                 585                 590

Ser Ser Ser Glu Lys Glu Arg Arg Gln Pro Asn Met Asp Glu Ile Ala
            595                 600                 605

Ala Ala Arg Ile Ile Gln Gln Ile Met Ala Asn Pro Asp Cys Ile His
            610                 615                 620

Asp Asp His Val Leu Ile Asn Gly Gln Lys Leu Glu Glu Lys Phe Phe
625                 630                 635                 640

Arg Asp Leu Leu Ala Lys Cys Asp Met Ala Val Val Gly Ser Leu Leu
                645                 650                 655

Asn Asp Thr Asp Ile Lys Asn Ile Asp Thr Leu Met Arg His Glu Lys
            660                 665                 670

Asn Thr Glu Phe His Ser Thr Asp Pro Lys Ala Val Pro Val Lys Ile
        675                 680                 685

Gly Asp Ala Trp Glu Asn Arg Ile Arg Thr Lys Gly Gly Asp Val Thr
    690                 695                 700

Gln Met Lys His Asp Leu Ile Phe Leu Met Gln Asn Asp Ala Trp Tyr
705                 710                 715                 720

Phe Ser Arg Val Asn Ala Ile Ala Gln Asn Arg Asp Lys Gly Ser Asn
                725                 730                 735

Phe Lys Glu Val Leu Phe Thr Thr Leu Met Thr Pro Leu Thr Asn Lys
            740                 745                 750

Ser Leu Ile Asp Thr Ser His Val Pro Ala Pro Lys Lys Leu Tyr Arg
        755                 760                 765

Gly Leu Asn Leu Pro Gln Glu Phe Thr Asn Lys Leu Ile Asn Gln Ser
    770                 775                 780

Asn Ala Ile Ile Ala Asn Thr Glu Asn Thr Leu Phe Thr Asp Leu Ser
785                 790                 795                 800

Ala Glu Ala Phe Lys Gln Ile Lys Leu Asn Asp Phe Ser Gln Met Ser
                805                 810                 815

Gly Lys Thr Cys Ala Ser Thr Thr Lys Asn Met Lys Leu Leu Thr Asp
            820                 825                 830
```

-continued

```
Ile Trp Gly Ser Asn Val Ile Phe Glu Met Leu Asp Pro Asp Gly Leu
            835                 840                 845

Leu His Pro Lys Gln Val Gly Thr His Met Thr Gly Ser Ala Asp Ala
850                 855                 860

Phe Ser Val Tyr Leu Pro Glu Asp Val Ala Leu Val Pro Thr Lys Val
865                 870                 875                 880

Thr Leu Glu Gly Lys Thr Asp Thr Gly Glu Asp Arg Tyr Ile Phe Thr
                885                 890                 895

Leu Val Ala Val Lys Ser Pro Asp Phe Ile Pro Arg His Glu Ser Gly
                900                 905                 910

Tyr Ala Val Glu Pro Phe Met Lys Met Gln Lys Glu Lys Val Thr Gln
                915                 920                 925

Ala Leu Asp Ala Ile Glu Lys Asp Lys Asp Ser Tyr Asn Ile Asp Glu
930                 935                 940

Gln Leu Lys Ser Leu Arg Thr Glu Met Val Arg Gln Ala Lys Leu Pro
945                 950                 955                 960

Leu Arg Glu Gly Val Phe Asp Arg Leu Ser His Arg Phe Ser Leu Glu
                965                 970                 975

Thr Ser Asp Asn Lys Ile Ser Pro Glu Arg Arg Asp Phe Leu Asn Gln
                980                 985                 990

His Val Ile Pro Val Leu Gln Glu Cys His Ile Ala Leu Arg Thr Asn
            995                 1000                1005

Asn Met Glu Met Met Gln Lys Ala Leu Ala Lys Phe Pro Thr Asp
    1010                1015                1020

Lys Gln Trp Ser Ala Phe Lys Ser Gly Glu Ala Val Arg Ala Lys
    1025                1030                1035

Ala Gln Met Asp Val Leu Lys Gln Gln Ile Glu Lys Lys Ile Met
    1040                1045                1050

Leu Gln Thr Gln Ile Ile Pro Ala Leu Thr Glu Cys Gly Glu Ala
    1055                1060                1065

Leu Asp Lys Gln Asn Val Thr Glu Ala Leu Gln Ala Leu Asn Lys
    1070                1075                1080

Leu Pro Ala Glu Lys Glu Ile Gly Lys Ala Lys Gly Ile Gly Gln
    1085                1090                1095

Glu Leu Arg Gly Gln Ile Val Gly Val Lys Gln Glu Leu Thr Gly
    1100                1105                1110

Asn Leu Glu Ser Leu Gln Arg Ala Val Thr Thr Pro Val Val Lys
    1115                1120                1125

Asp Ala Glu Lys Met Arg Val Arg Tyr Glu Thr Leu Leu Thr Asp
    1130                1135                1140

Val Thr Lys Arg Val Thr Asp Phe Glu Lys Ile Lys Pro Ala Asn
    1145                1150                1155

Leu Asp Gly Tyr Asn Lys Ala Ile Ala Asp Leu Asn Asn Ile Gln
    1160                1165                1170

Gln Glu Leu Asn Leu Leu Arg Asn Glu Lys Ile Arg Met His Thr
    1175                1180                1185

Asp Lys Asp Lys Ala Val Asp Phe Ser Asp Ile Glu Ala Leu Glu
    1190                1195                1200

Lys Arg Leu Lys Glu Ala Gln Pro Asn Leu Tyr Pro Ser Leu Val
    1205                1210                1215

Glu Gly Thr Thr Lys Gly Ile Gln Glu Leu Glu Lys Ile Pro Lys
    1220                1225                1230

Ser Ile Ser Phe Asp Asp Val Lys Ser Met Thr Ser Lys Ile Asn
```

```
                1235                1240                1245
Gly Tyr Leu Glu Thr Leu Glu Phe Ile Arg Asn Glu Arg Val Lys
    1250                1255                1260
Lys His Gly Glu Ser Thr Glu Pro Leu Asp Met Ser Asp Leu Asp
    1265                1270                1275
Lys Leu Lys Asn Gln Leu Gln Gly Val Ser Gln His Leu Ala Gln
    1280                1285                1290
Ile Leu Leu Asn Gly Ala Lys Asn Ser Leu Asp Lys Ile Lys Asp
    1295                1300                1305
Pro Val Thr Leu Glu Lys Glu Gly Gln Tyr Ile Lys Arg Cys Leu
    1310                1315                1320
Asp His Phe Ala Glu Leu Glu Lys Thr Leu Asp Ser Ser Val Lys
    1325                1330                1335
Gly Met Lys Gln Lys Glu Asp Phe Asn Thr Tyr Lys Asn Ser Leu
    1340                1345                1350
Met Glu Lys Gln Glu Lys Ala Tyr Pro Glu Met Leu Gln Leu Gln
    1355                1360                1365
Tyr Lys Ser Glu Ala Leu Ile Thr Gln Leu Arg Asn Leu Cys Asn
    1370                1375                1380
Ile His His Asp Asn Leu Ala Lys Thr Arg Glu Glu Gln Gln Gln
    1385                1390                1395
Leu Leu Asn Lys Thr Gly Gly Ile Leu Gly Gly Phe Phe Ser Gln
    1400                1405                1410
Ile Thr Thr Ala Ile Ser Gln Ala Glu Ser Lys Lys Ala Asn Glu
    1415                1420                1425
Phe Ala Arg Phe Lys Thr Glu Leu Asn Asn Asp Lys Ser Asp Val
    1430                1435                1440
Ser Gln Leu Ile Gln Phe Leu Val Lys Lys Pro Ser Glu Leu
    1445                1450                1455
Glu Glu Asn Leu Gly Ile Ser Lys Glu Asn Ala Glu Gln Leu His
    1460                1465                1470
Gly Leu Leu Lys Gln Leu Asp Ala Lys Ala Thr Pro Ile Asp Lys
    1475                1480                1485
Leu Gln Glu Asn Thr Arg Leu Ile Asp Glu Ile Ser Thr Lys Met
    1490                1495                1500
Gly Ser Lys Pro Val Ser Pro Glu His Val Ala Ala Thr Lys Ala
    1505                1510                1515
Arg Glu Tyr Tyr Gln Phe Leu Leu Tyr Gly Ala Thr Gln Lys Ile
    1520                1525                1530
Gly Asn Phe Glu Lys Ile Lys Pro Ile Asp Pro Glu Ser Tyr Lys
    1535                1540                1545
Lys Ala Met Ser Asp Leu Asn Asn Met Gln Glu Ala Leu Gln Phe
    1550                1555                1560
Leu Arg Ser Glu Lys Ser Arg Ile His Asp Gly Lys Glu Lys Ala
    1565                1570                1575
Val Glu Phe Ser Asp Ile Glu Ala Leu Glu Lys Arg Val Gln Asn
    1580                1585                1590
Ala Gln Pro Lys Leu Leu Thr Ala Leu Leu Asp Lys Thr Thr Arg
    1595                1600                1605
Glu Ile Ser Ala Leu Val Lys Ile Pro Arg Lys Leu Thr Phe Glu
    1610                1615                1620
Asp Ile Lys Ser Met Thr Thr Lys Leu Asn Ser Tyr Leu Glu Thr
    1625                1630                1635
```

-continued

```
Leu Glu Leu Ile Arg Asn Glu Arg Ile Lys Gln His Gly Lys Ser
    1640                1645                1650

Pro Glu Leu Leu Asp Met Ser Asp Leu Asp Ser Leu Lys Gly Gln
    1655                1660                1665

Leu Gln Thr Phe Asn Gln Asn Leu Thr Gly Met Ile Leu Asn Ala
    1670                1675                1680

Thr Lys Asp Gly Leu Asp Arg Ile Asn Asp Arg Ala Asn Phe Lys
    1685                1690                1695

Glu Gly Glu Pro Tyr Val Lys Ala Cys Leu Asp Leu Leu Thr Glu
    1700                1705                1710

Leu Glu Lys Thr Leu Asp Ser Ser Val Lys Gly Met Lys Gln Lys
    1715                1720                1725

Glu Asp Ile Ser Ala Cys Arg Asn Ser Leu Leu Asp Lys Gln Glu
    1730                1735                1740

Lys Ala Asn Ser Gly Met Leu Asp Leu Gln Ser Lys Ser Lys Asp
    1745                1750                1755

Leu Val Thr Gln Leu Arg Asp Ile Cys Lys Ile His His Gly Asn
    1760                1765                1770

Leu Ala Glu Ala Arg Arg Thr Arg Leu His Ser Leu Asp Asn Gln
    1775                1780                1785

Glu Gly Gly Leu Leu Gly Gly Leu Trp Ser Val Thr Asn Lys Leu
    1790                1795                1800

Gly Val Thr Thr Asp Thr Val Gly Ile Glu Arg Met Gln Ile Lys
    1805                1810                1815

Met Lys Glu Gln Ala Leu Ala Arg Phe Lys Thr Glu Leu Asn Asn
    1820                1825                1830

Asp Lys Tyr Asp Thr Asn Gln Val Ile Ala Phe Leu Ala Asn Lys
    1835                1840                1845

Lys Pro Ser Glu Leu Glu Glu Gly Leu Gly Ile Ser Lys Glu Asn
    1850                1855                1860

Ala Glu Glu Leu His Gly Leu Leu Ser Lys Leu Thr Ser Lys Met
    1865                1870                1875

Thr Ser Lys Ile Glu Ile Glu Glu Asn Thr Gln Leu Ile Asp Glu
    1880                1885                1890

Ile Ser Thr Lys Ile Gly Thr Glu Pro Val Lys Leu Glu Ser Thr
    1895                1900                1905

His Thr Val Asp Glu Asp Glu Arg Asp Thr Tyr His Arg Glu Ser
    1910                1915                1920

Gly Tyr Phe
    1925

<210> SEQ ID NO 10
<211> LENGTH: 1533
<212> TYPE: PRT
<213> ORGANISM: artificial
<220> FEATURE:
<223> OTHER INFORMATION: mutant SdeC E/A

<400> SEQUENCE: 10

Met Pro Lys Tyr Val Glu Gly Val Glu Leu Thr Gln Glu Gly Met His
1               5                   10                  15

Ala Ile Phe Ala Arg Met Gly His Gly Asp Ile Thr Ser Gly Ser Ile
                20                  25                  30

Tyr Asn Gly Val Pro Thr Ile Asp Thr Glu Ala Leu Asn Arg Gln Gly
            35                  40                  45
```

```
Phe Met Pro Val Leu Thr Gly Val Gly Pro Arg Arg Asp Ser Gly His
    50              55                  60

Trp Ile Met Leu Ile Lys Gly Pro Gly Asn Gln Tyr Phe Leu Phe Asp
65                  70                  75                  80

Pro Leu Gly Lys Thr Ser Gly Glu Gly Tyr Lys Asn Thr Leu Leu Ala
                85                  90                  95

Gln Leu Pro Ile Ala Ser Thr Leu Ser Val Ile Pro Asn Glu Pro Gly
                100                 105                 110

Leu Asn Lys Gly Leu Cys Gly Tyr Trp Val Ala Ser Val Gly Leu Lys
            115                 120                 125

Ala Arg Ser Glu Leu Ser Lys Asp Asn Pro Pro Asn Leu Glu Thr Leu
            130                 135                 140

Gly Gln Ile Thr Thr Asp Ala Met Lys Asp Glu Leu Thr Asp Asn Gly
145                 150                 155                 160

Tyr Leu Lys Ile Thr Gly Trp Leu Lys Ala Val Ala Asp Lys Phe Pro
                165                 170                 175

Glu Gly Asp Pro Gln Pro Asp Ala Lys Ala Leu Arg Gln Thr Thr Glu
                180                 185                 190

Lys Asp Leu His Ile Glu Ile Pro Ser Pro Val Ser Pro Ile Lys Asp
            195                 200                 205

Thr Ala Pro Lys Glu Val Ser Thr Lys Pro Thr Ala Pro Gln Val Ala
210                 215                 220

Pro Lys His Ser Leu Asp Ser Lys Leu Leu Glu Asn Asp Asp Asp Val
225                 230                 235                 240

Leu Asp Thr Ile Lys Tyr Val His Lys Glu Tyr Leu Gly Lys Pro Tyr
                245                 250                 255

Pro Gly Pro Leu Lys Asn Pro Lys Ala Pro Glu Glu Gly Arg Leu Pro
                260                 265                 270

Pro Asn Glu Gly Pro Asp Arg Gly Pro His Gly Leu Ala His Thr Val
            275                 280                 285

Arg Thr Met Ala Cys Ala Glu Val Met Ile Glu Glu Ala Arg Lys Ala
        290                 295                 300

Gln Leu Arg Gly Glu Thr Leu Gly Lys Ala Lys Asn Gly Gln Thr Leu
305                 310                 315                 320

Ala Asp Val Thr Pro Glu Glu Leu Lys Lys Ile Leu Ile Ala Gln Ala
                325                 330                 335

Phe Phe Val Val Gly Arg Asp Asp Glu Arg Ser Gly Tyr Asp Asp Val
                340                 345                 350

His Lys Arg Asn Phe Tyr Ala Glu Tyr His Glu Lys Ser Glu Gln Ala
            355                 360                 365

Phe Arg Lys Tyr Val Glu Asp Asn Lys Leu Ile Gly Lys Ile Phe Lys
            370                 375                 380

Asp Gln Lys Glu Val Asp Phe Tyr Ala Ala Ile Ile Leu Asp Lys Asn
385                 390                 395                 400

His Glu Trp Asp Ala Thr Pro Ala His Ile Leu Ile Asn Gln Gly His
                405                 410                 415

Met Val Asp Leu Met Arg Thr Lys Ala Pro Ala Glu Val Ala Leu Glu
            420                 425                 430

Arg Thr Tyr Asn Thr Leu Lys Gly Thr Val Gly Ser Lys Gly Ala Glu
            435                 440                 445

Val Val Leu Lys Ala His Arg Asp Phe Phe Ala Thr Gly Ala Val
450                 455                 460
```

-continued

```
Val Pro Leu Val Asn Pro Glu Ala Ile Asp Asp Ser Arg Gly Gly
465                 470                 475                 480

Pro Tyr Glu Asn Pro Tyr Ser Gly Glu Lys Phe Val Ile Val Asp Asp
                485                 490                 495

Lys Val Pro Ala Ser Lys Lys Asp Leu Pro Lys Ala Val Asn Arg Asp
            500                 505                 510

Tyr Lys Leu Lys Asp Asn Glu Arg Phe Leu Thr Ile Lys Glu Tyr Tyr
        515                 520                 525

Ala Phe Pro Asp Val Gln Gln Thr Tyr Pro Gly Tyr Lys Thr Arg Leu
    530                 535                 540

Glu Ala Ser Ser Tyr Tyr Phe Pro Thr Pro Phe Ala Gly Glu Cys Glu
545                 550                 555                 560

Gln Asn Pro Ala Lys Cys Leu Gly Ala Ile Gln Lys Ala Arg Ser Lys
                565                 570                 575

Leu Gln Thr Asp Ala Ile Lys Asn Gly Phe Gln Ser Ser Glu Lys
                580                 585                 590

Glu Arg Arg Gln Pro Asn Met Asp Glu Ile Ala Ala Arg Ile Ile
        595                 600                 605

Gln Gln Ile Met Ala Asn Pro Asp Cys Ile His Asp Asp His Val Leu
    610                 615                 620

Ile Asn Gly Gln Lys Leu Glu Glu Lys Phe Phe Arg Asp Leu Leu Ala
625                 630                 635                 640

Lys Cys Asp Met Ala Val Val Gly Ser Leu Leu Asn Asp Thr Asp Ile
                645                 650                 655

Lys Asn Ile Asp Thr Leu Met Arg His Glu Lys Asn Thr Glu Phe His
            660                 665                 670

Ser Thr Asp Pro Lys Ala Val Pro Val Lys Ile Gly Asp Ala Trp Glu
        675                 680                 685

Asn Arg Ile Arg Thr Lys Gly Gly Asp Val Thr Gln Met Lys His Asp
    690                 695                 700

Leu Ile Phe Leu Met Gln Asn Asp Ala Trp Tyr Phe Ser Arg Val Asn
705                 710                 715                 720

Ala Ile Ala Gln Asn Arg Asp Lys Gly Ser Asn Phe Lys Glu Val Leu
                725                 730                 735

Phe Thr Thr Leu Met Thr Pro Leu Thr Asn Lys Ser Leu Ile Asp Thr
            740                 745                 750

Ser His Val Pro Ala Pro Lys Lys Leu Tyr Arg Gly Leu Asn Leu Pro
        755                 760                 765

Gln Glu Phe Thr Asn Lys Leu Ile Asn Gln Ser Asn Ala Ile Ile Ala
    770                 775                 780

Asn Thr Glu Asn Thr Leu Phe Thr Asp Leu Ser Ala Glu Ala Phe Lys
785                 790                 795                 800

Gln Ile Lys Leu Asn Asp Phe Ser Gln Met Ser Gly Lys Thr Cys Ala
                805                 810                 815

Ser Thr Thr Lys Asn Met Lys Leu Leu Thr Asp Ile Trp Gly Ser Asn
            820                 825                 830

Val Ile Phe Glu Met Leu Asp Pro Asp Gly Leu Leu His Pro Lys Gln
        835                 840                 845

Val Gly Thr His Met Ala Gly Ser Ala Asp Ala Phe Ser Val Tyr Leu
    850                 855                 860

Pro Glu Asp Val Ala Leu Val Pro Thr Lys Val Thr Leu Glu Gly Lys
865                 870                 875                 880

Thr Asp Thr Gly Glu Asp Arg Tyr Ile Phe Thr Leu Val Ala Val Lys
```

|  |  |  |  | 885 |  |  |  |  | 890 |  |  |  |  | 895 |  |
|---|---|---|---|---|---|---|---|---|---|---|---|---|---|---|---|

Ser Pro Asp Phe Ile Pro Arg His Glu Ser Gly Tyr Ala Val Glu Pro
                900                905              910

Phe Met Lys Met Gln Lys Glu Lys Val Thr Gln Ala Leu Asp Ala Ile
                915                920              925

Glu Lys Asp Lys Asp Ser Tyr Asn Ile Asp Glu Gln Leu Lys Ser Leu
                930                935              940

Arg Thr Glu Met Val Arg Gln Ala Lys Leu Pro Leu Arg Glu Gly Val
945                950                955              960

Phe Asp Arg Leu Ser His Arg Leu Ser Leu Glu Thr Ser Asp Asn Lys
                965                970              975

Ile Ser Pro Glu Arg Arg Asp Phe Leu Asn Gln His Val Ile Pro Val
                980                985              990

Leu Gln Glu Cys His Ile Ala Leu Arg Ala Asn Asp Met Asp Met Met
                995               1000            1005

Gln Lys Ala Leu Ala Lys Phe Pro Thr Asp Lys Gln Trp Ser Ala
1010               1015               1020

Phe Lys Ser Gly Glu Ala Val Arg Ala Lys Ala Gln Met Asp Val
1025               1030               1035

Leu Lys Gln Gln Ile Glu Lys Lys Ile Met Leu Gln Thr Gln Ile
1040               1045               1050

Ile Pro Ala Leu Thr Glu Cys Gly Glu Ala Leu Asp Lys Gln Asn
1055               1060               1065

Val Thr Glu Ala Leu Gln Ala Leu Asn Lys Leu Pro Ala Glu Lys
1070               1075               1080

Glu Ile Gly Lys Val Lys Thr Ile Gly Gln Glu Leu Arg Gly Gln
1085               1090               1095

Ile Val Gly Val Lys Gln Glu Leu Thr Gly Asn Leu Glu Pro Leu
1100               1105               1110

Gln Arg Ala Thr Thr Thr Pro Ile Val Gln Asp Ala Glu Lys Ile
1115               1120               1125

Lys Val Arg Tyr Glu Thr Leu Leu Thr Asp Val Thr Lys Arg Val
1130               1135               1140

Thr Asp Phe Glu Lys Ile Lys Pro Ala Asn Leu Asp Gly Tyr Asn
1145               1150               1155

Lys Ala Ile Ala Asp Leu Asn Asn Ile Gln Gln Glu Leu Asn Leu
1160               1165               1170

Leu Arg Asn Glu Lys Ile Arg Met His Thr Asp Lys Asp Lys Ala
1175               1180               1185

Val Asp Phe Ser Asp Ile Glu Ala Leu Asp Lys Arg Leu Gln Asp
1190               1195               1200

Val Gln Ser Lys Leu Pro Thr Gln Leu Leu Glu Gln Thr Ser Lys
1205               1210               1215

Asp Val Ala Lys Leu Ala Lys Met Pro Glu Lys Ile Thr Phe Asn
1220               1225               1230

Asp Ile Lys Ser Met Thr Ser Lys Met Asn Asn Tyr Leu Glu Thr
1235               1240               1245

Leu Glu Leu Ile Arg Asn Asp Arg Ile Lys His Ala Gly Ser
1250               1255               1260

Thr Asp Pro Leu Asp Met Ser Asp Leu Asp Gly Leu Lys Gly Gln
1265               1270               1275

Leu Gln Thr Tyr Asn Gln Ser Met Ala Asp Ile Leu Leu Arg Ala
1280               1285               1290

-continued

```
Ala Lys Ser Ser Leu Asp Lys Ile Lys Asp Pro Ala Thr Phe Glu
    1295                1300                1305

Lys Glu Ser Pro Tyr Ile Lys Gln Cys Phe Asp His Leu Ala Glu
    1310                1315                1320

Leu Glu Lys Thr Leu Asp Asp Ser Asp Lys Gly Arg Lys Gln Lys
    1325                1330                1335

Glu Asp Phe Thr Ala Tyr Lys Ser Ala Leu Met Asp Lys Gln Glu
    1340                1345                1350

Lys Ala Tyr Pro Glu Met Leu Gln Leu Gln Tyr Lys Ser Glu Ala
    1355                1360                1365

Leu Ile Met Gln Leu Arg Asp Ile Cys Lys Ile His His Asp Asn
    1370                1375                1380

Leu Ala Glu Ala Arg Arg Val Arg Leu Gln Gln Leu Asp Ser Gln
    1385                1390                1395

Gly Gly Gly Leu Leu Gly Gly Leu Trp Ala Val Thr Asn Thr Ile
    1400                1405                1410

Gly Leu Thr Thr Asp Asn Val Asn Ile Glu Lys Met Gln Ile Arg
    1415                1420                1425

Met Lys Glu Gln Thr Leu Arg Ala Phe Lys Thr Glu Leu Thr Asn
    1430                1435                1440

Asp Lys Leu Asn Thr Asp Gln Val Ile Ala Phe Leu Ala Lys Gly
    1445                1450                1455

Ser Pro Ser Glu Leu Gln Glu Ala Leu Gly Ile Ser Lys Glu Asn
    1460                1465                1470

Ala Glu Gln Leu His Gly Leu Leu Lys Gln Leu Glu Ile Lys Thr
    1475                1480                1485

Ala Ser Thr Asp Lys Leu Gln Glu Ile Glu Lys Leu Ile Asp Glu
    1490                1495                1500

Val Ser Thr Lys Ile Gly Lys Glu Pro Val Lys Gln Asp His Thr
    1505                1510                1515

Ile Thr Ile Asp Glu Glu Glu Ser Asp Asp Ile Arg Tyr Gly Phe
    1520                1525                1530
```

<210> SEQ ID NO 11
<211> LENGTH: 1514
<212> TYPE: PRT
<213> ORGANISM: artificial
<220> FEATURE:
<223> OTHER INFORMATION: SidE mutant E/A

<400> SEQUENCE: 11

```
Met Leu Ile Phe Lys Ser Gln Ile Leu Ile Leu Lys Tyr Leu Ser Arg
1               5                   10                  15

Ser Cys Val Met Pro Lys Tyr Val Glu Gly Ile Glu Leu Thr Gln Glu
                20                  25                  30

Gly Met His Ala Ile Phe Glu Arg Met Gly His Pro Asn Ile Thr Ser
                35                  40                  45

Gly Thr Ile Tyr Asn Gly Glu Pro Thr Ile Asp Lys Gly Ala Leu Asp
        50                  55                  60

Arg Gln Gly Phe Met Pro Val Leu Thr Gly Val Ser Pro Arg Gln Asp
65                  70                  75                  80

Ser Gly His Trp Ile Met Leu Ile Lys Gly Gln Gly Asn Gln Tyr Phe
                85                  90                  95

Leu Phe Asp Pro Leu Gly Glu Ser Ser Gly Lys Tyr Tyr Gln Asn Ile
                100                 105                 110
```

```
Leu Ala Lys Lys Leu Pro Gly Ala Thr Leu Ser Val Ile Pro Asn Asn
            115                 120                 125

Ala Gly Leu Asn Met Gly Leu Cys Gly Tyr Trp Val Ala Ser Val Gly
        130                 135                 140

Leu Arg Ala His Ala Ala Leu Thr Gln Pro Ile Pro Pro Ser Leu Arg
145                 150                 155                 160

Asn Leu Gly Gln Thr Ile Thr Gln Glu Met Arg Asp Glu Leu Thr Gln
                165                 170                 175

Asp Gly Ser Glu Lys Ile Thr Gln Trp Leu Arg Ala Val Gly Asn Glu
            180                 185                 190

Phe Pro Asp Gly Asp Ile Gln Pro Asp Ala Thr Ala Leu Arg Arg Ala
        195                 200                 205

Thr Glu Lys Asn Val Arg Ile Asp Glu Phe Gln Pro Val Leu Thr Gly
210                 215                 220

Thr Ser Pro Lys Glu Ile Ser Ile Asn Pro Thr Ala Pro Gln Glu Val
225                 230                 235                 240

Ser Val Pro Thr Trp Asn Gly Phe Ser Leu Tyr Thr Asp Glu Thr Val
                245                 250                 255

Arg Asn Ala Ala Arg Tyr Ala Tyr Asp Asn Tyr Leu Gly Lys Pro Tyr
            260                 265                 270

Thr Gly Thr Val Glu Ala Thr Pro Val Asn Phe Gly Gly Gln Met Val
        275                 280                 285

Tyr Arg Gln His His Gly Leu Ala His Thr Leu Arg Thr Met Ala Tyr
        290                 295                 300

Ala Glu Ile Ile Val Glu Ala Arg Lys Ala Lys Leu Arg Gly Glu
305                 310                 315                 320

Ser Leu Lys Thr Phe Ala Asp Gly Arg Thr Leu Ala Asp Val Thr Pro
                325                 330                 335

Glu Glu Leu Arg Lys Ile Met Ile Ala Gln Ala Phe Phe Val Thr Gly
            340                 345                 350

Arg Asp Asp Glu Glu Ser Ser Lys Asn Tyr Glu Lys Tyr His Glu Gln
        355                 360                 365

Ser Arg Asp Ala Phe Leu Lys Tyr Val Glu Glu Asn Lys Ser Thr Leu
        370                 375                 380

Ile Pro Asp Val Phe Lys Asp Glu Lys Asp Val Lys Phe Tyr Ala Asp
385                 390                 395                 400

Val Ile Glu Asp Lys Asp His Lys Trp Ala Asp Ser Pro Ala His Val
                405                 410                 415

Leu Val Asn Gln Gly His Met Val Asp Leu Val Arg Val Lys Gln Pro
            420                 425                 430

Pro Glu Ser Tyr Leu Glu Tyr Tyr Phe Ser Gln Leu Gln Pro Trp Ile
        435                 440                 445

Gly Ser Thr Ala Thr Glu Ala Val Phe Ala Thr Gln Arg Gln Phe Phe
450                 455                 460

His Ala Thr Tyr Glu Ala Val Ala Gly Phe Asp Ser Glu Asn Lys Glu
465                 470                 475                 480

Pro His Leu Val Val Asp Gly Leu Gly Arg Tyr Val Ile Gly Gln Asp
                485                 490                 495

Gly Asn Pro Ile Arg Glu Glu Ser Asp Asp Glu Asp Glu Glu Glu Ser
            500                 505                 510

Gly Glu Leu Lys Phe Phe Ser Gln Lys Lys Leu Glu Glu Asn Gln
        515                 520                 525
```

```
Arg Tyr Met Arg Val Asp Glu Tyr Leu Lys Leu Asp Glu Val Gln Lys
            530                 535                 540

Arg Phe Pro Gly Ala Gly Lys Lys Leu Asp Gly Gly Leu Pro Gly Leu
545                 550                 555                 560

Lys Glu Tyr Gln Tyr Leu Gln Arg Leu Asn Ser Ile Asn Arg Ala Arg
                    565                 570                 575

Cys Glu Asn Asp Val Asp Phe Cys Leu Gly Gln Leu Gln Thr Ala His
                580                 585                 590

His Gln Thr Lys Ile Thr Pro Ile Lys Arg Ala Phe Gln Ser Ser Ser
            595                 600                 605

Glu Lys Ala Arg Arg Gln Pro Asn Met Asp Glu Ile Ala Ala Ala Arg
            610                 615                 620

Ile Val Gln Gln Ile Met Ala Asn Pro Asp Cys Ile His Asp Asp His
625                 630                 635                 640

Val Phe Leu Asn Gly Gln Lys Leu Glu Glu Lys Phe Phe Arg Asp Leu
                    645                 650                 655

Leu Ala Lys Cys Asp Met Ala Ile Val Gly Ser Leu Leu Asn Asp Thr
                660                 665                 670

Asp Ile Arg Asn Ile Asp Thr Leu Met Gln His Glu Arg Asn Thr Glu
            675                 680                 685

Phe His Ser Thr Asp Ala Lys Ala Lys Pro Val Lys Leu Gly Glu Thr
            690                 695                 700

Trp Glu Lys Thr Ile Arg Ser Gly Gly Gly Val Thr Gln Ile Lys His
705                 710                 715                 720

Asp Leu Ile Phe Leu Met Gln Asn Asp Ala Trp Tyr His Thr Arg Val
                    725                 730                 735

Asn Ala Ile Ala Gln Asn Arg Asp Lys Asp Ser Thr Phe Lys Glu Val
                740                 745                 750

Leu Ile Thr Ala Leu Met Thr Pro Leu Thr Asn Lys Ser Leu Met Asp
            755                 760                 765

Thr Ser Arg Ser Pro Ala Pro Lys Thr Leu Phe Arg Gly Leu Asp Leu
            770                 775                 780

Ser Glu Glu Phe Lys Asn Lys Leu Ile Asn Gln Ala Glu Thr Ile Ile
785                 790                 795                 800

Ala Asn Thr Thr Glu His Leu Phe Thr Asp Leu Ser Thr Glu Ala Phe
                    805                 810                 815

Lys Gln Ile Lys Leu Asn Asp Phe Ser Gln Val Ser Ala Arg Thr Cys
                820                 825                 830

Ala Ser Thr Ser Thr Asn Ile Glu Val Pro Arg Thr Ile Phe Gly Ser
            835                 840                 845

Asn Thr Ile Phe Glu Ile Leu Asp Pro Asp Gly Leu Leu His Pro Lys
850                 855                 860

Gln Val Gly Thr His Val Ser Gly Ser Ala Ser Ala Tyr Ser Ile Tyr
865                 870                 875                 880

Leu Pro Glu Asp Val Ala Leu Val Pro Ile Lys Val Ser Phe Asp Gly
                    885                 890                 895

Lys Thr Gly Lys Gly Lys Asp Arg His Ile Phe Thr Leu Val Ala Val
                900                 905                 910

Lys Ser Pro Asp Phe Thr Pro Arg His Glu Ser Gly Tyr Ala Val Gly
            915                 920                 925

Pro Leu Leu Lys Met Gln Thr Pro Lys Leu Glu Glu Ile Gln Arg Leu
            930                 935                 940

Val Glu Gln Ala Arg Glu Glu Pro Asp Leu Glu Arg Val Phe Asn Leu
```

-continued

```
945              950              955              960
Gln Ser Arg Val Ala Arg Gln Ala Lys Phe Ser Thr Glu Ser Gly Tyr
                965              970              975
Lys Thr Phe Leu Asn Glu Lys Val Ala Pro Val Leu Glu Gln Ser Leu
                980              985              990
Asn Gly Leu Leu Asp Asn Asn Val Thr Ile Leu Gly Lys Val Leu Ser
                995              1000             1005
Ala Phe Pro Ser Asp Gly Gln Trp Ser Ala Phe Asn Ser Val Glu
    1010             1015              1020
Ala Arg Gln Met Lys Ile Gln Met Asp Ala Ile Lys Gln Met Val
    1025             1030              1035
Glu Lys Lys Ala Val Leu Glu Gly Gln Ile Leu Pro Ala Leu Ala
    1040             1045              1050
Gln Cys Gln Asn Ala Leu Glu Lys Gln Asn Ile Ala Gly Ala Leu
    1055             1060              1065
Gln Ala Leu Arg Asn Ile Pro Ser Glu Lys Glu Met Gln Thr Met
    1070             1075              1080
Leu Ser Ile Ser Gly Gly Leu Arg Gly Gln Ile Gln Arg Ala Lys
    1085             1090              1095
Gln Asp Leu Thr Glu Thr Leu Glu Pro Leu Gln Arg Ala Ile Thr
    1100             1105              1110
Ala Lys Leu Val Ser Asp Gln Glu Lys Val Lys Val Arg Tyr Glu
    1115             1120              1125
Lys Leu Ile Ala Gly Ile Pro Gln Gln Ile Ala Asp Leu Glu Lys
    1130             1135              1140
Ala Glu Leu Ala Asp Leu Ala Lys Val Lys Val Val Ser Arg
    1145             1150              1155
Phe Asn His Leu Gln Glu Glu Leu Lys Leu Leu Arg Asn Glu Lys
    1160             1165              1170
Ile Arg Met His Thr Gly Ser Glu Lys Val Asp Phe Ser Asp Ile
    1175             1180              1185
Ala Gln Leu Glu Ala Gln Leu Gln Lys Ile His Thr Lys Leu Tyr
    1190             1195              1200
Asp Ala Tyr Leu Val Glu Leu Thr Lys Glu Ile Ser Ala Leu Val
    1205             1210              1215
Lys Glu Lys Pro Lys Asn Leu Ala Asp Val Lys Arg Met Val Ser
    1220             1225              1230
Asn Phe Tyr Ala Met Ser Ala Asp Ile Glu Gln Leu Arg Gln Glu
    1235             1240              1245
Lys Ile Lys Glu His Gly Glu Ser Lys Asp Pro Ile Asp Met Ser
    1250             1255              1260
Asp Ile Asp Lys Leu Lys Glu Glu Leu Gln Lys Ile Asn Gln Phe
    1265             1270              1275
Leu Val Lys Ala Met Gly Thr Asn Ile Arg Val Ser Leu Asn Gln
    1280             1285              1290
Met Glu Val Lys Thr Phe Asp Ala Gln Glu Lys Glu Ala Gln Gln
    1295             1300              1305
Asn Leu Lys Gln Leu Asp Ala Leu Ile Asn Lys Leu Glu Ser Ser
    1310             1315              1320
Asp Ala Val Gln Lys Gln Lys Glu Glu Leu Glu Lys Leu Asn Gln
    1325             1330              1335
Leu Leu Val Glu Lys Arg Lys Ala Tyr Pro Ala Met Val Gln Leu
    1340             1345              1350
```

```
Gln Phe Arg Ser Glu Ala Leu Ile Ile His Leu Arg Glu Leu Cys
    1355                1360                1365

Glu Ala His Gln Ala Gln Met Ala Lys Thr Arg Asn Val Arg Ala
    1370                1375                1380

Gln Glu Ile Thr Asn Gly Arg Trp Lys Val Gln Trp Leu Thr Asp
    1385                1390                1395

Trp Val Gly Leu Thr Thr Asp Glu Arg Val Thr Leu Ala Asn Lys
    1400                1405                1410

Glu Lys Glu Leu Ala Lys Phe Lys Glu Asp Leu Asn Asn Asp Glu
    1415                1420                1425

Tyr Asp Leu Gln Glu Leu Ile Ser Asn Leu Ala Glu Lys Asn Pro
    1430                1435                1440

Ser Glu Leu Glu Glu Ala Ile Gly Ile Ser Lys Glu Ser Ala Gln
    1445                1450                1455

Lys Leu His Lys Leu Leu Thr His Leu Asn His Ser Thr Thr Phe
    1460                1465                1470

Met Ser Lys Ile Glu Gln Arg Leu Gln Ser Ile Asp Glu Leu Leu
    1475                1480                1485

Asn Glu Phe Gly Lys Gln Ala Pro Arg Thr Glu Met Ile Lys Thr
    1490                1495                1500

Val Glu Glu Lys Gln Gly Thr Leu Leu Arg Leu
    1505                1510

<210> SEQ ID NO 12
<211> LENGTH: 15
<212> TYPE: PRT
<213> ORGANISM: Artificial sequence
<220> FEATURE:
<223> OTHER INFORMATION: synthesized

<400> SEQUENCE: 12

Glu Gly Ile Pro Pro Asp Gln Gln Arg Leu Ile Phe Ala Gly Lys
1               5                   10                  15
```

UBIQUITINATION SYSTEM AND THE USES THEREOF

CROSS REFERENCES

This application claims the benefit of U.S. Provisional Application 62/318,268, filed on Apr. 5, 2016 and U.S. Provisional Application 62/430,955, filed on Dec. 7, 2016. The disclosures therein are expressly incorporated entirely.

GOVERNMENTAL RIGHTS

This invention was made with government support under AI085403, AI103168, AI105714, and GM103401 awarded by the National Institutes of Health. The government has certain rights in the invention.

TECHNICAL FIELD

The present disclosure generally relates to ubiquitination, in particular to a novel ubiquitination system that involves a single enzyme, and to compositions that may be used in ubiquitination assays and/or methods of screening active substance that may inhibit the ubiquitination process.

BACKGROUND

This section introduces aspects that may help facilitate a better understanding of the disclosure. Accordingly, these statements are to be read in this light and are not to be understood as admissions about what is or is not prior art.

Ubiquitination has long been demonstrated to regulate the fate of numerous cellular proteins and recently it has become apparent that many GTPases, along with their GAPs, GeFs and GDis, undergo ubiquitination leading to a variety of fates such as re-localization or degradation.

Briefly, ubiquitin conjugation plays numerous intracellular roles such as localization, protein interactions, signaling and degradation. Therefore, targeting this process may represent an alternative approach. Additionally, deubiquitinating enzymes (DUBs), which remove ubiquitin from substrate proteins, may also be possible targets for therapeutic intervention and, although not yet at the clinical stage, the development of DUB inhibitors is indeed underway. Directly targeting the proteasome in order to prevent protein degradation has shown some promise, although due to the broad specificity 'off-targets' effects are likely. However, manipulating GTPase function by targeting ubiquitination specifically may be a way around this and produce a source of new therapeutic targets.

Ubiquitination is a reversible multistep process catalyzed by a number of enzymes, that entails the addition of a 79 amino acid tag to a substrate and while frequently this labels for destruction, it also may direct trafficking or alter function. Briefly, ubiquitin is initially activated by an E1 ubiquitin-activating enzyme in an energy dependent process requiring ATP and is subsequently transferred to an E2 ubiquitin conjugating enzyme. Finally, the ubiquitin is transferred to a lysine residue on the target protein with the assistance of a third enzyme termed the E3 ubiquitin ligase.

The removal of ubiquitin by DUBs alters the fate of the protein not only by rescuing it from degradation but also by altering its function, trafficking or activity. Although almost 100 human DUBs have been identified, this is a limited number compared with both the number of E3 ligases (>500) and ubiquitinated substrates suggesting that many of these enzymes must have multiple substrates. Although Ras and other GTPases are mutated in many common cancers, GTPases are by no means the only proteins modified by ubiquitin that are deregulated in cancer or other pathologies. But development of novel drugs to control their ubiquitin-modified activity has the potential to prove clinically beneficial.

A previous example, Bortezomib/Velcade that inhibits proteasome activity, has been approved for the treatment of multiple myeloma and is in clinical trials for other diseases such as non-small cell lung cancer, androgen-independent prostate carcinoma and non-Hodgkin's lymphoma and may also be useful in Ras or Rho mutant cancers. One concern with this broad spectrum approach is the potential side effects, and so more specific targeting of upstream proteins may prove a better option. E3 ligases are one possibility. Indeed, inhibitors for the HECT E3 ligase HDM2, key in p53 stability, have been identified. Additionally, small molecule inhibitors targeting DUB s are also under investigation. However, directly targeting the GTPases and their regulators, may prevent the side effects that have been observed with less specific drugs.

Therefore, there is a need to identify more specific upstream regulators for substrate ubiquitination.

SUMMARY

This disclosure provides a novel ubiquitination system that is independent of E1 and E2 enzymes, instead relying on activation of ubiquitin by ADP-ribosylation, and which is mediated by members of the SidE effector family encoded by the bacterial pathogen *Legionella. Pneumophila.*

In one aspect, the disclosure provides a composition for ATP independent ubiquitination. The composition comprising:
  a) β-nicotinamide adenine dinucleotide (β-NAD);
  b) an ubiquitin or a variant of the ubiquitin; and
  c) an ubiquitin activating protein selected from the group consisting of SEQ ID Nos:1-4 (SdeA, SdeB, SdeC, and SidE respectively), or a variant of any of SEQ ID Nos: 1-4, and any combination of SEQ ID Nos:1-4 or their variants. The variant of SEQ ID Nos: 1-4 has at least 95% sequence identity to the corresponding SEQ ID Nos: 1-4 and maintains a putative mono-ADP-ribosyl-transferase motif (R-S-ExE), and the aforementioned ubiquitin activating protein transfers an ADP from β-NAD to the ubiquitin or the variant of the ubiquitin to form an ADP-ribosylated ubiquitin.

In some embodiment the aforementioned composition further comprising a substrate of the ubiquitin, wherein the substrate is conjugated to the ubiquitin through a ribose-phosphate link on the ADP-ribosylated ubiquitin.

In some embodiment the aforementioned substrate is selected from the group consisting of Rab1, Rab6A, Rab30, Rab33b, Rtn4, Atlastin, and any combination thereof.

In another aspect, the disclosure provides a composition comprising an ADP-ribosylated ubiquitin, wherein the ADP-ribosylated ubiquitin is generated by a ubiquitin activating protein selected from the group consisting of SEQ ID Nos: 1-4 or the combination thereof, and β-nicotinamide adenine dinucleotide (β-NAD), wherein the ubiquitin activating protein adds an ADP to an ubiquitin.

This disclosure further provides a method of identifying an antagonist of ATP independent ubiquitination. The method comprising:
  Providing an ATP independent ubiquitination system, wherein the ATP independent ubiquitin system comprising an aforementioned ADP-ribosylated ubiquitin, and a substrate selected from the group consisting of Rab1, Rab6A, Rab30, Rab33b, Rtn4, and Atlastin;

Providing a series of substance to the ATP independent ubiquitin system to observe the substance's effect on the substrate ubiquitination by the ADP-ribosylated ubiquitin; and Identifying at least one substance that prevents the substrate ubiquitination.

In one aspect, the aforementioned substance is selected from the group consisting of SEQ ID Nos: 8-11, or the combination of thereof. SEQ ID Nos: 8-11 are mutant form of SedA, SedB, SedC and SidE wherein the putative mono-ADP-ribosyltransferase motif (R-S-ExE) is from ExE to R-S-AxA.

In one aspect, the aforementioned substance is an antibody to an ADP-ribosylated ubiquitin.

In one aspect, the aforementioned substance is a mutant ubiquitin that has no Arginine at position 42.

This disclosure further provides a kit for identifying ATP independent ubiquitination substrates. The kit comprising β-nicotinamide adenine dinucleotide (β-NAD), a protein selected from the group consisting of SdeA, SdeB, SdeC, SidE or the homologs thereof, and a ubiquitin or a variant of ubiquitin that has at least one site for ADP-ribosylation. In some embodiment, such site for ADP-ribosylation requires Arginine at position 42 of the ubiquitin.

In one aspect, the aforementioned kit identifies a substrate conjugated to an ADP-ribosylated ubiquitin or the variant of ubiquitin through a ribose-phosphate link.

In one aspect, the aforementioned substance is selected from the group consisting of Rab1, Rab6A, Rab30, Rab33b, Rtn4, and Atlastin.

These and other features, aspects and advantages of the present invention will become better understood with reference to the following figures, associated descriptions and claims.

BRIEF DESCRIPTION OF THE FIGURES

FIGS. 1A-1C show that a putative mono-ADP-ribosyltransferase (mART) motif is important for yeast toxicity of SdeA. FIG. 1A shows Alignment of the central region of the SidE family members and several toxins with mART activity. Proteins identified by PSI-BLAST were manually aligned. Shown mART toxins are IotA from *Clostridium perfringens*, the C3 exoenzyme from *Clostridium botulinum* and ExoS from *Pseudomonas aeruginosa*. Residues important for the mART motif were highlighted in red. FIGS. 1B and 1C show the mART is essential for yeast toxicity and for secretion inhibition by SdeA. Yeast cells were spotted on the indicated medium for 3 days before image acquisition. The secretion of SEAP was examined in 293T cells transfected to express SEAP and GFP-tagged testing proteins; the strong SEAP inhibitor AnkX was used as a control. Error bars represent standard error of the mean (s.e.m.) (n=3). The expression of the proteins (the lower panel in FIG. 1B for yeast and the right panel in c for mammalian cells) was probed with indicated antibodies. The PGK (3-phosphoglyceric phosphokinase) and tubulin were probed as a loading control, respectively. SdeA$_{E/A}$, SdeA with Glu860 and Glu862 mutated to Ala. IB, immunoblotting. The yeast toxicity results in FIG. 1B and protein levels in FIGS. 1B and 1C are from one representative of three independent experiments. The SEAP results in FIG. 1C are one representative done in triplicate from three independent experiments (FIGS. 1B and 1C). Uncropped blots are shown in FIG. 5.

FIG. 2A: The indicated bacterial strains were used to infect *D. discoideum* and the bacterial yields were monitored at 24-h intervals. Note that SdeA but not the SdeA$_{E/A}$ mutant restored the defect exhibited by the ΔsidE strain. FIG. 2B: Expression and Dot/Icm-mediated translocation of SdeA and SdeA$_{E/A}$. The bacteria used for infections were probed for protein expression; the metabolic enzyme isocitrate dehydrogenase (ICDH) was probed as a loading control (top panel). Saponin-soluble fractions of infected cells were probed for translocated SdeA with tubulin as a loading control (bottom panel). FIGS. 2C and 2D: *L. pneumophila* was used to infect a strain of *D. discoideum* stably expressing the ER retention fusion GFP-HDEL and the recruitment of the ER marker to the phagosome was evaluated 2 h after infection. IB, immunoblotting. Results in FIGS. 2A and 2C are from one representative experiment done in triplicate from three independent experiments; error bars represent standard error of the mean (s.e.m.) (n=3). Results in FIGS. 2B and 2D are one representative from three independent experiments. Scale bar, 5 μm. FIG. 2B.

FIG. 3A shows lysates of 293T cells co-transfected to express SdeA and Flag-tagged small GTPases were subjected to immunoprecipitation with Flag beads and the products were probed with the Flag-specific antibody. Note the appearance of shifted bands for Flag-tagged ER-associated Rabs but not for Rab5 and Rac1. M, SdeA$_{E/A}$; W, SdeA; IgG (HC) and IgG (LC) indicate IgG heavy and light chains, respectively. FIG. 3B: SdeA-dependent post-translational modification of Rab33b during bacterial infection. Cells expressing Flag-Rab33b were infected with relevant *L. pneumophila* strains for 2 h and Flag-Rab33b purified from cell lysates was probed by immunoblotting. FIGS. 3C-3F: SdeA induces Rab33b ubiquitination. Flag-Rab33b purified from cells co-expressing SdeA (FIG. 3C) or infected with wild-type *L. pneumophila* (FIG. 3E) was subjected to mass spectrometric analysis and tryptic ubiquitin fragments were identified in proteins of the shifted bands (FIGS. 3D and 3F). FIG. 3G: Overexpression of Rab33b restricts intracellular bacterial growth. COS 1 cells transfected with Rab33b and the indicated mutants were infected with *L. pneumophila* and the formation of replicative vacuoles was determined. IB, immunoblotting. Data shown are one representative experiment of three independent experiments (FIGS. 3A-3F); results in FIG. 3G are one representative done in triplicate from three independent experiments. Error bars represent standard error of the mean (s.e.m.) (n=3). FIGS. 3A-3C and 3E.

FIG. 4A: A heat-stable molecule from cells is required for ubiquitination induced by SdeA. Reactions resolved by SDS-PAGE were probed with the indicated antibodies. Note the production of ubiquitinated Rab33b in reactions containing boiled mammalian (m) cell lysates and *E. coli* lysates. TCL, total cell lysates. FIG. 4B: NAD is required for SdeA-catalysed ubiquitination. Ubiquitinated Rab33b and SdeA were probed by Coomassie staining or by immunoblotting (IB) with antibodies specific for ubiquitin or Flag. FIG. 4C: Self-ubiquitination by SdeA. SdeA or SdeA$_{E/A}$ was incubated with GST-ubiquitin and NAD; ubiquitination was detected by immunoblotting or by Coomassie staining. Note the formation of the high molecular weight self-ubiquitinated SdeA when GST-ubiquitin was included in the reactions. FIG. 4D: Ubiquitination catalysed by the central domain of SdeA. SdeA$_{178-1000}$ or SdeA$_{178-1000E/A}$ was used for ubiquitination of Rab33b and the products were probed by Coomassie staining or by immunoblotting. FIGS. 4A-4D: Similar results were obtained from four experiments.

BRIEF DESCRIPTION OF SEQUENCE LISTINGS

Figure 1B:
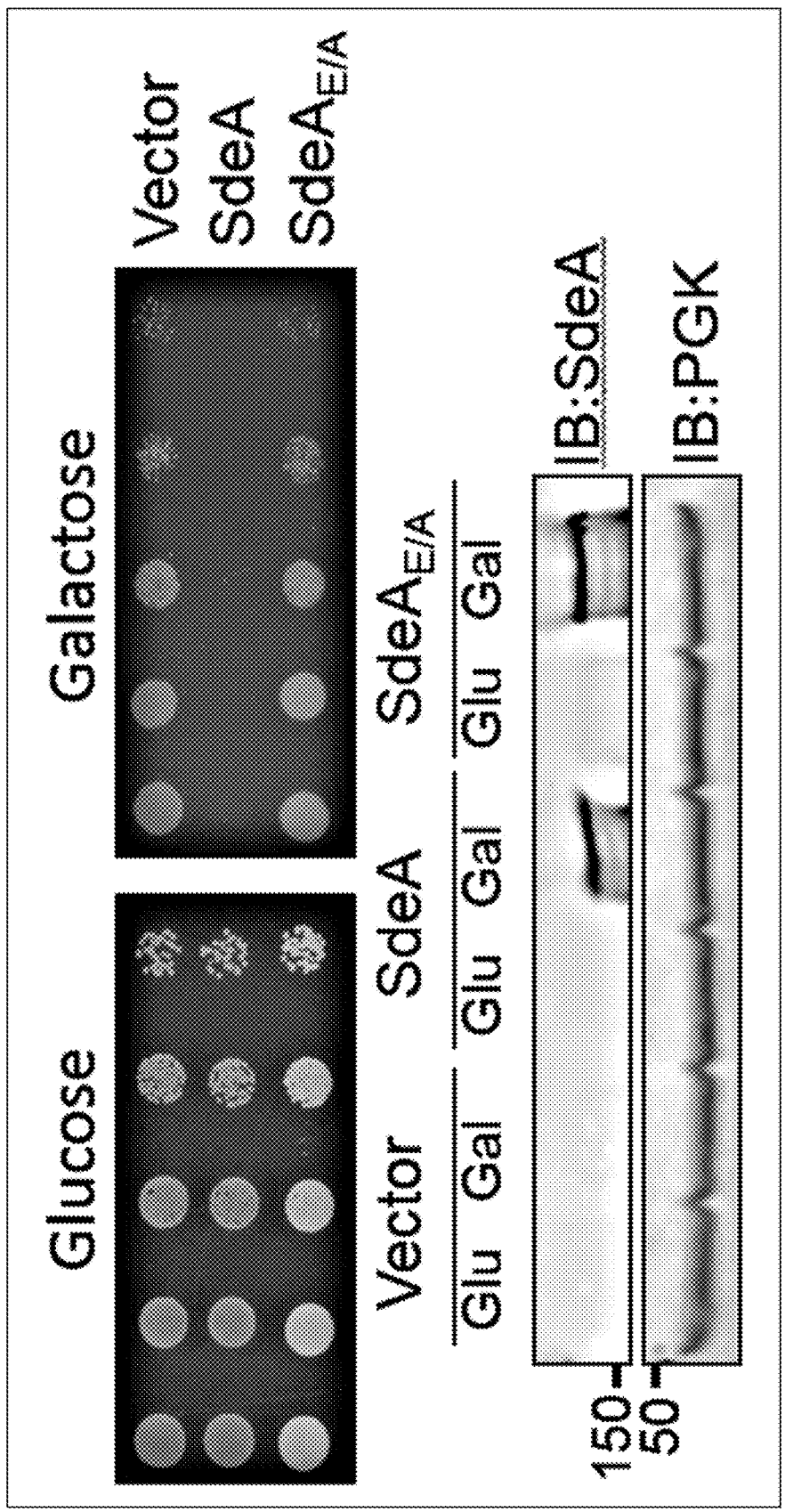

SEQ ID NOS: 1-4 represent SdeA, SdeB, SdeC, and SidE respectively from *L. Pneumophila*

SEQ ID NO:5 represents IOTA from *Clostridium perfringens*

SEQ ID NO:6 represents C3 exoenzyme from *Clostridium botulinum*

SEQ ID NO:7 represents ExoS from *Pseudomonas aeruginosa*

SEQ ID NO:8-11 represent mutant form of SdeA, SdeB, SdeC and SidE respectively with mART motif mutated from R-S-ExE to R-S-AxA.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

Unless defined otherwise, the scientific and technology nomenclatures have the same meaning as commonly understood by a person in the ordinary skill in the art pertaining to this disclosure.

As used herein, a putative mono-ADP-ribosyltransferase motif (R-S-ExE) is referred to as mART, which exist within bacterial pathogen *L. Pneumophila* SidE effector family proteins. It is contemplated that these proteins or their homologs, variants that retain such mART motif, possess ADP-ribosyltransferase activity and are able to provide at least one ADP to an ubiquitin from β-nicotinamide adenine dinucleotide (β-NAD).

As used herein, an ATP independent ubiquitination process requires an ubiquitin activating protein, such ubiquitin activating protein is β-NAD dependent and at least some exemplified such ubiquitin activating proteins provide ADP-ribosylation to ubiquitin.

As used herein, (β-NAD) dependent ubiquitination substrates are proteins that conjugated to ADP-ribosylated ubiquitin through a ribose-phosphate link.

The ability of the bacterial pathogen *L. pneumophila* to replicate within a phagocyte depends completely upon the Dot/Icm type IV secretion system that translocates hundreds of substrates (effectors) into host cells. The activity of these effectors supports the biogenesis of the *Legionella*-containing vacuole (LCV), an area that is made permissive for bacterial replication by manipulating such diverse host processes as vesicle trafficking, protein translation, autophagy, cell migration, gene expression and the biosynthesis of signaling lipids, often with sophisticated mechanisms. With a few exceptions the roles of Dot/Icm effectors in *L. pneumophila* infection of its host are not fully understood because deletion of these genes individually often does not affect intracellular bacterial replication. A biochemical function has been assigned to less than 10% of these effectors.

Signaling by ubiquitination regulates virtually every cellular process in eukaryotes. Covalent attachment of ubiquitin to a substrate is catalyzed by the E1, E2 and E3 three-enzyme cascadel, which in most cases links the carboxyl terminus of ubiquitin to the c-amino group of a lysine of the substrate via an isopeptide bond. Given the essential roles of ubiquitination in the regulation of the immune system, it is not surprising that the ubiquitination network is a common target for diverse infectious agents. For example, many bacterial pathogens exploit ubiquitin signaling using virulence factors that function as E3 ligases, deubiquitinases or as enzymes that directly attack ubiquitin. The bacterial pathogen *Legionella pneumophila* utilizes approximately 300 effectors that modulate diverse host processes to create a permissive niche for its replication in phagocytes. Herein we demonstrate that members of the SidE effector family of *L. pneumophila* ubiquitinate multiple Rab small GTPases associated with the endoplasmic reticulum. Moreover, we show that these proteins are capable of catalyzing ubiquitination without the need for the E1 and E2 enzymes. A putative mono ADP-ribosyltransferase motif critical for the ubiquitination activity is also essential for the role of the SidE family in intracellular bacterial replication in a protozoan host. The E1/E2-independent ubiquitination catalyzed by these enzymes is energized by nicotinamide adenine dinucleotide, which activates ubiquitin by the formation of ADP-ribosylated ubiquitin. These results establish that ubiquitination can be catalysed by a single enzyme, the activity of which does not require ATP.

The discovery herein has significant implications on how to design cellular process modulators. For example, identifying any β-NAD-dependent ubiquitination substrates is imperative to complete the understanding of this ATP independent ubiquitination process. Any antagonist that prevents β-NAD-dependent ADP-ribosylation of ubiquitin may lead to inhibition of ubiquitination to β-NAD-dependent ubiquitination substrates. These antagonists may be antibodies to ADP-ribosylated ubiquitin, or antibodies to the ubiquitin activating proteins identified herein (SidE family effectors) in this disclosure, or any future identified functional equivalents to these β-NAD-dependent ubiquitin activating proteins. Thus, substances targeting ADP-ribosyltransferase activity may provide additional cellular process modulators. Using the discovery in this disclosure to identify additional substrates of ATP independent ubiquitination provides important insights to cancer development and targeting. At least some mutants of SidE family effectors that lose ADP-ribosyltransferase signature motif lead to the loss of ubiquitination activating function, such as R-S-ExE to R-S-AxA mutant of these family proteins.

Methods

Bacterial, Yeast Strains and Plasmid Construction

*L. pneumophila* strains used in this study were derivatives of the Philadelphia 1 strain Lp02 (ref. 31) and were grown and maintained on CYE medium or in AYE broth as previously described[31]. When necessary antibiotics were included as described. The ΔsidE strain was made by step-wise deletion of the 4 members using an established method. For complementation experiments, the genes were inserted into pZL507 (ref. 32). All infections were performed with bacterial cultures grown to the post-exponential phase as judged by optical density of the cultures ($OD_{600}$=3.3-3.8) as well as increase of bacterial motility. For expression in mammalian cells, genes were cloned into pEGFPC1 (Clontech) or a 4×Flag vector[32]. The integrity of all constructs was verified by sequencing analysis.

Cell Culture, Infection, Transfection and Co-Immunoprecipitation

HEK293 or 293T cells (ATCC) were cultured in Dulbecco's modified minimum Eagle's medium (DMEM) supplemented with 10% FBS. Cells grown to about 80% confluence were transfected with Lipofectamine 3000 (Life Technology) following manufacturer's instructions. U937 cells (ATCC) were differentiated into macrophages as described[33]. *D. discoideum* strains AX4 and AX4-HDEL-GFP were cultured in HL-5 medium as described earlier. Strains of *L. pneumophila* used for infection were grown in AYE to post-exponential phase judged by optical density ($OD_{600}$=3.2-4.0) and by increase in motility. $2\times10^5$ *D. discoideum* cells seeded in 24-well plates were infected with an MOI of 0.05 for growth experiments and of 5 for immunostaining. In all cases, one hour after adding bacteria to cultured cells, infections were synchronized by washing the infected cells three times with warm PBS buffer. Total bacterial counts at indicated time points were determined by plating serially diluted saponin lysates onto bacterial media. To determine the development of the LCV in COS 1 cells (ATCC) expressing Rab33b and its mutants, cells transfected for 14 h were infected with wild-type *L. pneumophila* and samples were fixed 14 h after bacterial uptake. Intracellular and extracellular bacteria were differentially stained with a *Legionella*-specific antibody and secondary antibodies conjugated to different fluorescence dyes. The category of LCVs was scored visually under a fluorescence microscope. All cell lines used were directly purchased from ATCC and were free of mycoplasma contamination by monthly testing using the PlasmoTest Kit (Invivogen).

For infections to determine the modification of Rab33b, HEK293 cells were transfected to express 4×Flag-Rab33b and FCγRII for 24 h with Lipofectamine 3000 (Life Technology). Bacteria of relevant *L. pneumophila* strains were opsonized with rabbit anti-*Legionella* antibodies[32] at 1:500 for 30 min before infecting the cells at an MOI of 10 for 2 h. Lysates prepared from infected cells with RIPA buffer (Thermo Fisher Scientific) were subjected to immunoprecipitation with Flag beads (Sigma-Aldrich).

To determine protein translocation by *L. pneumophila*, cells infected with the indicated bacterial strains were lysed with 0.2% saponin, which lyses membranes of mammalian cells but not of bacterial cells. The lysates were directly probed for SdeA with a specific antibody.

The secretion of SEAP was measured 24 h after cells were transfected with plasmids carrying the testing genes and pSEAP[22,35]. The alkaline phosphatase activity was determined with Tropix phosphalight System kit (Applied Biosystems) per the manufacturer's instructions.

Yeast Toxicity Assays

All yeast strains used were derived from W303 (ref. 36); yeast was grown at 30° C. in YPD medium or in appropriate amino acid dropout synthetic media with glucose or galactose at a final concentration of 2% as the sole carbon source. Yeast transformation was performed according to a standard procedure[37]. Inducible protein toxicity was assessed by the galactose-inducible promoter on pSB157 (ref. 38). SdeA or its mutant was inserted into pSB157 and the resulting plasmids were linearized before transforming into yeast strain W303 (ref. 36). Yeast strains grown in liquid selective medium containing glucose were serially diluted fivefold, and 10 μl of each dilution was spotted onto selective plates containing glucose or galactose. Plates were incubated at 30° C. for 3 days before the images were acquired.

Protein Purification

To purify Flag-Rab33b from mammalian cells, 293T cells transfected with the indicated plasmids for 24 h were lysed with RIPA buffer. Flag-antibody-coated beads were added to cleared lysates and obtained by centrifugation at 12,000 g for 10 min. The mixtures were incubated at 4° C. with agitation for 4 h. Unbound proteins were removed by washing the beads three times with RIPA buffer and the Flag-tagged proteins were eluted with 450 μg ml$^{-1}$ 3×Flag peptide solution. To purify modified Rab33b from infected cells, HEK293 cells transfected to express 4×Flag-Rab33b and FCγRII were infected with wild type *L. pneumophila* for 2 h. The samples were lysed with RIPA buffer. Flag-Rab33b from the infection samples were purified followed the same protocol used for transfection samples.

Unless otherwise specified, the *E. coli* strain BL21(DE3) was used as the host for expression and purification of recombinant proteins. Rab1 was purified as GST-tagged protein, while all other proteins were purified as His$_6$-tagged proteins. pQE30-4×Flag-Rab33b was sub-cloned from the mammalian expression vector p4×Flag-Rab33b to produce His$_6$-4×Flag-Rab33b. For protein production, 30 ml of overnight culture of the *E. coli* strain harbouring the appropriate plasmid was transferred to 750 ml LB medium (ampicillin 100 μg ml$^{-1}$) and grown until $OD_{600}$ of 0.6~0.8 was reached. After adding IPTG (isopropyl thio-D-galactopyranoside) to a final concentration of 0.2 mM, the cultures were further incubated in a shaker at 18° C. for 16~18 h. Bacterial cells were harvested by spinning at 12,000 g and lysed by sonication in the presence of protease inhibitors. The soluble fractions were collected by centrifugation at 12,000 g twice at 4° C. His-tagged proteins were purified with Ni$^{2+}$-NTA beads (Qiagen), and eluted with PBS containing 300 mM imidazole; GST-Rab1 were purified with Glutathione Sepharose 4 Fast Flow beads (GE healthcare), and proteins bound to beads were eluted with 25 mM reduced glutathione in 20 mM Tris-HCl, pH 8.0, 100 mM NaCl. Purified proteins were dialysed in a buffer containing 25 mM Tris-HCl, pH 7.5, 150 mM NaCl, 5% glycerol, 1 mM DTT. To determine the potential involvement of the ions and other co-factors in the activity of SdeA, the protein was dialysed against the same buffer containing 10 mM EDTA for 14 h at 4° C. Protein concentrations were determined by the Bradford assay. For proteins used in in vitro biochemical assays, extensive dialysis was performed with at least two buffer changes. The purity of proteins was larger than 95% as assessed by Coomassie brilliant blue staining.

In Vitro Ubiquitination Assays

E1, E2 and ubiquitin were obtained from Boston Biochem and were used at 100 nM for each 50-μl reaction. Ubiquitination assays were performed at 37° C. for 2 h in a reaction buffer containing 50 mM Tris-HCl (pH 7.5), 0.4 mM β-nicotinamide adenine dinucleotide (β-NAD) (Sigma-Aldrich) and 1 mM DTT. Each 50-μl reaction contains 10 μg ubiquitin, 5 μg SdeA, SdeB, SdeC, SidE or their mutant proteins and 5 μg substrates. When necessary, ATP and $Mg^{2+}$ were added to a final concentration of 2 mM and 5 mM, respectively. When needed, 50 μg of mammalian or E. coli lysates were added. Heat treatment of cell lysates or NAD was performed at 100° C. for 5 min. When necessary maleimide (MEM) was added to in vitro reactions at a final concentration of 50 μM.

Antibodies, Immunostaining and Immumobloting

Antibodies against Legionella and GFP were described elsewhere[32]. Antibodies specific for SdeA were prepared by injecting rabbits with purified protein (Pocono Rabbit Farm and Laboratory, Canadensis, Pa.) following a standard procedure used by the service provider. When necessary, antibodies were affinity-purified against the same proteins covalently coupled to an Affigel matrix (Bio-Rad) using standard protocols[39]. Cell fixation, permeabilization and immunostaining were performed as described[40]. For immunostaining, anti-Legionella antisera were used at 1:10,000 (ref. 32). Intracellular bacteria were distinguished from extracellular bacteria by differential immunostaining with secondary antibodies of distinct fluorescence dyes. Processed samples were inspected and scored using an Olympus IX-81 fluorescence microscope.

For immunoblotting, samples resolved by SDS-PAGE were transferred onto nitrocellulose membranes. After blocking with 5% milk, membranes were incubated with the appropriate primary antibody: anti-GFP (Sigma, cat. no. G7781), 1:10,000; anti-GST (Sigma, cat. no. G6539), 1:10,000; anti-Flag (Sigma, F1804), 1:2,000; anti-ICDH, 1:10,000; anti-PGK (Life Technology, cat. no. 459250), 1:3,000; anti-SdeA, 1:10,000; anti-SidC[6], 1:10,000; anti-Ub (Santa cruz, cat. no. sc-8017), 1:1,000; anti-His (Sigma, cat. no. H1029), 1:10,000. Tubulin (DSHB, E7), 1:10,000. Membranes were incubated with an appropriate IRDye infrared secondary antibody (Li-Cor's Biosciences Lincoln, Nebr., USA) and the signals were obtained by using the Odyssey infrared imaging system.

GTP Loading Assay

For $^{35}S\gamma GTP$ incorporation assays, 20 μg of 4×Flag-Rab33b was loaded with unlabelled GDP (5 mM) before ubiquitination as described[22]. GDP loaded 4×Flag-Rab33b was used for ubiquitination assays in the presence of either SdeA (10 μg) or $SdeA_{E/A}$ (10 μg) for 2 h at 37° C. 20% of the samples were withdrawn to test for the extent of ubiquitination of 4×Flag-Rab33b by SDS-PAGE and Coomassie staining. Ubiquitinated or non-ubiquitinated 4×Flag-Rab33b was incubated in 50 μl nucleotide exchange buffer containing 25 mM Tris-HCl (pH 7.5), 50 mM NaCl, 5 mM $MgCl_2$, and 0.1 mM EDTA with 5 μCi $^{35}S\gamma GTP$ (Perkin-Elmer). GTP-loading reactions were performed at 22° C. Aliquots of reactions were withdrawn at indicated time points, passed through nitrocellulose membrane filters (Hawp02500; Millipore) and placed onto a vacuum platform attached to a waste liquid container. Membranes were washed three times using the exchange buffer to remove the free nucleotides, and were then transferred into scintillation vials containing 8 ml scintillation fluid (Beckman). Incorporated $^{35}S\gamma GTP$ was detected by a scintillation counter at 1 min per count.

GTPase Assay

20 μg of 4×Flag-Rab33b was used for ubiquitination assays in the presence of either SdeA (10 μg) or $SdeA_{E/A}$ (10 μg) for 2 h before 5 μCi of $^{32}P\gamma GTP$ (Perkin-Elmer) was added to the reactions. Nucleotide loading was performed at 22° C. for 30 min. Aliquots of the reactions were withdrawn and passed through membranes as described in the GTP loading assay. The reading of these aliquots served as starting points for different reactions. Samples withdrawn at later time points were measured for $^{32}P\gamma GTP$ and retained by 4×Flag-Rab33b-bound with a scintillation counter. The GTP hydrolysis index was calculated by dividing the readings obtained in later time points by the values of the starting point.

ADP-Ribosylation Assay

5 μg of SdeA or $SdeA_{E/A}$ was incubated with 5 μg of GST-Rab1, 4×Flag-Rab33b or 100 μg of 293T cell lysate in the presence of 10 mM Tris-HCl (pH 7.5), 20 mM NaCl. 5 μCi of $^{32}P$-α-NAD (Perkin-Elmer) was added to each reaction. ADP-ribosylation assays were performed at 22° C. for 1 h and were stopped by adding 5×SDS loading buffer. A reaction containing $EXOS_{78-453}$ (200 ng), FAS (factor activating ExoS) (2 μg), Rab5 (5 μg) or 293T cell lysates (100 μg) was used as positive control. The incorporation of $^{32}P$-α-ADPR into proteins was detected by autoradiography.

Detection of Reaction Intermediates by $^{32}P$-Labelled ATP and NAD

To detect the ubiquitin intermediate, 5 μg of SdeA or $SdeA_{519-1100}$ was incubated with 10-μg GST-ubiquitin, GST-$ubiquitin_{R42A}$ or GST in the presence of $^{32}P$-α-NAD (5 μCi) in a reaction buffer containing 50 mM Tris-HCl (pH 7.5). The reaction was performed at 37° C. for 6 h and stopped by adding 5×SDS loading buffer. A reaction containing the E1 activating enzyme (1 μg), GST-ubiquitin or GST (10 μg), $^{32}P$-α-ATP (5 μCi) in the presence of 50 mM Tris-HCl (pH 7.5) and 2 mM $MgCl_2$ was used as a positive control. The $^{32}P$-labelled intermediates were detected by autoradiography.

Detection of Reaction Intermediates

To detect AMP generated in reactions catalysed by SdeA, reactions were set up with 50 μg $SdeA_{178-1000}$, 10 mM NAD and 450 μg ubiquitin in reaction buffer (50 mM Tris pH 7.6, 50 mM NaCl, 1 mM DTT) and allowed to react for 2 h at 22° C. To detect all reaction intermediates, a reaction was set up with 100 μg $SdeA_{178-1000}$, 1 mM NAD and 100 μg ubiquitin in reaction buffer (50 mM Tris pH 7.6, 50 mM NaCl, 1 mM DTT) and allowed to react for 16 h at 22° C. The reaction was then separated on an Agilent C8 column using a Waters 600 HPLC system with a linear gradient of 0-5% (v/v) acetonitrile in water over 25 min at 1 ml per minute. The intermediates were detected with a Waters 2487 dual wavelength detection system with wavelengths set to 260 nm and 280 nm. The mixture was then directly analysed with a Waters micromass ZQ spectrometer in negative electrospray ionization mode. The detection range was set from 100-700 (m/z) with a scans at 1 s intervals. Standard samples of AMP, ADP, NMN, and nicotinamide were set up in parallel and analysed following the same method to determine the elution profile of each possible intermediate.

For experiments using $SdeA_{519-1100}$ defective in autoubiquitination, 50 μg of $SdeA_{519-1100}$ was incubated with 15 μg ubiquitin and 1 mM NAD in reaction buffer (50 mM Tris pH 7.6, 50 mM NaCl, 1 mM DTT) at 22° C. for 18 h. The reaction was then applied directly to an Agilent C8 column on a Waters 600 HPLC system. The products of the reaction were separated with a linear gradient of 0-5% (v/v) acetonitrile in water with a flow rate of 1 ml per min over 25 min. The products were detected with a Waters 2487 dual wavelength detection system set to 260 nm and 280 nm. Controls used were 1 mM solutions containing only NAD, nicotinamide or AMP.

Samples for mass spectrometric analysis were obtained by using $His_6$-ubiquitin in reactions containing $SdeA_{519-1100}$ and NAD for 2 h, $SdeA_{519-1100}$ and other components were removed by $Ni^{2+}$ beads chromatography. Eluted proteins were separated in SDS-PAGE and the band corresponding ubiquitin was excised and digested with trypsin. Resulting peptides were analysed in a NanoAcquity nanoHPLC system (Waters) by loading peptides into a trap column (5 cm×150 μm i.d. column packed in-lab with 5 μm Jupiter C18 stationary phase) and separated in a 40 cm×75 μm i.d. column packed in-lab with 3 μm Jupiter C18 stationary phase. The elution was carried out at 300 nl per min with the following gradient: 0-8% B solvent in 2 min, 8-20% B in 18 min, 12-30% B 55 min, 30-45% B in 22 and 97-100% B in 3 min, before holding for 10 min at 100% B. Eluting peptides were introduced to the mass spectrometer (Q-Exactive HF, Thermo Fisher Scientific) using electrospray ionization and mass spectra were collected from 400-2,000 m/z with 100 k resolution at intz 400 (k stands for 1000. You can also revise the text to: 100×1000). HCD tandem-mass spectra were collected by data-dependent acquisition of the 12 most intense ions using normalized collision energy of 30%. A dynamic exclusion time of 45 s was used to discriminate against previously analysed ions. Spectra were analysed manually by de novo sequencing.

Data Quantitation and Statistical Analyses

Student's t-test (two-sided) was used to compare the mean levels between two groups each with at least three independent samples.

Figure 1C:
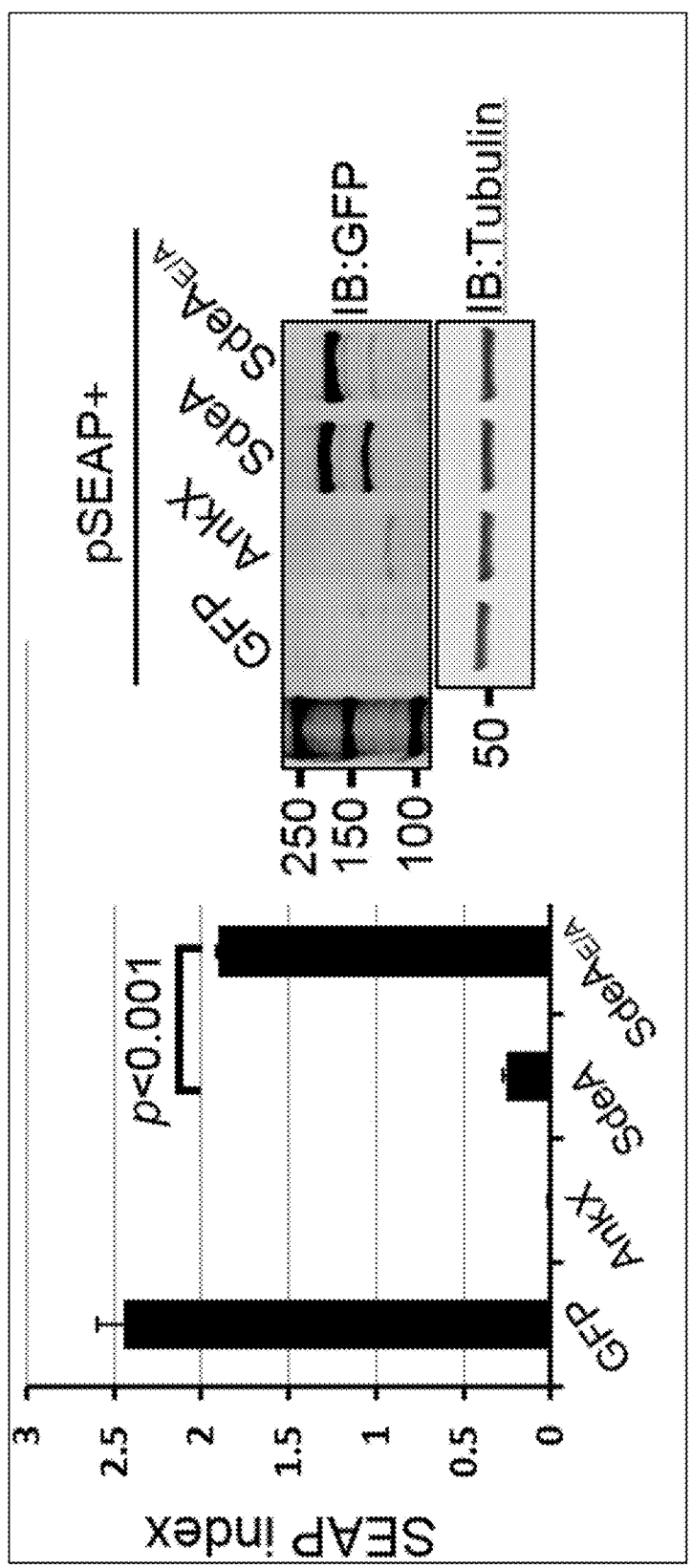
Figure 5:
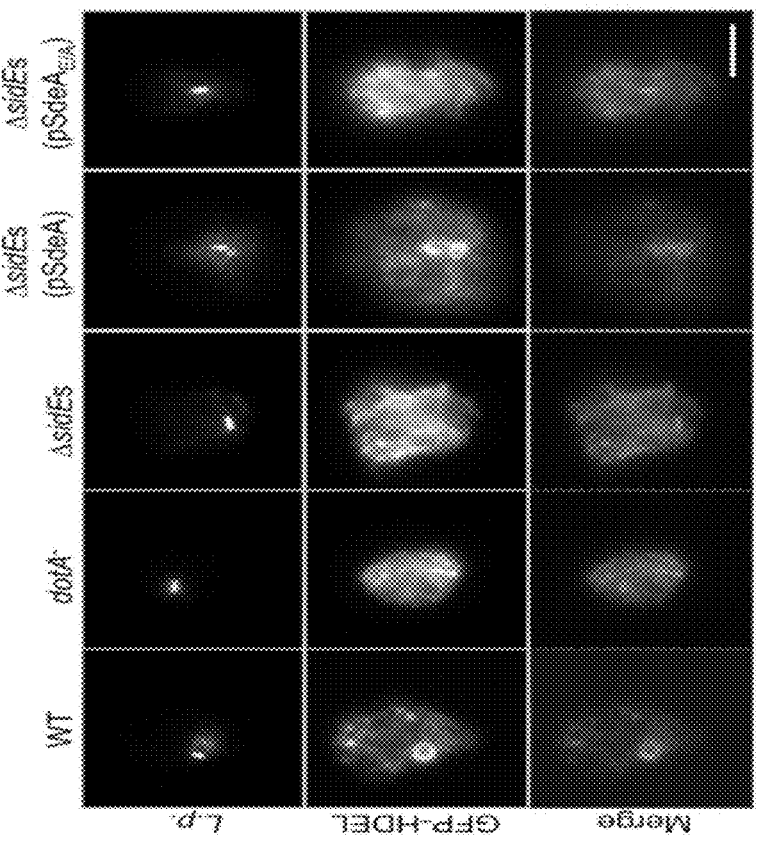
FIGS. 5A-5C Inhibition of the secretion of SEAP by SidE, SdeB and SdeC and the recruitment of an ER marker by the *L. pneumophila* mutant lacking the SidE family. 5A, GFP-fusions of the indicated proteins were co-expressed with SEAP in 293T cells for 24 h. The SEAP index was determined by measuring alkaline phosphatase activity in culture supernatant or in cells. Similar results were obtained in three independent experiments, and data shown are from one representative experiment done in triplicate. Note that mutations in the putative mART motif abolished the inhibitory effects. Error bars represent standard error of the mean (s.e.m.) (n=3). 5B, Quantitation of the vacuoles positive for GFP-HDEL. The indicated bacterial strains were used to infect a line of *D. discoideum* stably expressing GFP fusion to the ER retention signal HDEL and the recruitment of the GFP-HDEL signal to the phagosome was evaluated 10 h after infection. At least 150 phagosomes were scored in each sample done in triplicate. Results shown are from one representative experiment done in triplicate and similar results were obtained from three independent experiments. Error bars represent standard error of the mean (s.e.m.) (n=3). 5C, Representative images of *L. pneumophila* phagosomes associated with GFP-HDEL. Images are from one representative of three independent experiments with similar results. Scale bar, 5 µm.
Figure 5:
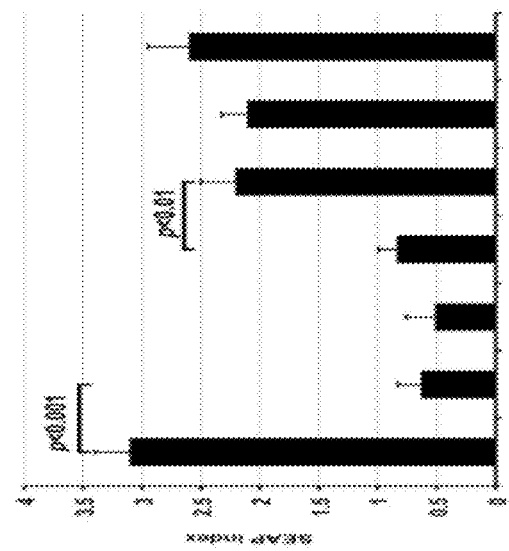
Figure 5:
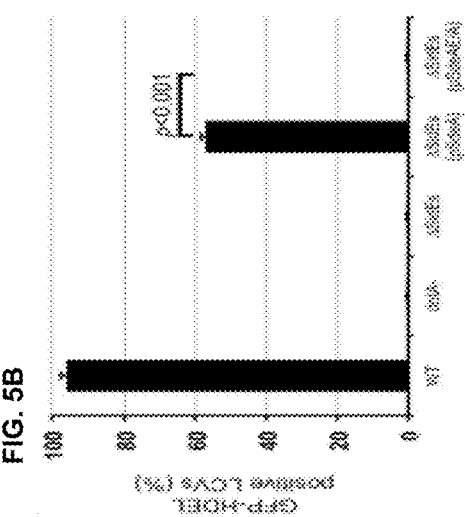

The SidE effector family contains four large proteins that are required for proficient intracellular bacterial replication. PSI-BLAST analysis identified a putative mono ADP-ribosyltransferase (mART) motif (R-S-ExE) in the central region of each of these proteins that is also present in such bacterial toxins as IotA, C3 exoenzyme and ExoS (FIG. 1A). Among these, the putative mART element in SdeA is $R_{766}$-$S_{820}$-$E_{860}S_{861}E_{862}$, a catalytic motif found in enzymes that transfer the ADP-ribosyl group from nicotinamide adenine dinucleotide (NAD) to arginine residues. To examine its role in SdeA-mediated yeast toxicity, we created the $SdeA_{E/A}$ mutant, in which $E_{860}$ and $E_{862}$ were mutated to alanine. This mutant has completely lost its toxicity to yeast and was also defective in inhibiting the secretion of the secreted form of the embryonic alkaline phosphatase (SEAP) by mammalian cells (FIGS. 1B, 1C). SidE, SdeB and SdeC also significantly inhibited SEAP secretion in a manner dependent upon the predicted mART motif (FIG. 5A). These results indicate that the putative mART motif is essential for the activity of the SidE family effectors.

Figure 2A:
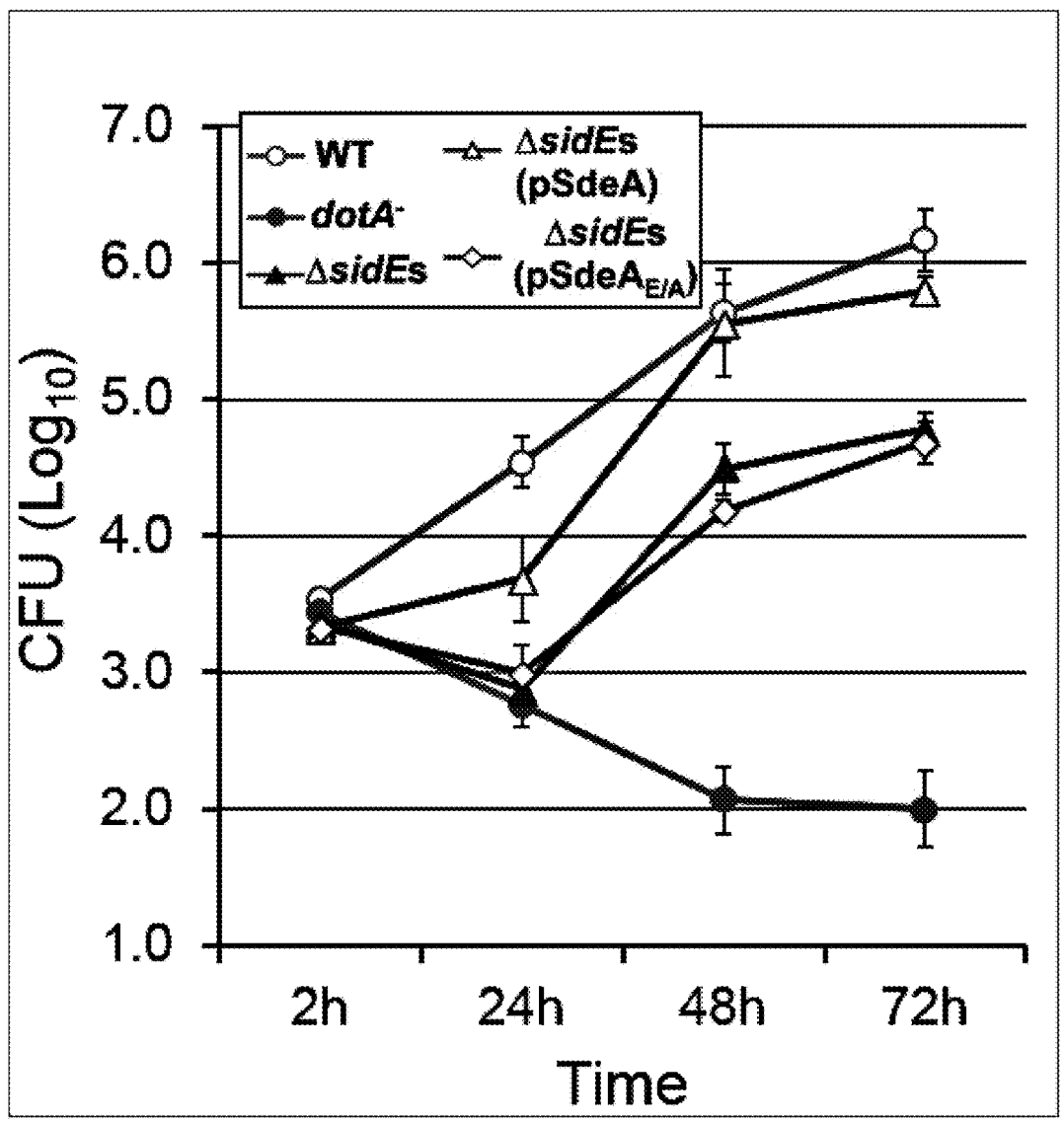
FIGS. 2A-2D show the predicted mART motif is essential for the role of SdeA in intracellular bacterial growth.
Figure 2B:
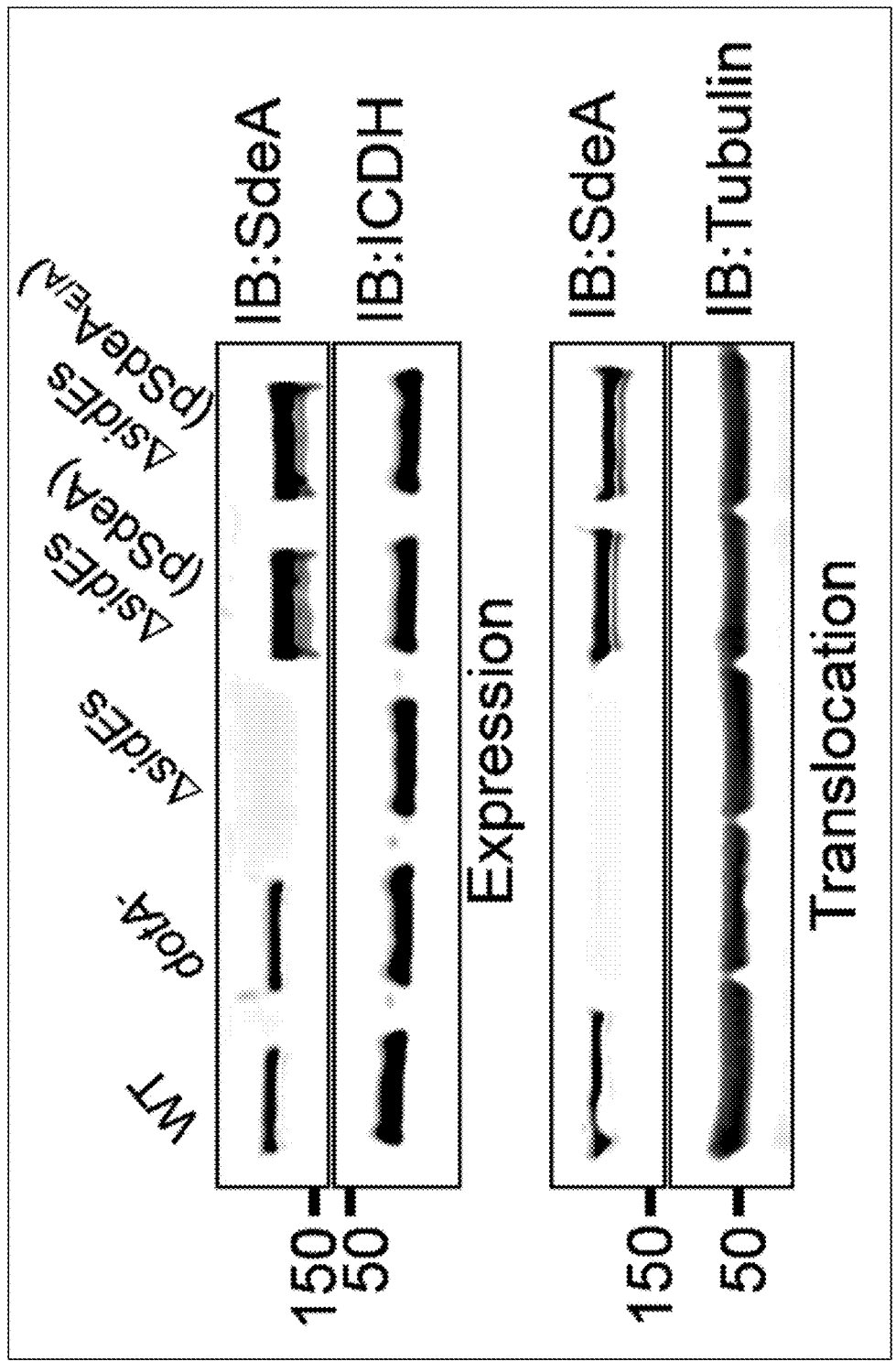
Figure 2C:
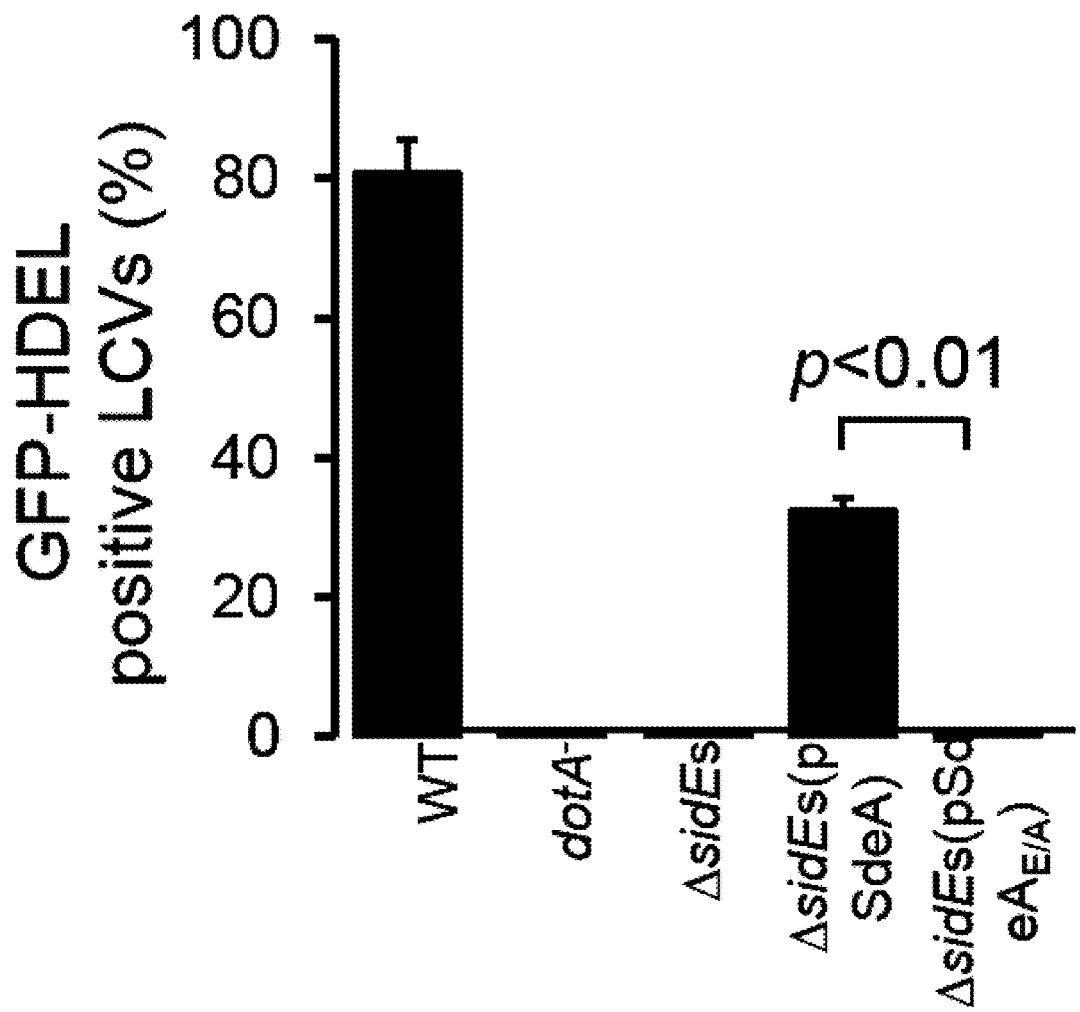
Figure 2D:
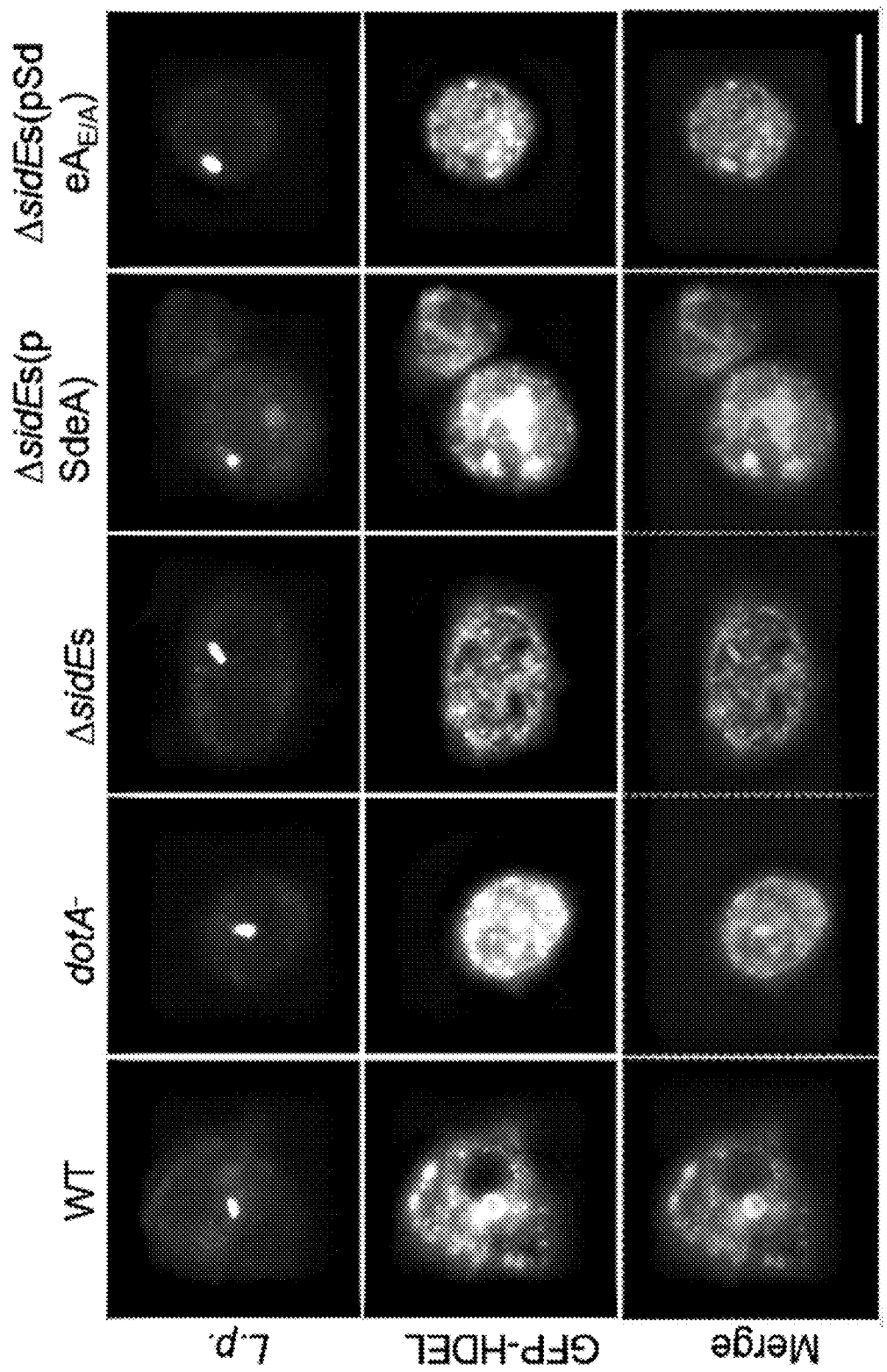

A mutant missing the SidE family (ΔsidE) shows attenuated virulence against the protozoan host Dictyostelium discoideum (FIG. 2A). Expression of wild-type SdeA but not the $SdeA_{E/A}$ mutant in a ΔsidE strain almost completely restored its ability to grow within the host (FIGS. 2A, 2B). In D. discoideum, LCVs containing wild-type bacteria efficiently recruit endoplasmic reticulum (ER) markers such as the GFP-HDEL fusion to their surface, which is a hallmark of L. pneumophila infection. Similar to its defects in intracellular growth, the ΔsidE mutant no longer recruited GFP-HDEL to its vacuoles, even at 10 h post infection (FIG. 2C, 2D and FIGS. 5B, 5C). Again, SdeA but not $SdeA_{E/A}$ complemented such defects (FIGS. 2C, 2D). Thus, the putative mART motif is important for the function of the SidEs during bacterial infection.

Figure 3A:
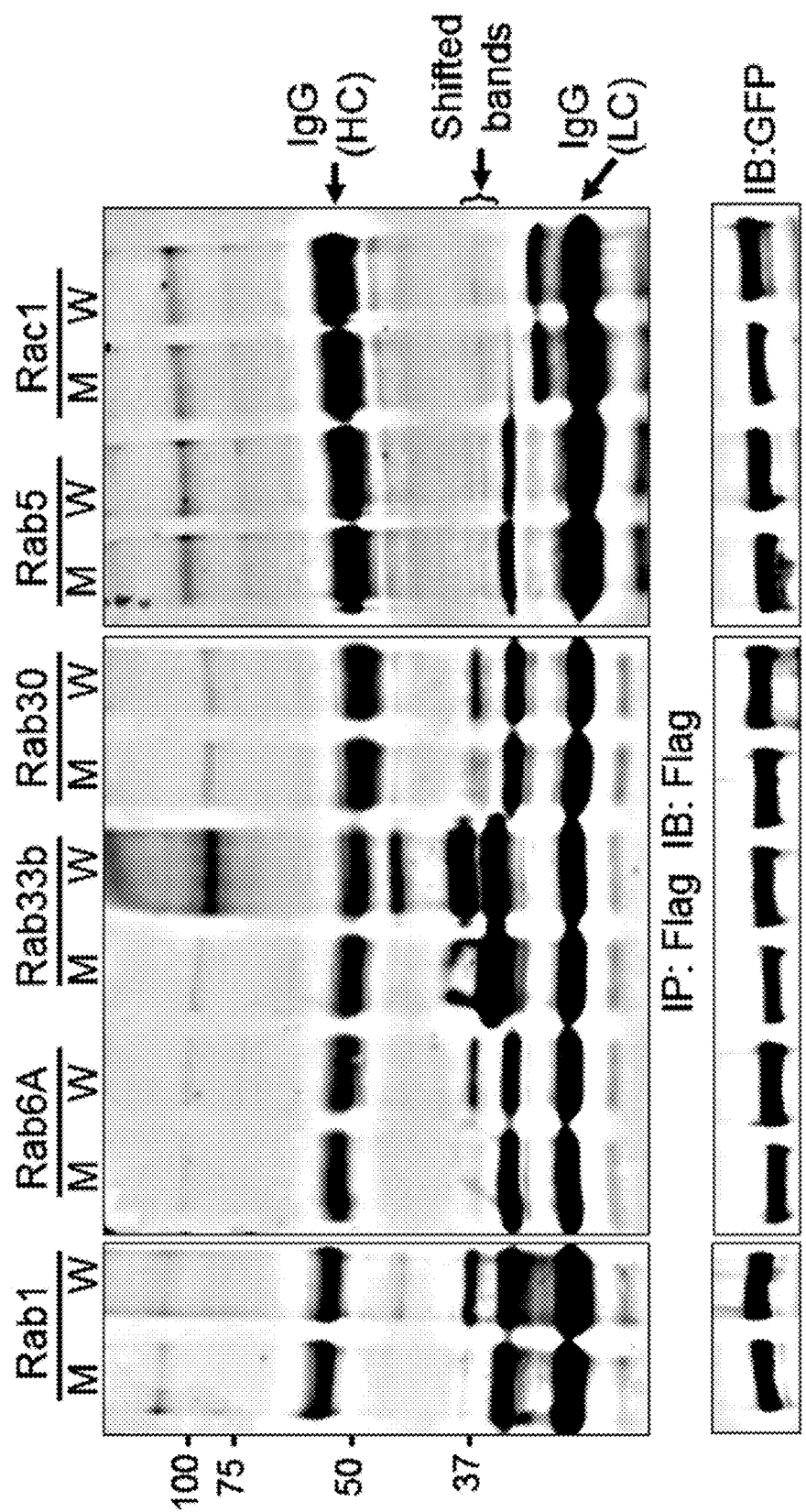
FIGS. 3A-3G show SdeA induces a posttranslational modification on multiple ER-associated Rab proteins.
Figure 3B:
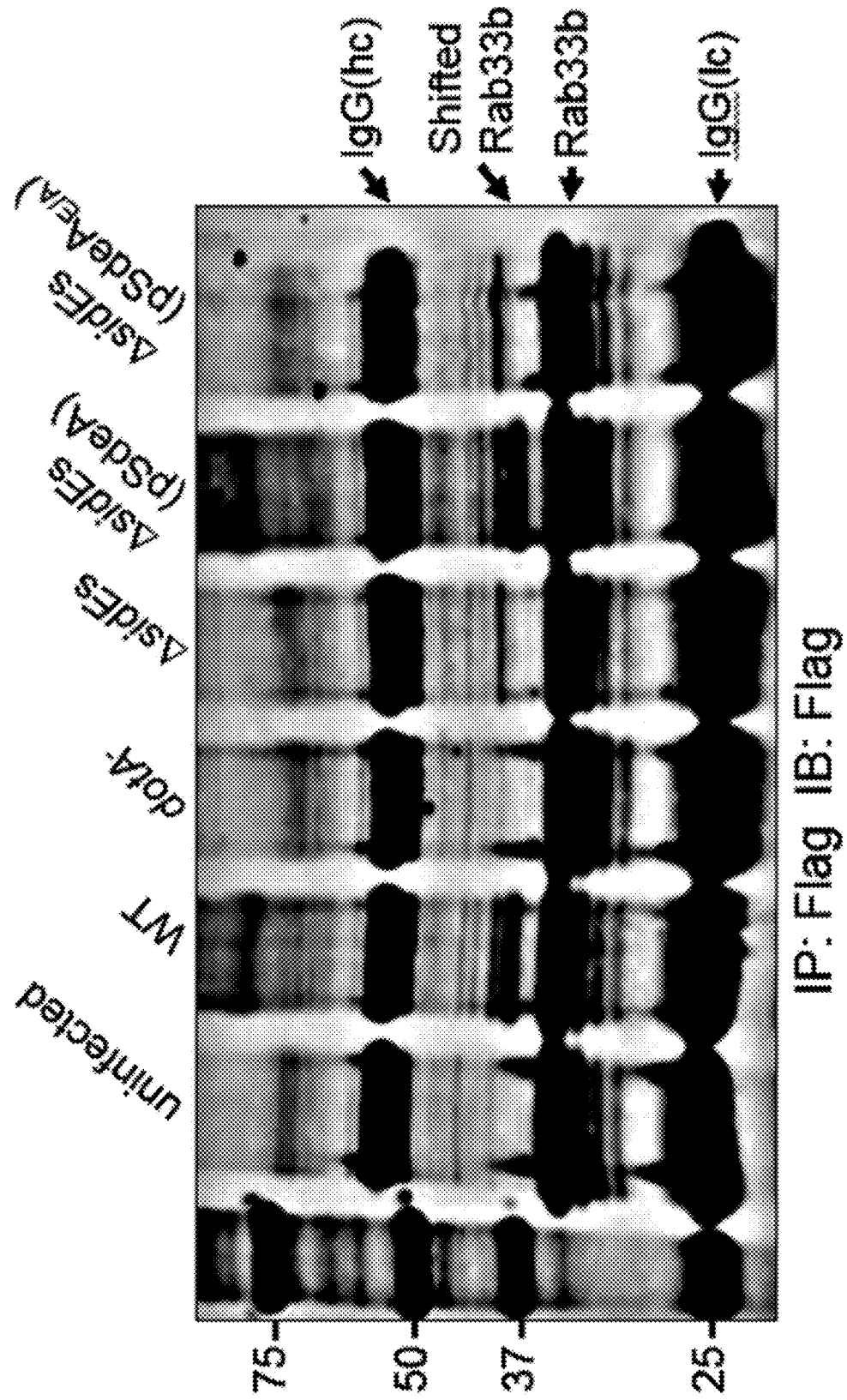
Figure 6:
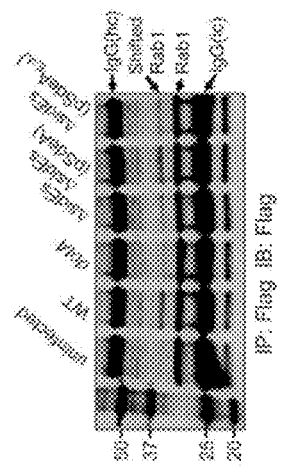
FIGS. 6A-6C | SdeA does not ADP-ribosylate mammalian proteins, the modification of Rab33b by other members of the SidE family and SdeA-mediated post-translational modification of Rab1 during bacterial infection. 6A, SdeA, Sde$_{E/A}$ or ExoS and 5 µCi $^{32}$P-NAD were added to 100 µg total protein of 293T cells. After incubation at 22° C. for 1 h, samples were separated by SDS-PAGE. Gels were stained with Coomassie brilliant blue (left panel) and then by autoradiography for the indicated time duration (middle and right panels). In samples receiving SdeA, no ADP-ribosylation signal was detected in many experiments performed in various reaction conditions. Lane 1: $^{32}$P-α-NAD+SdeA+293T lysates; lane 2: $^{32}$P-α-NAD+SdeA$_{E/A}$+293T lysates; lane 3: no sample; lane 4: $^{32}$P-α-NAD+ExoS$_{78-453}$+FAS+293T lysates. 6B, Flag-tagged Rab33b was co-expressed with GFP-tagged testing proteins in 293T cells for 24 h. Cell lysates were subjected to immunoprecipitation with Flag beads and the precipitated products were probed with the Flag antibody (right panel). 5% of each lysate was probed for the expression of Rab33b (left panel) or for GFP fusions (middle panel). Proteins used: 1, GFP; 2, GFP-SdeB$_{1-1751}$; 3, GFP-SdeC; 4, GFP-SidE. 6C, 293T cells transfected to express Flag-Rab1 were infected with the indicated *L. pneumophila* strains for 2 h and the Rab1 enriched by immunoprecipitation was probed by immunoblotting. For all panels, similar results were obtained from three experiments. 6A-6C.
Figure 6:
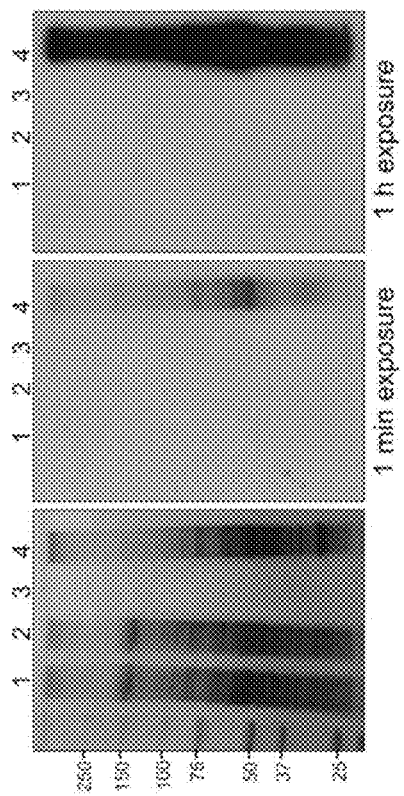
Figure 6:
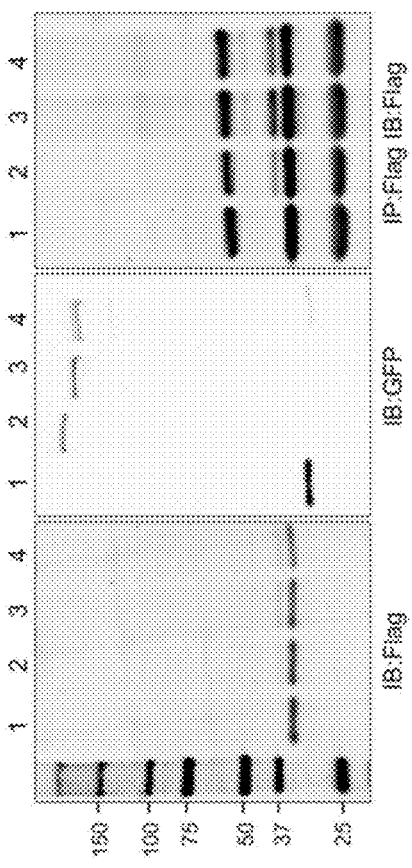

Next we attempted to determine the potential ADP-ribosyltransferase activity of SdeA. Despite extensive efforts, we were unable to detect SdeA-mediated ADP-ribosylation of eukaryotic proteins (FIG. 6A), suggesting that this protein possesses a different biochemical activity. During L. pneumophila infection, members of the SidE family are transiently associated with the LCV, an organelle resembling the ER. Because Rab small GTPases are a common target of L. pneumophila effectors, we examined whether SdeA attacks any of the ER-associated Rab proteins by co-expressing 4×Flag-tagged Rab1, Rab6A, Rab30 or Rab33b with this effector in mammalian cells. A clear shift in molecular weight was observed for all four Rab proteins purified from cells co-transfected with SdeA but not $SdeA_{E/A}$ (FIG. 3A, left and middle panels). Such a molecular weight shift did not occur for the endosomal Rab5 or the cytoskeletal small GTPase Rac1 (FIG. 3A, right panel), indicating potential substrate specificity. Among the proteins potentially modified by SdeA, the modification of Rab33b was the most extensive, suggesting that this protein is a preferred substrate. The molecular weight shift in Rab33b also was observed when it was co-expressed with other members of the SidE family (FIG. 6B). To determine whether the potential post-translational modification occurs during bacterial infection, we infected mammalian cells expressing 4×Flag-Rab33b with L. pneumophila. Rab33b of higher molecular weight was detected in samples infected with the wild-type strain but not with strains lacking the Dot/Icm transporter or the SidE family (FIG. 3B). The defect in Rab33b modification exhibited by the ΔsidE strain can be complemented by expressing SdeA but not SdeAE/A (FIG. 3B). A similar SidE-dependent molecular weight shift also occurred to Rab1 during bacterial infection (FIG. 6C). Thus, SdeA induces a biochemical modification of multiple ER-associated Rabs, and at least Rab33b and Rab1 are substrates during bacterial infection.

Figures 3C, 3D:
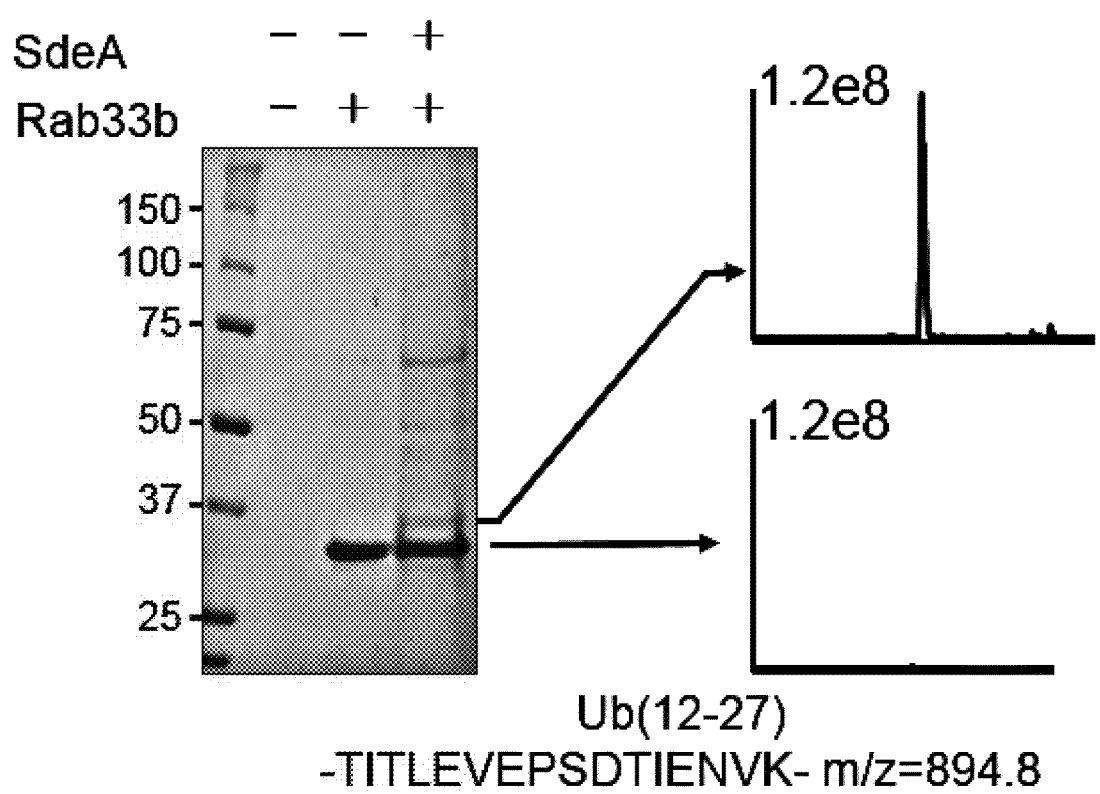
Figures 3E, 3F:
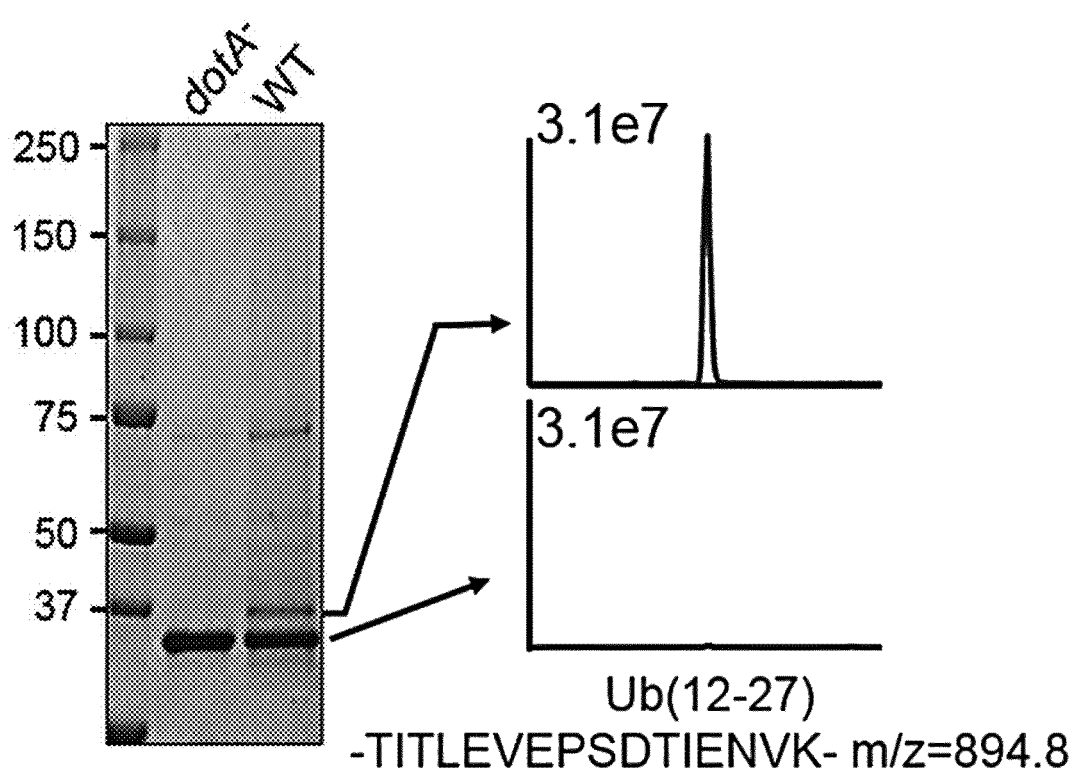
Figure 3G:
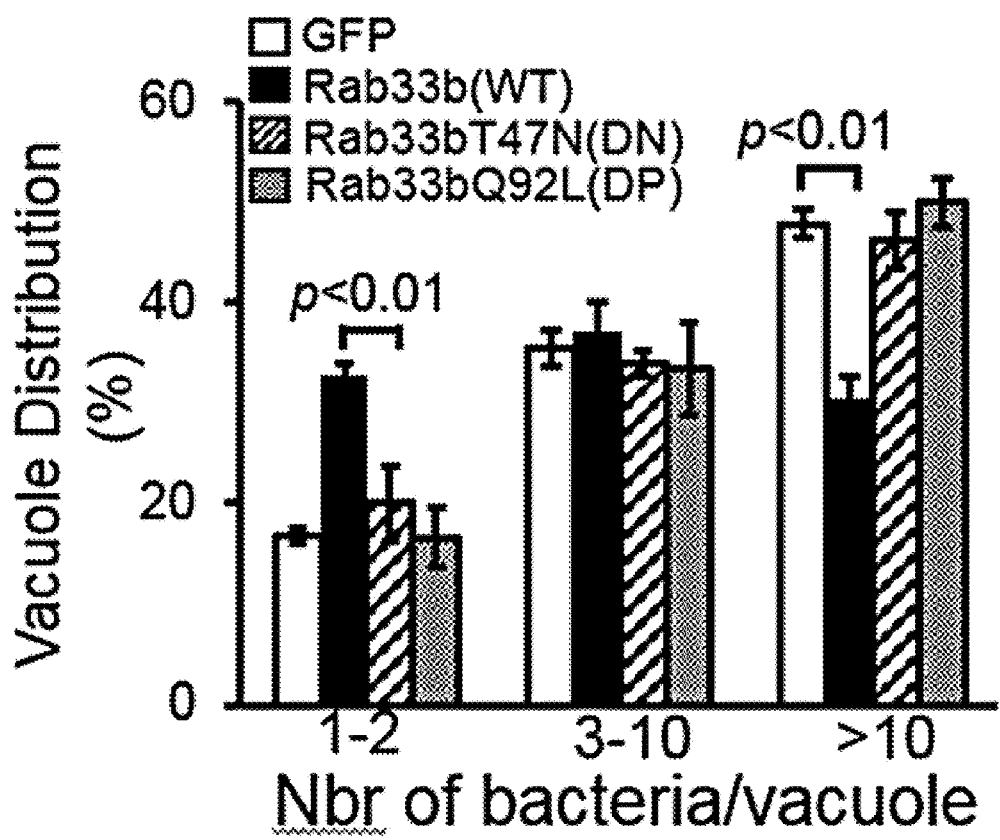
Figure 7:
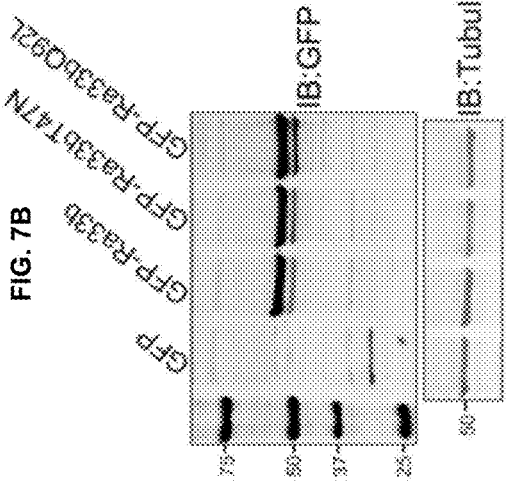
FIGS. 7A-7C | The extracted ion chromatograms of ubiquitin tryptic fragments detected by mass spectrometry, expression of Rab33b and its mutants in COS1 cells, and in vitro ubiquitination of Rab33b by SdeA with E1 and a series of E2 proteins. 7A, Proteins in bands corresponding to normal (upper panel) or shifted Rab33b (lower panel) were digested with trypsin and the resulting protein fragments were identified by mass spectrometry. Note that the ubiquitin tryptic fragments are present only in the shifted band of higher molecular weight. 7B, COS1 cells were transfected with GFP or GFP fusion of Rab33b or its mutants for 14 h. Total cell lysates resolved by SDS-PAGE were probed with a GFP-specific antibody. Tubulin was detected as a loading control. 7C, Reactions containing E1 and the indicated E2 proteins were allowed to proceed at 37° C. for 2 h. Proteins in the reactions were resolved by SDS-PAGE followed by immunoblotting to detect ubiquitinated proteins with higher molecular weight (left panel). SdeA in the reaction was detected with specific antibodies by using 10% of the reactions (lower panel). Control reactions with wild-type *Legionella* E3 ligase SidC$_{1-542}$ and its enzymatically inactive mutant SidC$_{1-542C46A}$ with E1 and the E2 UbcH7 were established to monitor the activity of E1 (right panel). Note the robust self-ubiquitination of SidC$_{1-542}$ (2nd lane right panel). Results in 3a are representative of three experiments with similar results; 7B and 7C are a representative of two and five independent experiments, respectively. 7B, 7C FIGS. 8A-8C | The activity of EDTA-dialysed SdeA and other members of the SidE family. 8A, SdeA or SdeA$_{E/A}$ dialysed against a buffer containing 10 mM EDTA was used for in vitro ubiquitination of Rab33b. Reactions were allowed to proceed for 2 h at 37° C. Samples resolved by SDS-PAGE were detected by Coomassie staining (upper panel), by immunoblotting with antibodies specific for ubiquitin (middle panel) or for the Flag tag (lower panel). Note that the addition of exogenous NAD is sufficient to allow SdeA-mediated ubiquitination of Rab33b (lane 2). 8B, In vitro ubiquitination of Rabs by SdeA. Reactions containing indicated proteins and NAD were allowed to proceed for 2 h at 37° C. After SDS-PAGE, ubiquitinated proteins were detected by staining 50% of the reactions resolved by SDS-PAGE with Coomassie (upper panel) or by immunoblotting with antibodies specific for ubiquitin (lower panel). Similar results were obtained from two experiments. 8C, In vitro ubiquitination of Rab33b by SidE, SdeB$_{1-1751}$ and SdeC. Indicated testing proteins were incubated with NAD, ubiquitin and Flag-Rab33b for 2 h at 37° C. Proteins resolved by SDS-PAGE were detected by antibodies specific for Flag (upper panel) or for ubiquitin (middle panel). His$_6$-tagged SdeA, SdeB$_{1-1751}$ and SdeC and SdeA$_{E/A}$ used in the reactions were probed 10% of the proteins with an antibody against His (lower panel). Similar results were obtained from two independent experiments. 8A-8C.
Figure 7:
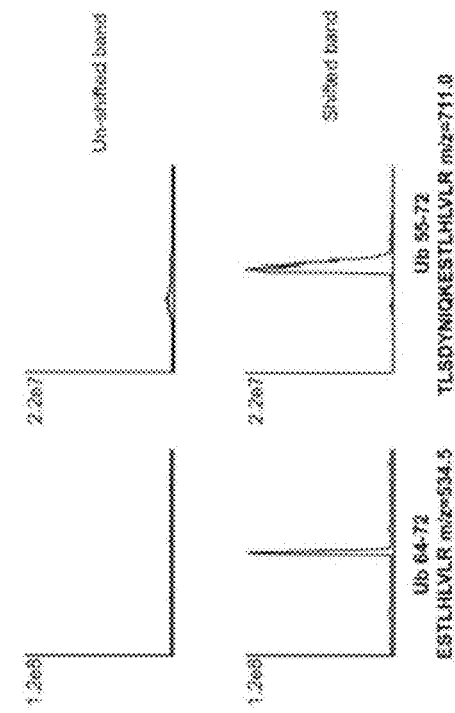
Figure 7:
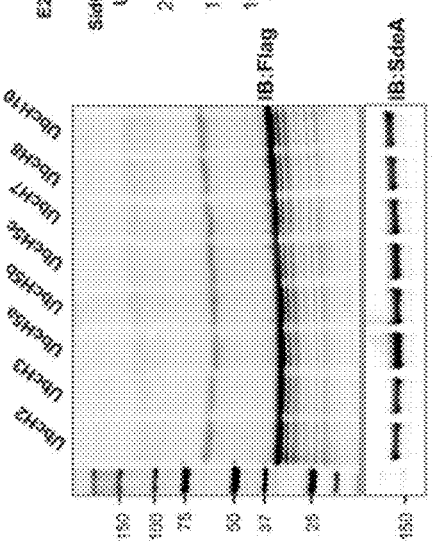

We next determined the nature of the SdeA-induced post-translational modification by mass spectrometric analysis of 4×Flag-Rab33b purified from 293T cells expressing SdeA. Ubiquitin fragments were only detected in Rab33b of higher molecular weight (FIGS. 3C, 3D and FIG. 7A). Similar results were obtained in Rab33b from cells infected with wild-type L. pneumophila (FIGS. 3E, 3F). These results suggest that Rab33b is involved in the formation of the LCV and that SdeA induces ubiquitination of Rab33b in a process that requires the putative mART motif. Indeed, overexpression of wild type Rab33b but not its dominant negative or dominant positive mutants, inhibits the formation of vacuoles containing large number (>10) of bacteria (FIG. 3G and FIG. 7B).

Figure 4A:
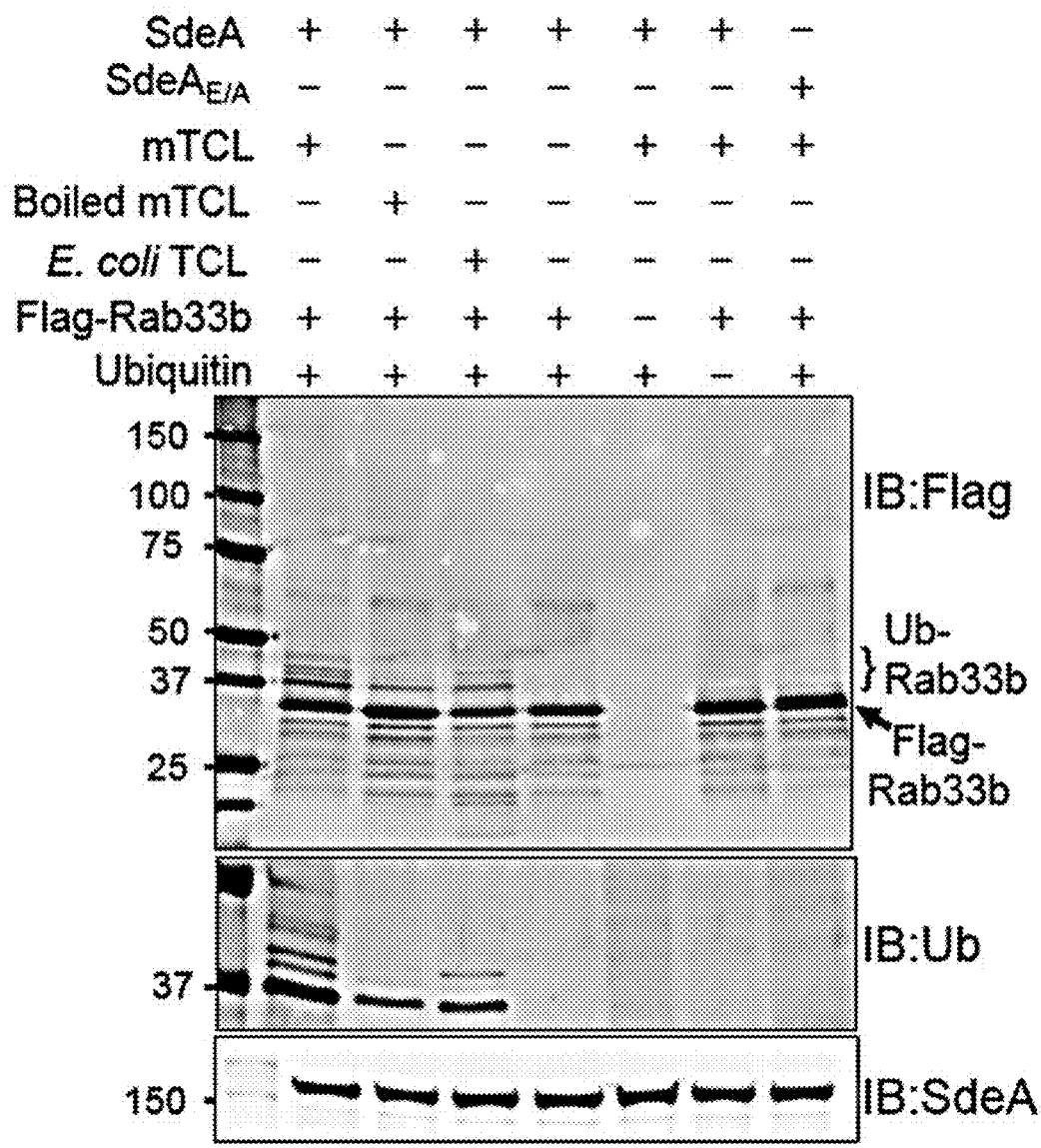
FIGS. 4A-4D show SdeA catalyses ubiquitination independent of E1 and E2.

Ubiquitination requires enzymes E1, E2 and E3 which activates, conjugates and transfers the ubiquitin molecule to the substrate, respectively. We thus used in vitro reactions to determine whether SdeA directly participates in the ubiquitination of Rab33b. In a series of reactions each containing E1 and one of several E2 enzymes, no ubiquitination of Rab33b was detected (FIG. 7c). We thus tested the hypothesis that an unknown E2 is required for the activity of SdeA by adding cell lysates to the reactions, which led to ubiquitination of Rab33b in an mART-dependent manner (FIG. 4A). Unexpectedly, ubiquitination still occurred in reactions receiving heat-treated cell lysates (FIG. 4A, lane 3), suggesting that both E1 and the putative SdeA-specific E2 are heat-stable or that SdeA is able to catalyse ubiquitination by itself but only in the presence of heat-stable molecule(s) from cells. To distinguish between these two possibilities, we added E. coli lysates to the reaction. Notably, ubiquitination of Rab33b did occur (FIG. 4A, lane 4). These results demonstrate that SdeA catalyses E1/E2-independent ubiquitination in a process that requires one or more heat-stable molecules present in cells.

Figure 4B:
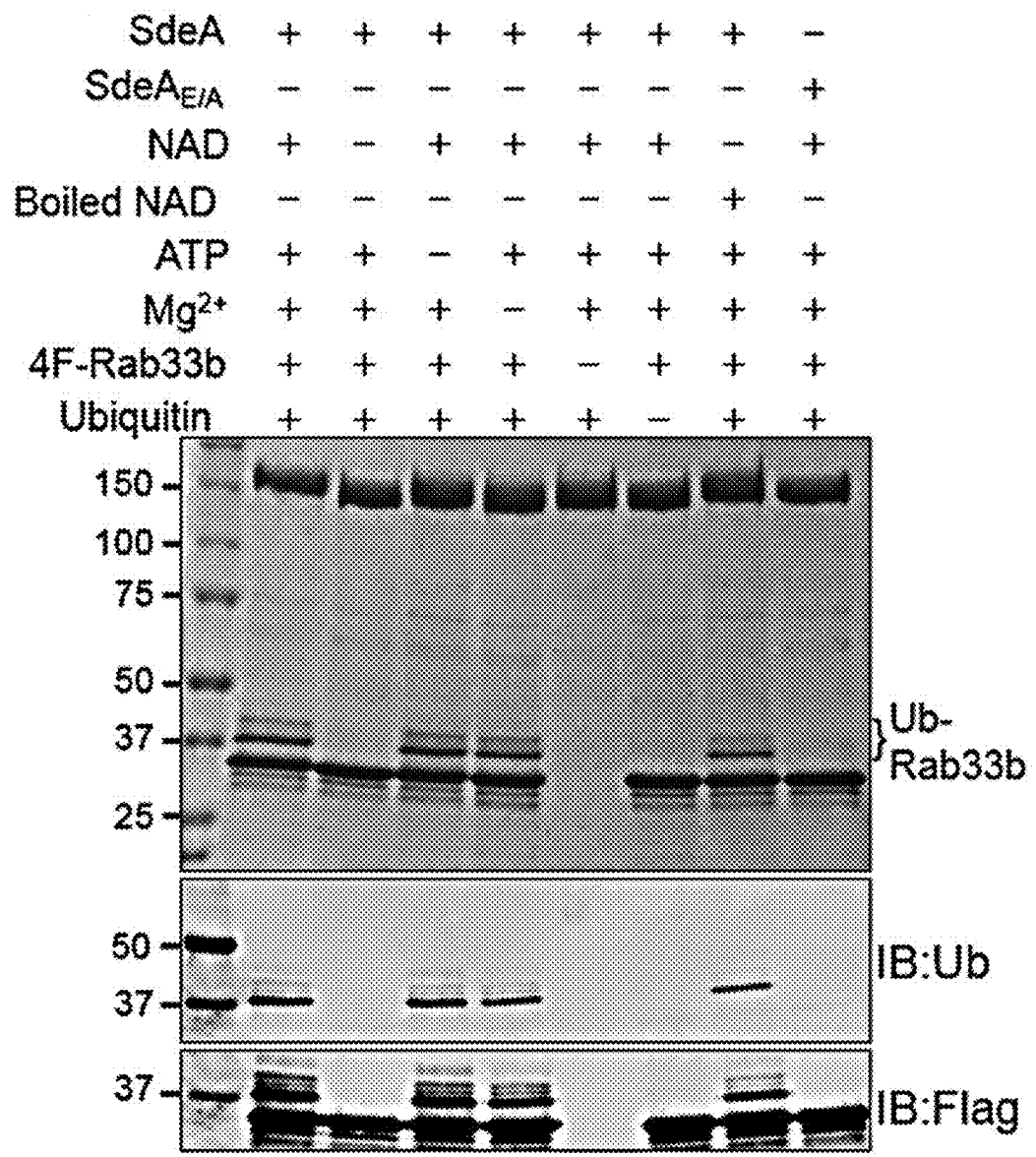
Figure 8:
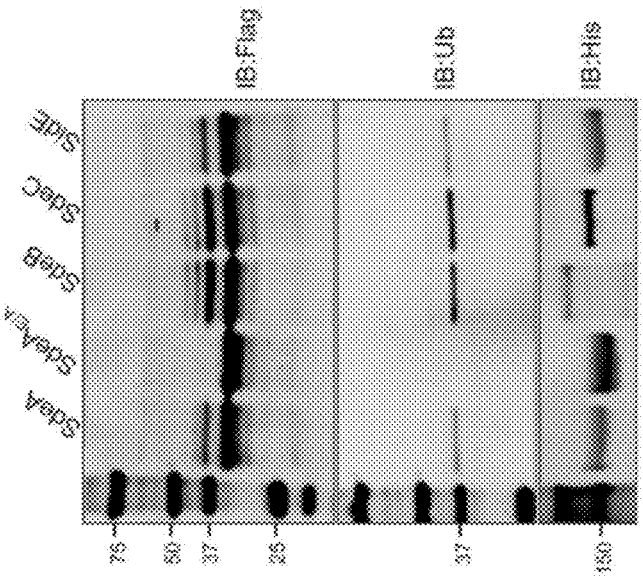
Figure 8:
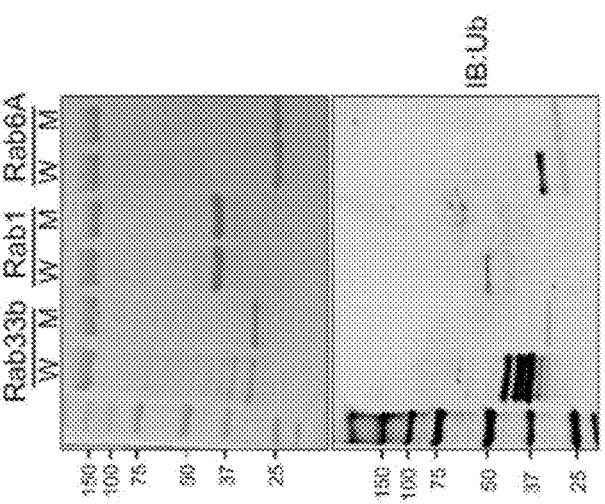
Figure 8:
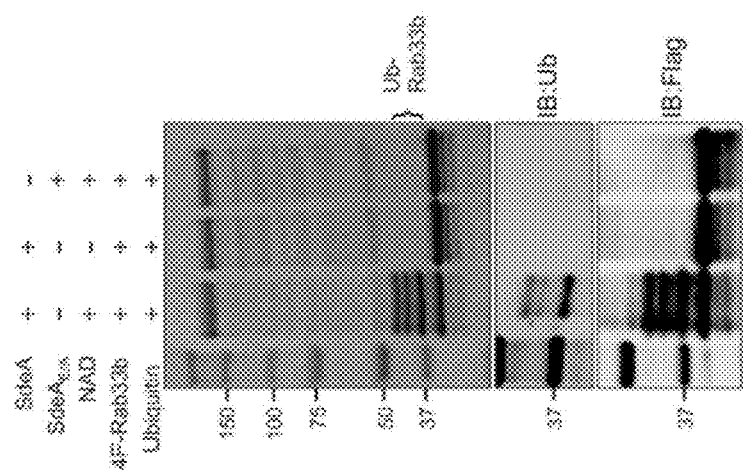
Figure 9:
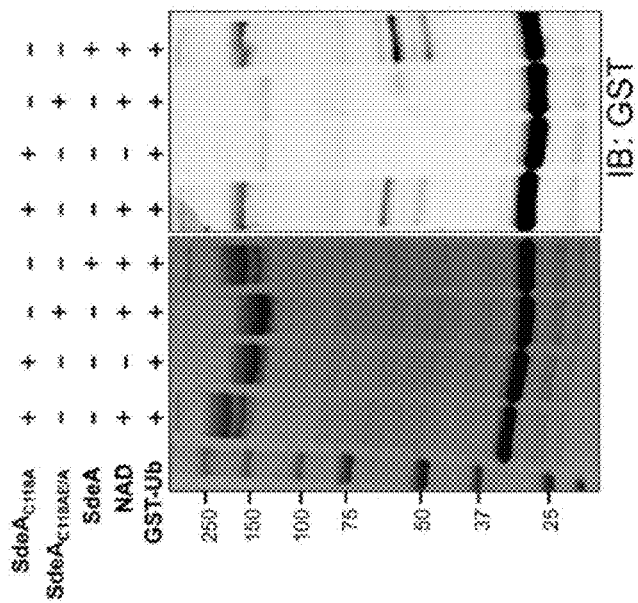
FIGS. 9A-9C | SdeA does not detectably ADP-ribosylate Rab33b or Rab1 and the deubiquitinase (DUB) activity of SdeA does not interfere with its ubiquitin-conjugation activity. 9A, 5 µg of SdeA or SdeA$_{E/A}$ were incubated with 5 µg of GST-Rab1, 4×Flag-Rab33b and 5 µCi of $^{32}$P-α-NAD. A reaction containing 200 ng of ExoS$_{78-453}$, 2 µg of FAS and 5 µg Rab5 was established as a positive control. All reactions were allowed to proceed for 1 h at 22° C. before being terminated by adding 5×SDS loading buffer. Samples resolved by SDS-PAGE were detected by Coomassie staining (upper panel) and then by autoradiography (middle and lower panels). Lane 1: $^{32}$P-α-NAD+SdeA+GST-Rab1; lane 2: $^{32}$P-α-NAD+SdeA$_{E/A}$+GST-Rab1; lane 3: $^{32}$P-α-NAD+SdeA+4×Flag-Rab33b; lane 4: $^{32}$P-α-NAD+SdeA$_{E/A}$+4×Flag-Rab33b; lane 5: no sample; lane 6: $^{32}$P-α-NAD+EXOS$_{78-453}$+FAS+Rab5. Note the strong ADP-ribosylation signals in the reaction with ExoS$_{78-453}$ (lane 6). 9B, SdeA, its mutants SdeA$_{C118A}$ or SdeA$_{C118AE/A}$ was used for in vitro NAD-dependent ubiquitination of Rab33b. Reactions containing the indicated components were allowed to proceed for 2 h at 37° C. before being terminated with SDS sample buffer. Samples resolved by SDS-PAGE were probed by Coomassie staining (upper panel) or by immunoblotting with antibody specific for ubiquitin (middle panel) or for the Flag tag (lower panel). 9C, Reactions containing GST-ubiquitin were similarly established to detect self-ubiquitination by SdeA. Note that SdeA and SdeA$_{C118A}$ exhibited similar activity in these reactions. Data in all panels are one representative of two independent experiments with similar results. 9A-9C.
Figure 9:
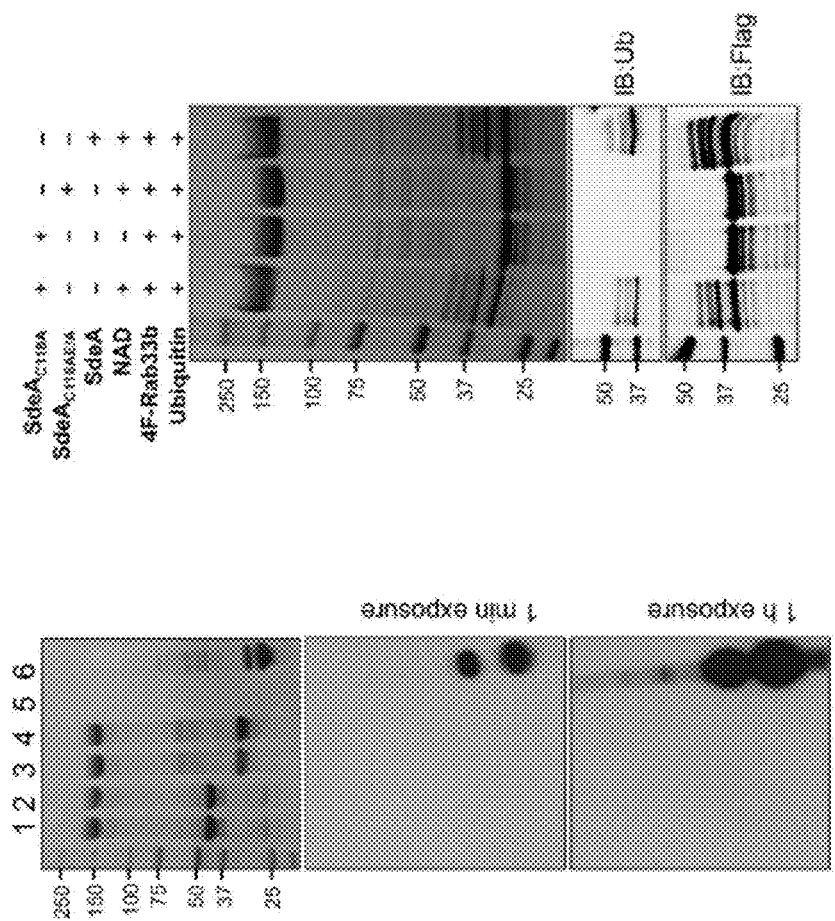

Classic ubiquitination requires the conserved E1 that activates ubiquitin in a process powered by hydrolysis of ATP, which binds the enzyme in a $Mg^{2+}$-dependent manner. We thus determined the requirement of these molecules in SdeA-mediated ubiquitination. Because of the importance of the mART motif in the cleavage of NAD by canonical ADP-ribosyltransferases, we included this compound in our reactions. In reactions containing NAD, $Mg^{2+}$ and ATP, ubiquitination of Rab33b occurred (FIG. 4B, lane 2). Yet, when NAD was withdrawn, no ubiquitination was detected (FIG. 4B, lane 3). In line with this observation, ubiquitination occurred in reactions containing NAD but not ATP or $Mg^{2+}$ (FIG. 4B, lanes 4 and 5). Heat-treated NAD is active, which is consistent with the fact that boiled cell lysates allowed SdeA to function (FIG. 4B, lane 8). Exogenous NAD is sufficient for the activity of SdeA that had been dialysed against a buffer containing EDTA (FIG. 8A), suggesting that this compound is the only co-factor required for the activity. SdeAE/A is unable to catalyse the modification even in the presence of NAD (FIG. 4B, lane 9). Under this condition, both Rab1 and Rab6A were ubiquitinated by SdeA (FIG. 8B). Similarly, SidE, SdeB and SdeC ubiquitinated Rab33b (FIG. 8C). Consistently, SdeA does not detectably ADP-ribosylate Rab33b or Rab1 (FIG. 9A).

Figure 4C:
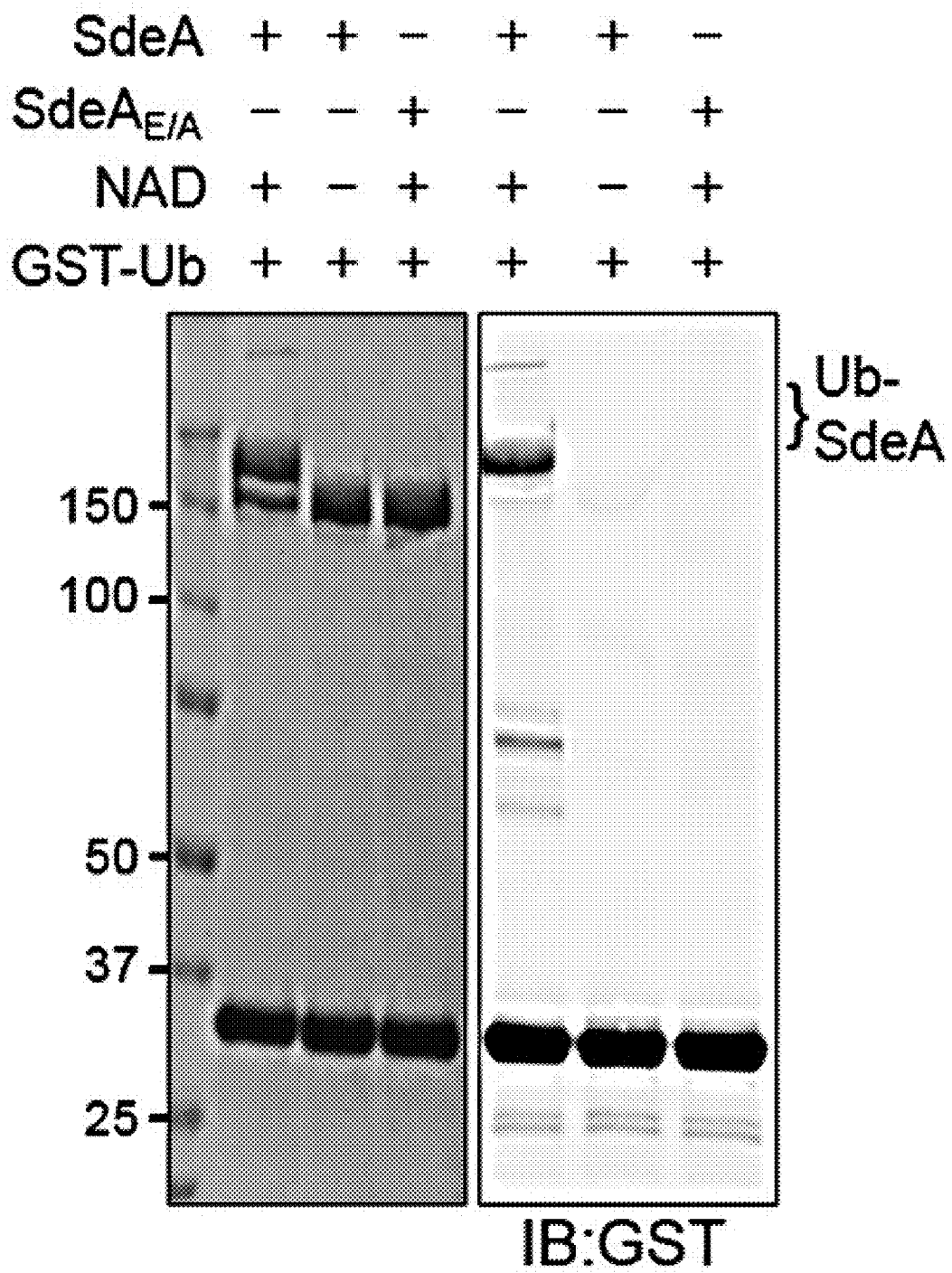
Figure 4D:
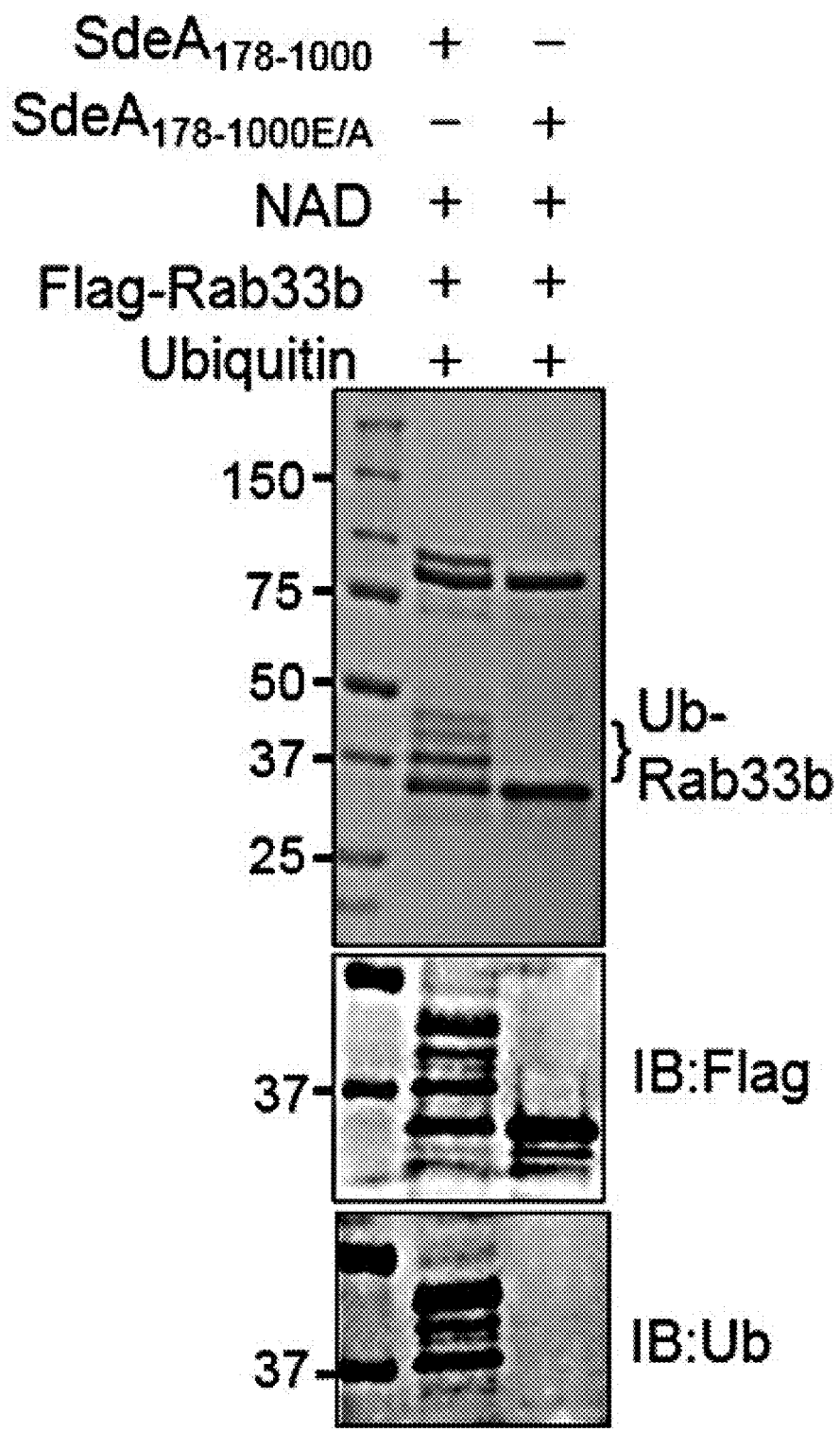

Since ubiquitin ligases often self-modify, we incubated SdeA with GST-ubiquitin to probe such self-ubiquitination. Proteins of higher molecular weight were detected in reactions containing SdeA but not SdeAE/A, again in a NAD-dependent manner (FIG. 4C). The central domain of SdeA remains toxic to yeast, suggesting that it is still biochemically active. Indeed, $SdeA_{178-1000}$ robustly ubiquitinates itself and Rab33b in a manner that requires both NAD and the mART motif (FIG. 4D). These results demonstrate that the N-terminal deubiquitinase (DUB) domain of SdeA does not interfere with its ubiquitin conjugation activity. Indeed, the $SdeA_{C1184}$ mutant defective in the DUB activity catalyses ubiquitination indistinguishably to that of the wild-type protein (FIGS. 9B, 9C).

Figure 10:
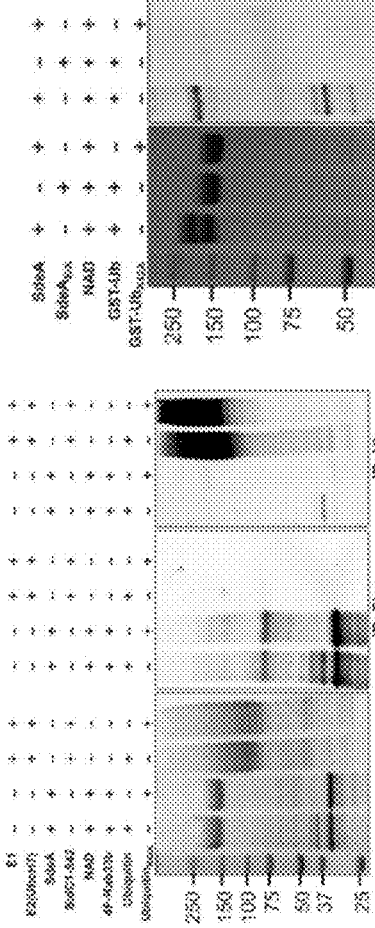
FIGS. 10A-10E | The reactivity of ubiquitin mutants in SdeA-mediated ubiquitination. 10A, Arg42 in ubiquitin is important for SdeA-mediated ubiquitination. Ubiquitin or ubiquitin$_{R42A}$ was included in reactions catalysed by SdeA or the bacterial E3 ubiquitin ligase SidC (E1 and the E2 UbcH7 were added in the latter category of reactions). After allowing the reaction to proceed for 2 h at 37° C. Samples separated by SDS-PAGE were probed with antibody against the Flag tag (on Rab33b) (middle panel) or ubiquitin (right panel). Note that ubiquitin$_{R42A}$ can be used by ubiquitination catalysed by SidC but not SdeA. 10B, GST-ubiquitin$_{R42A}$ cannot be used for self-ubiquitination by SdeA. GST-ubiquitin or GST-ubiquitin$_{R42A}$ was used in reactions with SdeA or SdeA$_{E/A}$. Self-modification was detected by the shift of SdeA detected by Coomassie staining (left panel) or by immunoblotting with a GST-specific antibody (right panel). 10C, The lysine residues or the carboxyl terminus of ubiquitin is not important for SdeA-catalysed Rab33b ubiquitination. Reactions containing SdeA or SdeA$_{E/A}$, NAD, Flag-Rab33b and the indicated ubiquitin mutants were allowed to proceed for 2 h at 37° C. Proteins were detected by Coomassie staining (upper panel) or probed by immunoblotting with antibody against ubiquitin. 10D, Utilization of the ubiquitin di-glycine mutant by different ligases. Reactions with indicated components were allowed to proceed for 2 h at 37° C. Proteins resolved by SDS-PAGE were detected by staining (upper panel) or by immunoblotting with antibodies specific to ubiquitin (lower panel). Note that the wild type but not the di-glycine ubiquitin mutant (AA) can be conjugated to proteins in a reaction containing E1 and E2 and the bacterial E3 ligase SidC (Lanes 6 and 7). This di-glycine mutant (AA) can still be attached to Rab33b by SdeA (Lane 4). 10E, Addition of 6 histidine residues to the carboxyl end of ubiquitin did not affect SdeA-mediated ubiquitination. Reactions containing the indicated components were established and allowed to proceed for 2 h at 37° C. SDS-PAGE resolved samples were probed by Coomassie staining (left panel) or by immunoblotting with a GST-specific antibody (right panel). The data in all panels are one representative of three independent experiments with similar results. 10A-10E.
Figure 10:
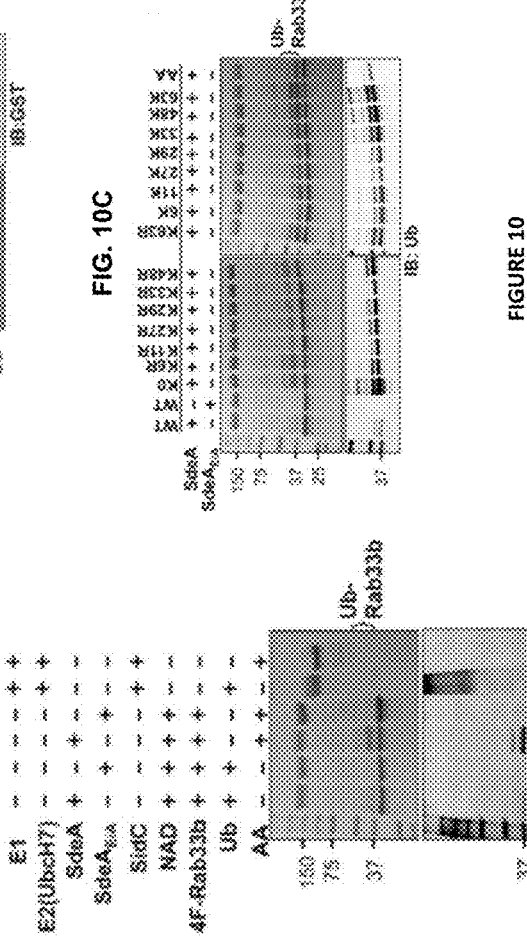
Figure 10:
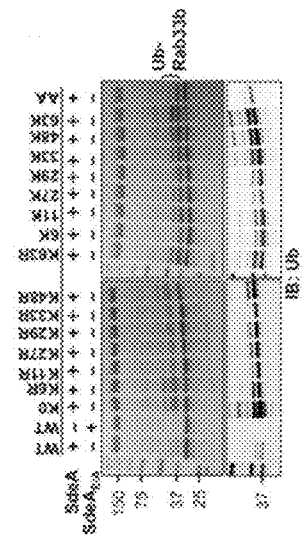
Figure 10:
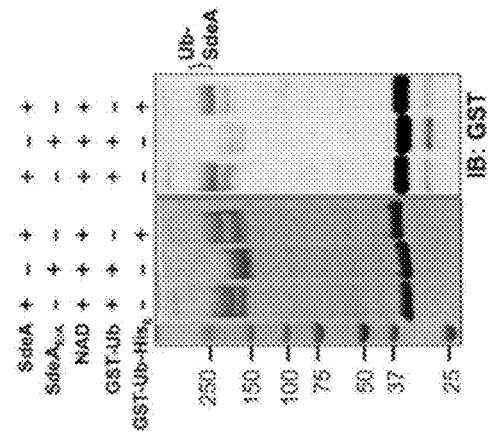
Figure 11:
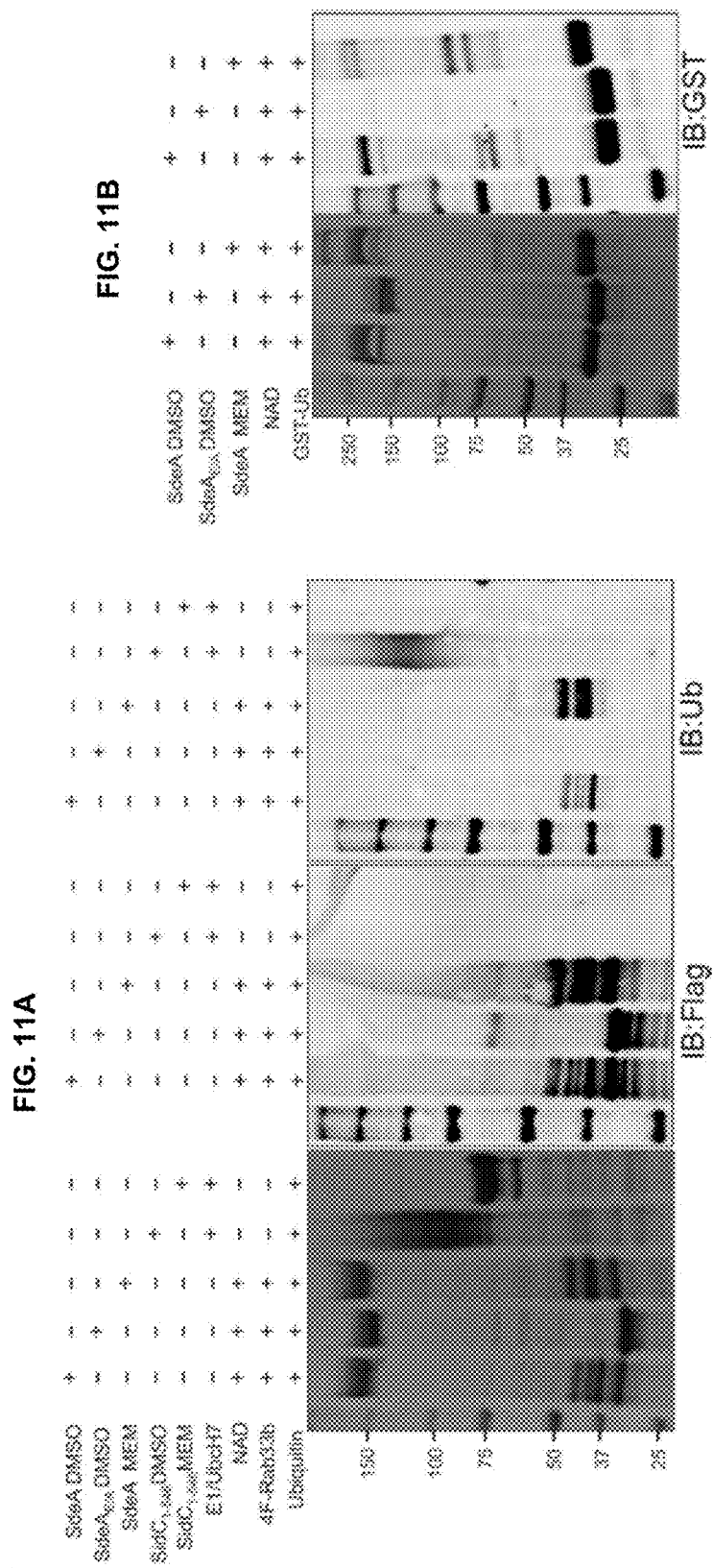
FIGS. 11A and 11B | Ubiquitination catalysed by SdeA is insensitive to the cysteine modifying agent maleimide. 11A, Ubiquitination reactions by SdeA or SidC together with E1 and E2 were established; maleimide was added to 50 μM to a subset of these reactions. After incubation at 37° C. for 2 h, ubiquitination was detected by Coomassie staining (left panel) or by immunoblotting with the Flag- (middle panel) or ubiquitin-specific (right) antibody. Note that maleimide completely inhibits ubiquitination in the reaction catalysed by SidC, E1 and its cognate and E2 (lane 6) but does not affect the activity of SdeA (lane 4). 11B, Maleimide does not affect self-ubiquitination of SdeA. Reactions containing the indicated components were established and the modification of SdeA was probed by Coomassie staining (left panel) or by immunoblotting with the GST-specific antibody (right panel). For all panels, similar results were obtained from four independent experiments. 11A, 11B.
Figure 12:
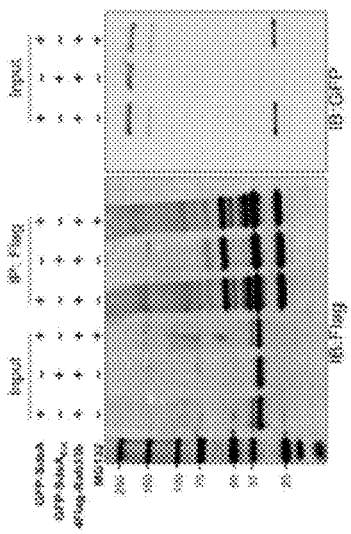
FIGS. 12A-12E | SdeA-mediated ubiquitination affects the activity but not stability of Rab33b and SdeA ubiquitinates Rab33b independently of its nucleotide binding status. 12A, Evaluation of the ubiquitinated Rab33b. 4×Flag-Rab33b was loaded with unlabelled GDP (5 mM) before ubiquitination reaction. GDP-loaded Rab33b was subjected to ubiquitination by SdeA or SdeA$_{E/A}$ for 2 h at 37° C.; 20% of the samples were withdrawn to determine the extent of ubiquitination by Coomassie staining. 12B, Ubiquitination affected the GTP loading activity of Rab33b. Ubiquitinated or non-ubiquitinated 4×Flag-Rab33b was incubated in 50 μl nucleotide exchange buffer containing 5 μCi $^{35}$SγGTP at 22° C. Aliquots of reactions were withdrawn at indicated time points and passed through nitrocellulose membrane filters. Membranes were washed for three times using exchange buffer before being transferred into scintillation vials containing scintillation fluid to detect incorporated $^{35}$SγGTP with a scintillation counter. 12C, Ubiquitination affected the GTPase activity of Rab33b. Samples withdrawn from Ub-Rab33b or Rab33b loaded with $^{32}$PγGTP were measured for the associated radioactivity to set as the starting point. Equal volumes of samples were withdrawn at the indicated time points to monitor intrinsic GTP hydrolysis. The GTP hydrolysis index was calculated by dividing the readings obtained in later time points by the values of the starting point. Similar results (12A-12C) were obtained in three independent experiments and the data shown were from one representative experiment. 12D, SdeA-mediated ubiquitination does not lead to degradation of Rab33b. GFP fusion of SdeA or SdeA$_{E/A}$ was co-transfected with Rab33b for 14 h. The proteasome inhibitor MG132 (10 μM) was added to one of the SdeA samples. The levels of Rab33b were detected by immunoblotting following immunoprecipitation with the Flag-specific antibody. Note that the addition of MG132 does not affect the level of modified Rab33b in samples co-transfected with SdeA. Similar results were obtained from two independent experiments. 12E, The nucleotide binding status of Rab33b does not affect its suitability as substrate in SdeA-mediated ubiquitination. Equal amounts of Rab33b, its dominant negative mutant Rab33b(T47N), or the dominant positive mutant Rab33b(Q92L) was incubated with SdeA. Samples withdrawn at the indicated time points were detected for ubiquitination by Coomassie staining (upper panel); 293T cells transfected to express these mutants were infected the indicated L. pneumophila strains and ubiquitinated Rab33b or its mutants were probed by molecular weight shift in Rab33b obtained by immunoprecipitation (lower panel). Data in this panel are one representative of two independent experiments with similar results. 12A, 12D, 12E.
Figure 12:
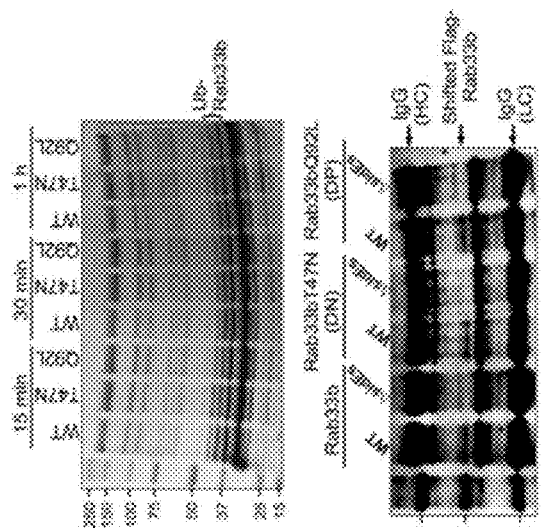
Figure 12:
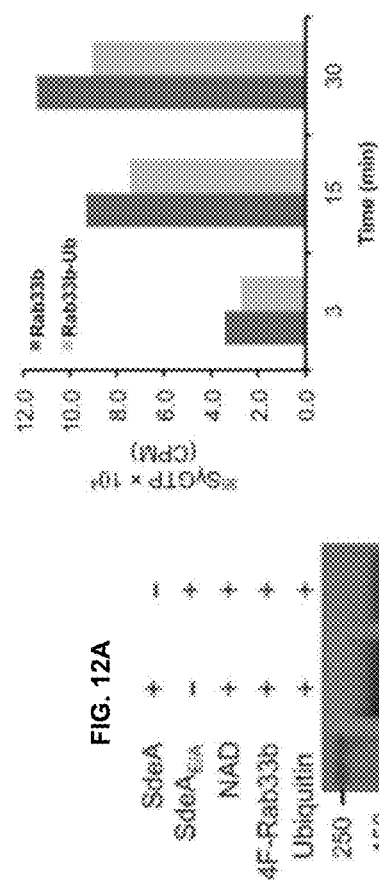
Figure 12:
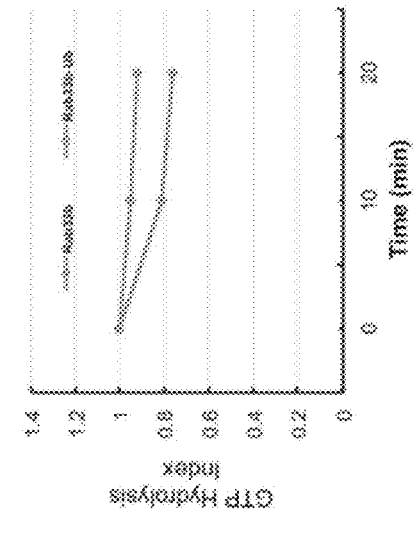

Mass spectrometric and mutational analyses revealed that Arg42 of ubiquitin is important for SdeA-mediated, but not for canonical ubiquitination catalysed by the E1-E2-E3 cascade (FIGS. 10A, 10B). Consistent with these results, SdeA ubiquitinates Rab33b with all lysine variants of ubiquitin, as well as the ubiquitin derivative containing an alanine substitution in the last two glycine residues or with six histidine residues attached to its carboxy terminus (FIGS. 10C-10E). Further, ubiquitination catalysed by SdeA is insensitive to the cysteine alkylation agent maleimide, suggesting that a cysteine conjugation of ubiquitin does not form during the reaction (FIG. 11). Finally, ubiquitination by SdeA affected the GTP loading and hydrolysis activity of Rab33b but did not detectably affect its stability (FIG. 3A and FIG. 12). The nucleotide binding status of Rab33b did not affect its suitability as the substrate of SdeA (FIG. 12E).

Figure 13:
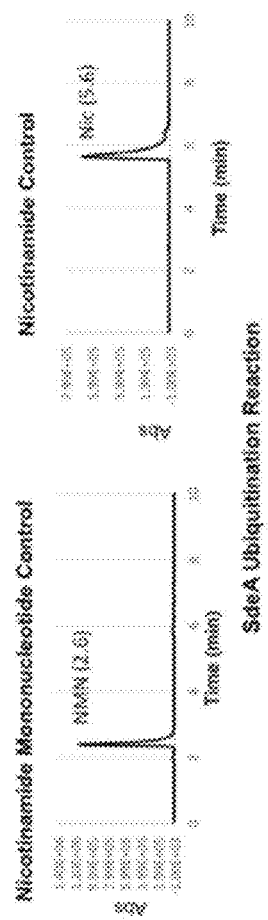
FIGS. 13A-13D | Detection of the reaction intermediates in SdeA-catalysed ubiquitination. 13A, Controls were analysed by HPLC of NAD alone and in the presence of SdeA, Ub, and SdeA and Ub. In these reactions, AMP and NAD were identified with retention times of 3.6 and 6.8 min, respectively. 13B, Both AMP (left) and NAD (right) were additionally identified by ESI mass spectrometry. Both NAD and a product in which the nicotinamide group has been lost were observed in these experiments. 13C, To determine whether other fragments are generated in this reaction, retention time for nicotinamide mononucleotide (NMN, left) and nicotinamide (Nic, right) was determined by HPLC to be 5.6 and 2.6 min respectively. 13D, To identify additional components, a reaction was set up and the individual components were identified by HPLC. In the reaction mixture, AMP (3.5 min), nicotinamide (Nic 5.5 min), and NAD (6.5 min) were observed. An additional component to the reaction mixture (labelled X) was observed (6.1 min), but could not be further identified by mass spectrometry. Data in all panels are one representative from three independent experiments with similar results.
Figure 13:
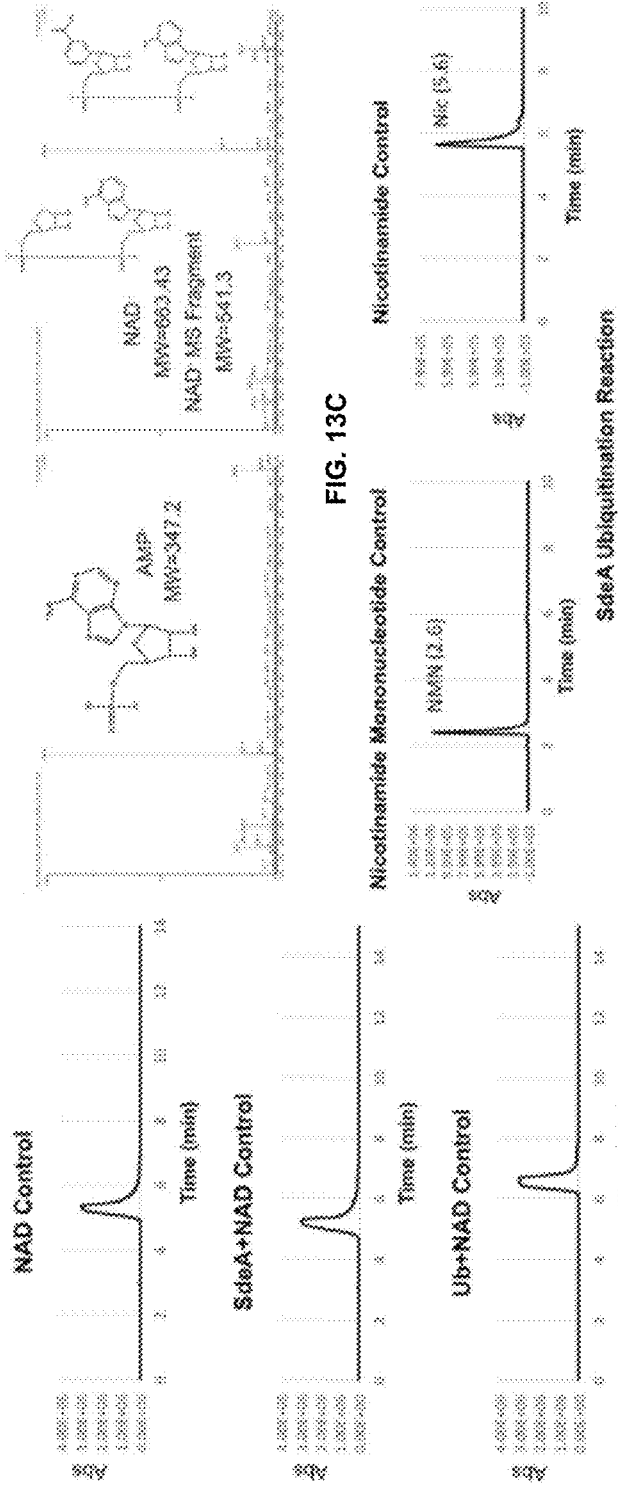
Figure 13:
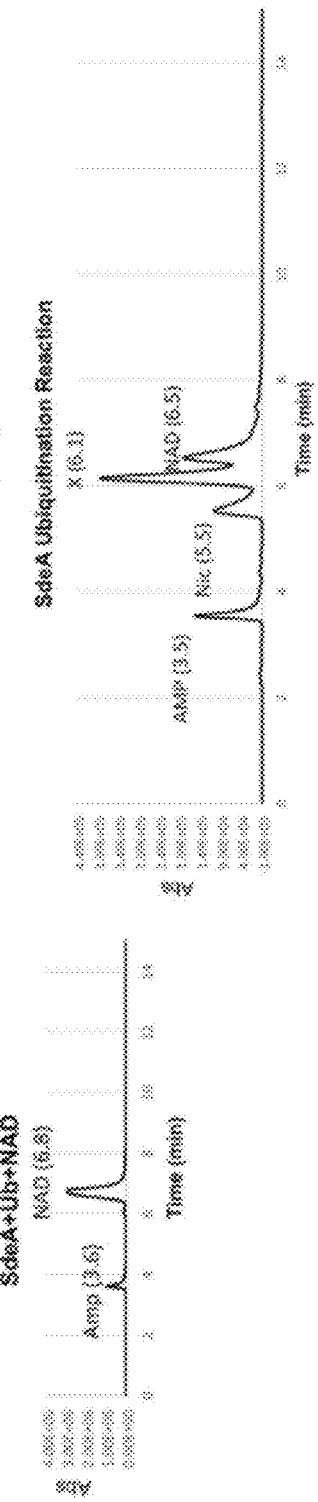
Figure 14:
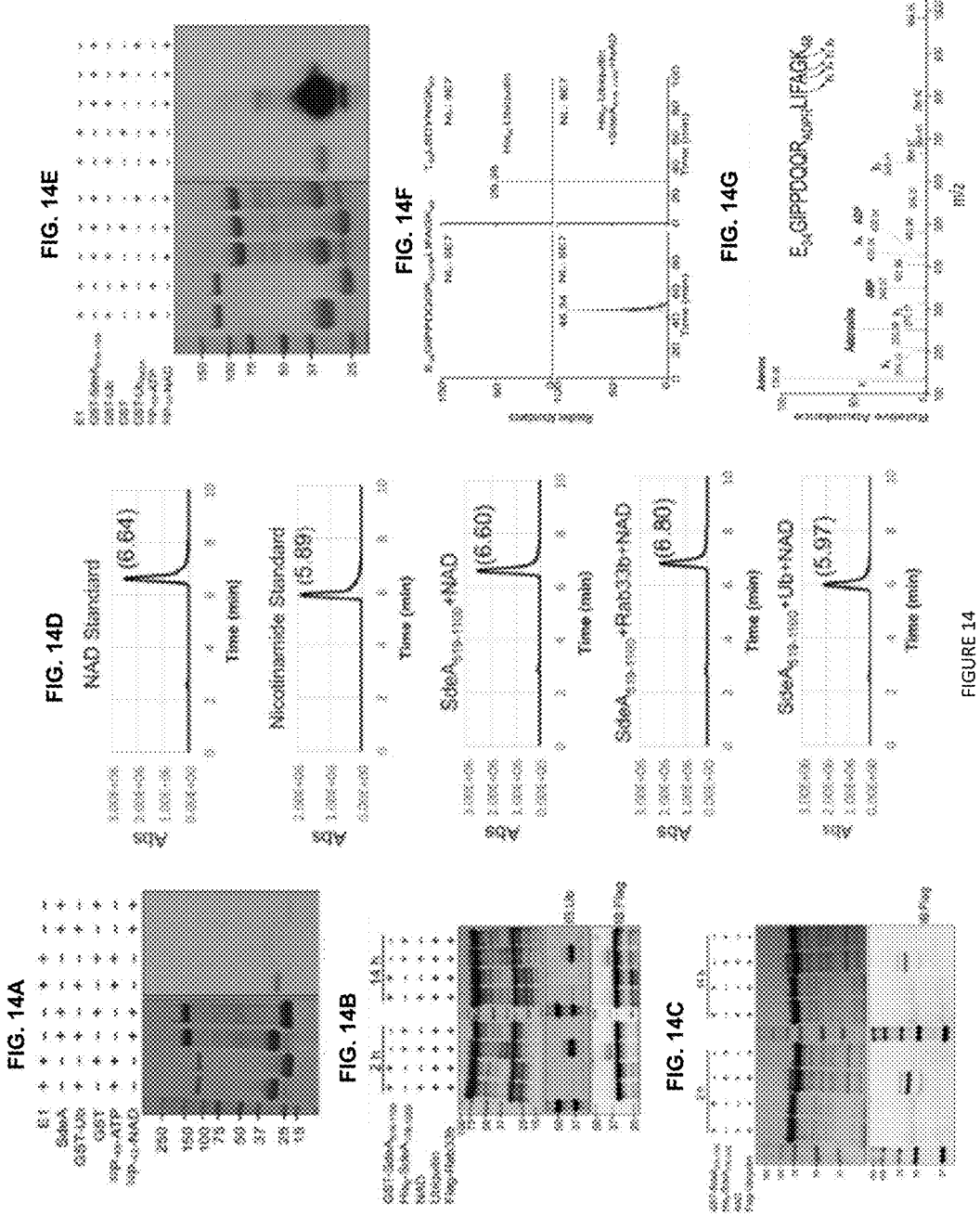
FIGS. 14A-G | Detection of the ubiquitination intermediate by using SdeA$_{519-1100}$. 14A, Full-length SdeA cannot produce $^{32}$P-labelled product in reactions using $^{32}$P-α-NAD. Reaction samples resolved by SDS-PAGE were detected by Coomassie staining (left panel) and then by autoradiography (right panel). Note the $^{32}$P-α-AMP-GST-ubiquitin complex can be detected in the reaction containing E1 but not SdeA. 14B, 14C, SdeA$_{519-1100}$ is defective in auto-ubiquitination. Reactions containing the indicated components were allowed to proceed for the indicated time duration and the production of ubiquitinated Rab33b (14B) or SdeA$_{519-1100}$ was detected by immunoblotting. 14D, SdeA$_{519-1100}$ induces the production of nicotinamide from NAD and ubiquitin. Retention time for nicotinamide and NAD was first determined by HPLC and nicotinamide can only be detected in the reaction containing SdeA$_{519-1100}$, NAD and ubiquitin. 14E, SdeA$_{519-1100}$ induces the production of $^{32}$P-ADPR-labelled ubiquitin. GST-ubiquitin or GST-ubiquitin$_{R42A}$ was incubated with $^{32}$P-α-NAD and SdeA$_{519-1100}$ for 6 h. Classical E1 incubated with GST-ubiquitin was included as a control. Samples resolved by SDS-PAGE before autoradiography (20 min) (right panel). Note that GST-ubiquitin$_{R42A}$ cannot be labelled by $^{32}$P. Data in panels 14A-14E are one representative from two independent experiments with similar results. 14F, The detection of a peptide with m/z 737.33 corresponding to the tryptic peptide E$_{34}$GIPPDQQRLIFAGK$_{48}$ containing one ADP-ribosylation site was detected only after ubiquitin was incubated with SdeA$_{519-1100}$. As a loading control, another unmodified ubiquitin peptide T$_{55}$LSDYNIQK$_{63}$ was detected in both control and treated samples. 14G, Tandem mass analysis revealed that ADP-ribosylation occurred on Arg42 evidenced by the extensive fragmentation of the ADP-ribosylation into adenine, adenosine, AMP and ADP ions. Although not as extensive, the fragmentation of the peptide backbone helps confirm the peptide sequence. Data shown in all panels are one representative from two independent experiments with similar results. 14A-14C, 14E.

We detected AMP, nicotinamide, ubiquitin and NAD in SdeA-catalysed reactions (FIG. 13). The release of AMP suggests the formation of an ubiquitin-AMP adduct during the reaction. Yet, the ubiquitin-AMP adduct could not be detected by $^{32}P$-α-NAD or by TCA precipitation followed by HPLC-MS (FIG. 14A). The release of nicotinamide and the requirement of Arg42 of ubiquitin implied ADP-ribosylation of this side chain as a possible step before ubiquitin conjugation, which is consistent with the requirement of the R-S-ExE motif found in members of the SidE protein family. Thus, we probed the reaction intermediate by obtaining SdeA519-1100, a fragment that retained the ability to modify Rab33b but had lost the self-ubiquitination activity (FIGS. 14B, 14C). Incubation of SdeA519-1100 with NAD and ubiquitin led to the release of nicotinamide (FIG. 14D), suggesting the formation of ADP-ribosylated ubiquitin. Furthermore, inclusion of $^{32}P$-α-NAD in the reaction produced $^{32}P$-labelled ubiquitin in an Arg42-dependent manner and the ADP-ribosyl moiety linked to Arg42 of ubiquitin can be detected by mass spectrometric analysis (FIGS. 14E-G). Thus, ADP-ribosylated ubiquitin is the reaction intermediate. The production of AMP in reactions with full-length SdeA could be a subsequent step in the attack of an acceptor nucleophile (from the Rab proteins or SdeA itself in the self-conjugation reaction) on the ADP-ribosylated ubiquitin leading to the modification of the target protein.

In a canonical ubiquitination reaction, ubiquitin activated by E1 is delivered to E2 to form the E2~Ub thioester. For the E3 ligases of the RING family, ubiquitin is directly transferred from the E2 to a substrate facilitated by the ligases, whereas members of the HECT and RBR E3 families transfer ubiquitin to a catalytic cysteine in the E3 before delivering it to the substrate. Clearly, SdeA defines an all-in-one ubiquitin conjugation enzyme that directly activates ubiquitin; the fact that $SdeA_{519-1100}$ defective in auto-ubiquitination can still modify Rab33b suggests that the activated ubiquitin is directly transferred to the substrate.

The discovery that ubiquitin can be modified by ADP-ribosylation expands the post-translational modification on this prevalent signaling molecule, which has been shown to be modified by acetylation and phosphorylation. This discovery can potentially lead to significant expansion of the ubiquitin code and its functions in cellular processes and disease development. The mART motif is present in a family of mammalian proteins, some of which are unable to catalyse ADP-ribosylation. In light of the mART-dependent ubiquitination activity of SdeA, it will be interesting to determine whether any of these mART-containing proteins is capable of catalysing ubiquitination, and if so, whether the reaction requires E1 and E2. The identification of eukaryotic mART proteins with such a capability allows for expansion of the spectrum of cellular processes regulated by ubiquitination.

In one aspect, the present disclosure provides a ubiquitination assay wherein the assay comprises using β-nicotinamide adenine dinucleotide (β-NAD).

In one aspect, the present disclosure provides a ubiquitination assay wherein the assay comprises using a protein capable of catalyzing ubiquitination process, wherein the protein capable of catalyzing ubiquitination process is selected from the group consisting of SdeA, SdeB, SdeC, SidE, any mutant protein of SdeA, SdeB, SdeC, or SidE, and any combination thereof.

In one aspect, the present disclosure provides a ubiquitination assay wherein the assay comprises using β-nicotinamide adenine dinucleotide (β-NAD) and a protein capable of catalyzing ubiquitination process, wherein the protein capable of catalyzing ubiquitination process is selected from the group consisting of SdeA, SdeB, SdeC, SidE, any mutant protein of SdeA, SdeB, SdeC, or SidE, and any combination thereof.

In one aspect, the present disclosure provides a composition that may be used in ubiquitination assays and/or for methods of screening active substrate that may inhibit the ubiquitination process, wherein the composition comprises:
  a). β-nicotinamide adenine dinucleotide (β-NAD);
  b). a ubiquitin or a mutant of a ubiquitin; and
  c). a protein capable of catalyzing ubiquitination process, wherein the protein capable of catalyzing ubiquitination process is selected from the group consisting of SdeA, SdeB, SdeC, SidE, any mutant protein of SdeA, SdeB, SdeC, or SidE, and any combination thereof.

A person having ordinary skill in the art may appreciate that the composition comprising a), b) and c) may comprise complicated reaction products of a), b), and c) once a), b), and c) are combined.

In one aspect, the present disclosure provides a composition that may be used in ubiquitination assays and/or for methods of screening active substrate that may inhibit the ubiquitination process, wherein the composition comprises:
  a). β-nicotinamide adenine dinucleotide (β-NAD);
  b). a ubiquitin or a mutant of a ubiquitin;
  c). a protein capable of catalyzing ubiquitination process, wherein the protein capable of catalyzingubiquitination process is selected from the group consisting of SdeA, SdeB, SdeC, SidE, any mutant protein of SdeA, SdeB, SdeC, or SidE, and any combination thereof; and
  d). an additional protein, wherein the additional protein is able to be ubiquitinated with an ubiquitin through a ribose-phosphate link.

In one aspect, the additional protein d) may be selected from the group consisting of Rab1, Rab6A, Rab30, Rab33b, Rtn4, Atlastin, any mutant of Rab1, Rab6A, Rab30, Rab33b, Rtn4, or Atlastin, and any combination thereof.

A person having ordinary skill in the art may appreciate that the compositions comprising a), b), c), and d) may comprise complicated reaction products of a), b), c), and d) once a), b), c), and d) are combined.

In one aspect, the concentration of each of a), b), c), and d) in a composition that may be used in ubiquitination assays is in the range of 0.001 μg/μL to 1000 μg/μL. In one aspect, the concentration of each of a), b), c), and d) is in the range of 0.01 μg/μL to 100 μg/μL. In one aspect, the concentration of each of a), b), c), and d) is in the range of 0.1 μg/μL to 1.0 μg/μL.

In one aspect, the present disclosure provides a method of identifying a substance capable of inhibiting the ubiquitination, wherein the method comprises adding a candidate substance at a suitable condition to a composition comprising a), b), c), and d), and examine whether the candidate substance may inhibit the ubiquitination by measuring the ubiquitinated protein d) by an analytic method such as immunoblotting.

In one aspect, a candidate substance may be a small organic molecule or an antibody raised by using the modified substrates such as Rab1, Rab6A, Rab30, Rab33b, Rtn4, Atlastin, any mutant of Rab1, Rab6A, Rab30, Rab33b, Rtn4, or Atlastin, and any combination thereof, wherein the antibody may recognize proteins ubiquitinated by mammalian proteins capable of accomplishing reactions in a way similar to SidE family.

In one aspect, the protein used for the ubiquitination in the present disclosure may be a mammalian protein.

In one aspect, the present disclosure presents a method of identifying a substance capable of inhibiting the ubiquitination comprising the use of β-nicotinamide adenine dinucleotide (β-NAD).

In one aspect, the present disclosure presents a method of identifying a substance capable of inhibiting the ubiquitination comprising the use of a protein capable of catalyzing ubiquitination process, wherein the protein capable of catalyzing ubiquitination process is selected from the group consisting of SdeA, SdeB, SdeC, SidE, any mutant protein of SdeA, SdeB, SdeC, or SidE, and any combination thereof.

In one aspect, the present disclosure presents a method of identifying a substance capable of inhibiting the ubiquitination comprising the use of a protein, wherein the protein is able to be ubiquinated with an ubiquitin through a ribose-phosphate link. In one aspect, the protein is selected from the group consisting of Rab1, Rab6A, Rab30, Rab33b, Rtn4, and Atlastin, any mutant form of Rab1, Rab6A, Rab30, Rab33b, Rtn4, Atlastin, and any combination thereof.

Those skilled in the art will recognize that numerous modifications can be made to the specific implementations described above. The implementations should not be limited to the particular limitations described. Other implementations may be possible. In addition, all references cited herein are indicative of the level of skill in the art and are hereby incorporated by reference in their entirety.

REFERENCES

1. Komander, D. & Rape, M. The ubiquitin code. Annu. Rev. Biochem. 81, 203-229 (2012).
2. Zinngrebe, J., Montinaro, A., Peltzer, N. & Walczak, H. Ubiquitin in the immune system. EMBO Rep. 15, 28-45 (2014).
3. Zhou, Y. & Zhu, Y. Diversity of bacterial manipulation of the host ubiquitin pathways. Cell. Microbiol. 17, 26-34 (2015).
4. Cui, J. et al. Glutamine deamidation and dysfunction of ubiquitin/NEDD8 induced by a bacterial effector family. Science 329, 1215-1218 (2010).
5. Xu, L. & Luo, Z. Q. Cell biology of infection by *Legionella pneumophila*. Microbes Infect. 15, 157-167 (2013).
6. Luo, Z. Q. & Isberg, R. R. Multiple substrates of the *Legionella pneumophila* Dot/Icm system identified by interbacterial protein transfer. Proc. Natl Acad. Sci. USA 101, 841-846 (2004).
7. Huang, L. et al. The E Block motif is associated with *Legionella pneumophila* translocated substrates. Cell. Microbiol. 13, 227-245 (2011).
8. Lifshitz, Z. et al. Computational modeling and experimental validation of the *Legionella* and *Coxiella* virulence-related type-IVB secretion signal. Proc. Natl Acad. Sci. USA 110, E707-E715 (2013).
9. Fontana, M. F. et al. Secreted bacterial effectors that inhibit host protein synthesis are critical for induction of the innate immune response to virulent *Legionella pneumophila*. PLoS Pathog. 7, e1001289 (2011).
10. Choy, A. et al. The *Legionella* effector RavZ inhibits host autophagy through irreversible Atg8 deconjugation. Science 338, 1072-1076 (2012).

11. Simon, S., Wagner, M. A., Rothmeier, E., Muller-Taubenberger, A. & Hilbi, H. Icm/Dot-dependent inhibition of phagocyte migration by *Legionella* is antagonized by a translocated Ran GTPase activator. Cell. Microbiol. 16, 977-992 (2014).
12. Rolando, M. et al. *Legionella pneumophila* effector RomA uniquely modifies host chromatin to repress gene expression and promote intracellular bacterial replication. Cell Host Microbe 13, 395-405 (2013).
13. Hsu, F. et al. Structural basis for substrate recognition by a unique *Legionella* phosphoinositide phosphatase. Proc. Natl Acad. Sci. USA 109, 13567-13572 (2012).
14. Zhu, W. & Luo, Z. Q. Cell biology and immunology lessons taught by *Legionella pneumophila*. Sci. China Life Sci. 59, 3-10 (2016).
15. Bardill, J. P., Miller, J. L. & Vogel, J. P. IcmS-dependent translocation of SdeA into macrophages by the *Legionella pneumophila* type IV secretion system. Mol. Microbiol. 56, 90-103 (2005).
16. Sakurai, J., Nagahama, M., Oda, M., Tsuge, H. & Kobayashi, K. *Clostridium perfringens* iota-toxin: structure and function. Toxins (Basel) 1, 208-228 (2009).
17. Wilde, C. & Aktories, K. The Rho-ADP-ribosylating C3 exoenzyme from *Clostridium botulinum* and related C3-like transferases. Toxicon 39, 1647-1660 (2001).
18. Ganesan, A. K., Frank, D. W., Misra, R. P., Schmidt, G. & Barbieri, J. T. *Pseudomonas aeruginosa* exoenzyme S ADP-ribosylates Ras at multiple sites. J. Biol. Chem. 273, 7332-7337 (1998).
19. Simon, N. C., Aktories, K. & Barbieri, J. T. Novel bacterial ADP-ribosylating toxins: structure and function. Nature Rev. Microbiol. 12, 599-611 (2014).
20. Havey, J. C. & Roy, C. R. Toxicity and SidJ-mediated suppression of toxicity require distinct regions in the SidE family of *Legionella pneumophila* effectors. Infect. Immun. 83, 3506-3514 (2015).
21. Jeong, K. C., Sexton, J. A. & Vogel, J. P. Spatiotemporal regulation of a *Legionella pneumophila* T4SS substrate by the metaeffector SidJ. PLoS Pathog. 11, e1004695 (2015).
22. Tan, Y., Arnold, R. J. & Luo, Z. Q. *Legionella pneumophila* regulates the small GTPase Rab1 activity by reversible phosphorylcholination. Proc. Natl Acad. Sci. USA 108, 21212-21217 (2011).
23. Swanson, M. S. & Isberg, R. R. Association of *Legionella pneumophila* with the macrophage endoplasmic reticulum. Infect. Immun. 63, 3609-3620 (1995).
24. Liu, Y. & Luo, Z. Q. The *Legionella pneumophila* effector SidJ is required for efficient recruitment of endoplasmic reticulum proteins to the bacterial phagosome. Infect. Immun. 75, 592-603 (2007).
25. Sherwood, R. K. & Roy, C. R. A. Rab-centric perspective of bacterial pathogen-occupied vacuoles. Cell Host Microbe 14, 256-268 (2013).
26. Ortiz Sandoval, C. & Simmen, T. Rab proteins of the endoplasmic reticulum: functions and interactors. Biochem. Soc. Trans. 40, 1426-1432 (2012).
27. Itoh, T. et al. Golgi-resident small GTPase Rab33B interacts with Atg16L and modulates autophagosome formation. Mol. Biol. Cell 19, 2916-2925 (2008).
28. Sheedlo, M. J. et al. Structural basis of substrate recognition by a bacterial deubiquitinase important for dynamics of phagosome ubiquitination. Proc. Natl Acad. Sci. USA (2015).
29. Herhaus, L. & Dikic, I. Expanding the ubiquitin code through post-translational modification. EMBO Rep. 16, 1071-1083 (2015).
30. Glowacki, G. et al. The family of toxin-related ecto-ADP-ribosyltransferases in humans and the mouse. Protein Sci. 11, 1657-1670 (2002).
31. Berger, K. H. & Isberg, R. R. Two distinct defects in intracellular growth complemented by a single genetic locus in *Legionella pneumophila*. Mol. Microbiol. 7, 7-19 (1993).
32. Xu, L. et al. Inhibition of host vacuolar H+-ATPase activity by a *Legionella pneumophila* effector. PLoS Pathog. 6, e1000822 (2010).
33. Tilney, L. G., Harb, O. S., Connelly, P. S., Robinson, C. G. & Roy, C. R. How the parasitic bacterium *Legionella pneumophila* modifies its phagosome and transforms it into rough ER: implications for conversion of plasma membrane to the ER membrane. J. Cell Sci. 114, 4637-4650 (2001).
34. Li, Z., Solomon, J. M. & Isberg, R. R. Dictyostelium discoideum strains lacking the RtoA protein are defective for maturation of the *Legionella pneumophila* replication vacuole. Cell. Microbiol. 7, 431-442 (2005).
35. Pan, X., Luhrmann, A., Satoh, A., Laskowski-Arce, M. A. & Roy, C. R. Ankyrin repeat proteins comprise a diverse family of bacterial type IV effectors. Science 320, 1651-1654(2008).
36. Fan, H. Y., Cheng, K. K. & Klein, H. L. Mutations in the RNA polymerase II transcription machinery suppress the hyperrecombination mutant Hpr1 □ of *Saccharomyces cerevisiae*. Genetics 142, 749-759 (1996).
37. Gietz, R. D., Schiestl, R. H., Willems, A. R. & Woods, R. A. Studies on the transformation of intact yeast cells by the LiAc/SS-DNA/PEG procedure. Yeast 11, 355-360 (1995).
38. Fazzio, T. G. & Tsukiyama, T. Chromatin remodeling in vivo: evidence for a nucleosome sliding mechanism. Mol. Cell 12, 1333-1340 (2003).
39. Duménil, G. & Isberg, R. R. The *Legionella pneumophila* IcmR protein exhibits chaperone activity for IcmQ by preventing its participation in high-molecular-weight complexes. Mol. Microbiol. 40, 1113-1127 (2001).
40. Conover, G. M., Derre, I., Vogel, J. P. & Isberg, R. R. The *Legionella pneumophila* LidA protein: a translocated substrate of the Dot/Icm system associated with maintenance of bacterial integrity. Mol. Microbiol. 48, 305-321 (2003).

The invention claimed is:

1. A method of identifying a-protein antagonist of Adenosine triphosphate (ATP) independent ubiquitination, comprising:
   providing an ATP independent ubiquitination system, wherein the ATP independent ubiquitin system comprising an adenosine diphosphate (ADP)-ribosylated ubiquitin, wherein the ADP-ribosylated ubiquitin is generated by a protein selected from the group consisting of SEQ ID NOs: 1-4 or a combination thereof, and β-nicotinamide adenine dinucleotide (β-NAD), wherein the protein adds an ADP to an ubiquitin from β-NAD, and a substrate selected from the group consisting of Rab1, Rab6A, Rab30, Rab33b, Rtn4 (Retieulon 4), and Atlastin;
   providing a series of substance to the ATP independent ubiquitin system to observe the substance's effect on the substrate ubiquitination by the ADP-ribosylated ubiquitin; and
   identifying at least one substance that prevents the substrate ubiquitination.

2. The method of claim 1, wherein the substance is selected from the group consisting of SEQ ID NOs: 8-11, or a combination thereof.

3. The method of claim 1, wherein the substance is an antibody to the ADP-ribosylated ubiquitin.

4. The method of claim 1, wherein the substance has a mutation corresponding to ADP-ribosylation site in a tryptic peptide $E_{34}$GIPPDQQRLIFAGK$_{48}$ of SEQ ID NO: 12 at position 42 of arginine.

* * * * *